United States Patent
Aksimentiev et al.

(10) Patent No.: US 11,441,118 B2
(45) Date of Patent: Sep. 13, 2022

(54) NUCLEIC ACID AND OTHER COMPOSITIONS AND METHODS FOR THE MODULATION OF CELL MEMBRANES

(71) Applicants: The Board of Trustees of the University of Illinois, Urbana, IL (US); Cambridge Enterprise Limited, Cambridge (GB)

(72) Inventors: Aleksei Aksimentiev, Urbana, IL (US); Ulrich F. Keyser, Cambridge (GB)

(73) Assignees: THE BOARD OF TRUSTEES OF THE UNIVERSITY OF ILLINOIS, Urbana, IL (US); CAMBRIDGE ENTERPRISE LIMITED, Cambridge (GB)

( * ) Notice: Subject to any disclaimer, the term of this patent is extended or adjusted under 35 U.S.C. 154(b) by 661 days.

(21) Appl. No.: 16/179,214

(22) Filed: Nov. 2, 2018

(65) Prior Publication Data
US 2019/0127682 A1    May 2, 2019

Related U.S. Application Data

(60) Provisional application No. 62/580,553, filed on Nov. 2, 2017.

(51) Int. Cl.
*C12N 15/11* (2006.01)
*A61K 31/711* (2006.01)
(Continued)

(52) U.S. Cl.
CPC .......... *C12N 5/0006* (2013.01); *A61K 9/5146* (2013.01); *A61K 31/711* (2013.01);
(Continued)

(58) Field of Classification Search
None
See application file for complete search history.

(56) References Cited

FOREIGN PATENT DOCUMENTS

EP     2695949 A1    2/2014
WO    WO-9412206 A1 *   6/1994  ............. A61P 17/00

OTHER PUBLICATIONS

Miyazaki et al., "Interaction of Antimicrobial Peptide Magainin 2 with Gangliosides as a Target for Human Cell Binding" Biochemistry vol. 51 pp. 10229-10235 (Year: 2012).*

(Continued)

*Primary Examiner* — Eric Olson
(74) *Attorney, Agent, or Firm* — Leydig, Voit & Mayer, Ltd

(57) ABSTRACT

The present invention provides compositions and methods for transferring phospholipids and other molecules between the leaflets of a cell membrane. The compositions comprise at least one nucleic acid or compound having a hydrophilic region, where the composition is able to form a nanostructure that forms a toroidal pore in a lipid membrane. The nucleic acid or hydrophilic region-containing compound further contains an attached molecule capable of inserting the nanostructure into the lipid membrane. The invention also provides methods for scrambling lipids and other molecules in a cell membrane, which can be used to alter the function of a selected cell or to facilitate the death of the cell. The scrambling activity of synthetic scramblases described herein outperforms previously known enzymatically active DNA nanostructures and naturally occurring scramblases, in some cases by several orders of magnitude.

18 Claims, 31 Drawing Sheets
(31 of 31 Drawing Sheet(s) Filed in Color)
Specification includes a Sequence Listing.

(51) Int. Cl.
A61K 31/713 (2006.01)
C12N 5/00 (2006.01)
A61K 9/51 (2006.01)
(52) U.S. Cl.
CPC ............ *A61K 31/713* (2013.01); *C12N 15/11* (2013.01); *C12N 15/111* (2013.01); *C12N 2310/3515* (2013.01)

(56) References Cited

OTHER PUBLICATIONS

Wang et al., "Facile Synthesis of Tetrafluorotyrosine and Its Application in pH Triggered Membrane Lysis" Organic Letters vol. 13 No. 2 pp. 236-239 (Year: 2011).*
Bansal et al., "Magainin, isolated from Xenopus laevis, induced Apoptosis in Human Cervical Carcinoma Cells" Journal of Pharmaceutical and Biosciences vol. 1 pp. 1-3 (Year: 2013).*
Abdul et al., "Protection against amyloid beta-peptide (1-42)-induced loss of phospholipid asymmetry in synaptosomal membranes by tricyclodecan-9-xanthogenate (D609) and ferulic acid ethyl ester: Implications for Alzheimer's disease", *Biochimica et Biophysica Acta (BBA)—Molecular Basis of Disease*, 1741(1-2):140-148 (2005).
Andersen, "Rattle: A "velocity" version of the shake algorithm for molecular dynamics calculations", *J. Comput. Phys.*, 52(1):24-34 (1983).
Batcho et al., "Optimized particle-mesh Ewald/multiple-time step integration for molecular dynamics simulations", *J. Chem. Phys.*, 115:4003-4018 (2001).
Bevers et al., "Transmembrane phospholipid distribution in blood cells: control mechanisms and pathophysiological significance", *Biological Chemistry*, 379(8-9):973-986 (1998).
Böckmann et al., "Effect of Sodium Chloride on a Lipid Bilayer", *Biophysical Journal*, 85(3):1647-1655 (2003).
Boon et al., "Facilitated Phosphatidylserine (PS) Flip-Flop and Thrombin Activation Using A Synthetic PS Scramblase", *J. Am. Chem. Soc.*, 125(27):8195-8201 (2003).
Bretscher, "Asymmetrical Lipid Bilayer Structure for Biological Membranes", *Nature New Biology*, 236: 11-12 (1972).
Burns et al., "A biomimetic DNA-based channel for the ligand-controlled transport of charged molecular cargo across a biological membrane", *Nature Nanotechnology*, 11:152-156 (2016).
Burns et al., "Lipid-Bilayer-Spanning DNA Nanopores with a Bifunctional Porphyrin Anchor", *Angewandte Chemie Int. Ed.*, 52(46):12069-12072 (2013).
Burns et al., "Self-Assembled DNA Nanopores That Span Lipid Bilayers", *Nano Lett.*, 13(6):2351-2356 (2013).
Castegna et al., "Modulation of phospholipid asymmetry in synaptosomal membranes by the lipid peroxidation products, 4-hydroxynonenal and acrolein: implications for Alzheimer's disease", *Brain Research*, 1004(1-2):193-197 (2004).
Comer et al., "Predicting the DNA Sequence Dependence of Nanopore Ion Current Using Atomic-Resolution Brownian Dynamics", *J. Phys. Chem. C.*, 116(5):3376-3393 (2012).
De Vries et al., "Molecular Dynamics Simulation of the Spontaneous Formation of a Small DPPC Vesicle in Water in Atomistic Detail", *J. Am. Chem. Soc.*, 126(14):4488-4489 (2004).
Devaux et al.,"How lipid flippases can modulate membrane structure", *Biochimica et Biophysica Acta (BBA)—Biomembranes*, 1778(7-8):1591-1600 (2008).
Douglas et al., "Rapid prototyping of 3D DNA—origami shapes with caDNAno", *Nucleic Acids Research*, 37(15):5001-5006 (2009).
Fattal et al., "Pore-Forming Peptides Induce Rapid Phospholipid Flip-Flop in Membranes", *Biochemistry*, 33(21):6721-6731 (1994).
Feller et al., "Constant pressure molecular dynamics simulation: The Langevin piston method", *J. Chem. Phys.*, 103:4613-4621 (1995).
Fouquet, "Quick Guide to STED Sample Preparation", *Confocal Application Letter, Resolution*, 49:1-12 (2014).

Göpfrich et al., "DNA-Tile Structures Induce Ionic Currents through Lipid Membranes", *Nano Lett.*, 15(5), 3134-3138 (2015).
Göpfrich et al., "Ion Channels Made from a Single Membrane-Spanning DNA Duplex", *Nano Lett.*, 16(7):4665-4669 (2016).
Göpfrich et al., "Large-Conductance Transmembrane Porin Made from DNA Origami", *ACS Nano.*, 10(9):8207-8214 (2016).
Goren et al., "Constitutive phospholipid scramblase activity of a G protein-coupled receptor", *Nature Communications*, 5:5115 (2014).
Gummadi et al., "Transbilayer movement of dipalmitoylphosphatidylcholine in proteoliposomes reconstituted from detergent extracts of endoplasmic reticulum", *J. Biol. Chem.*, 277:25337-25343 (2002).
Gurtovenko et al., "Chemically Induced Phospholipid Translocation Across Biological Membranes", *Langmuir*, 24(17):9656-9660 (2008).
Gurtovenko et al., "Molecular Mechanism for Lipid Flip-Flops", *J. Phys. Chem. B.*, 111(48):13554-13559 (2007).
Hoover, "Canonical dynamics: Equilibrium phase-space distributions", *Phys. Rev. A.*, 31: 1695-1697 (1985).
Khalid et al., ", DNA and lipid bilayers: self-assembly and insertion", *Journal of the Royal Society Interface*, 5(Supp. 3):S241-S250 (2008).
Krishnan et al., "Molecular transport through large-diameter DNA nanopores", *Nature Communications*, 7:12787 (2016).
Kucerka et al., "Structure of Fully Hydrated Fluid Phase Lipid Bilayers with Monounsaturated Chains", *The Journal of Membrane Biology*, 208(3):193-202 (2006).
Langecker et al., "Synthetic Lipid Membrane Channels Formed by Designed DNA Nanostructures", *Science*, 338(6109): 932-936 (2012).
Leontiadou et al., "Antimicrobial Peptides in Action", *J. Am. Chem. Soc.*, 128(37):12156-12161 (2006).
Li et al., "Confocal Imaging to Quantify Passive Transport across Biomimetic Lipid Membranes", *Anal. Chem.*, 82(18):7766-7771 (2010).
Li et al., "Ionic Conductivity, Structural Deformation, and Programmable Anisotropy of DNA Origami in Electric Field", *ACS/Nano.*, 9(2):1420-1433 (2015).
Mackerell et al., "All-Atom Empirical Potential for Molecular Modeling and Dynamics Studies of Proteins" J Phys Chem B 1998 vol. 102 pp. 3586-3616.
Maffeo et al., "De novo reconstruction of DNA origami structures through atomistic molecular dynamics simulation", *Nucleic Acids Research*, 44(7):3013-3019 (2016).
Malvezzi et al., "$Ca^{2+}$-dependent phospholipid scrambling by a reconstituted TMEM16 ion channel", *Nature Communications*, 4:2367 (2013).
Martyna et al., "Constant pressure molecular dynamics algorithms", *J. Chem. Phys.*, 101:4177-4189 (1994).
Matsuzaki et al., "An Antimicrobial Peptide, Magainin 2, Induced Rapid Flip-Flop of Phospholipids Coupled with Pore Formation and Peptide Translocation", *Biochemistry*, 35(35):11361-11368 (1996).
Mcintyre et al., "Fluorescence assay for phospholipid membrane asymmetry", *Biochemistry*, 30(51):11819-11827 (1991).
Menon et al., "Opsin is a phospholipid flippase", *Current Biology*, 21(2):149-153 (2011).
Miyamoto et al., "Settle: An analytical version of the SHAKE and RATTLE algorithm for rigid water models", *J. Comput. Chem.*, 13:952-962 (1992).
Morra et al., "Mechanisms of Lipid Scrambling by the G Protein-Coupled Receptor Opsin", *Structure*, 26(2):356-367.e3 (2018).
Nakano et al., "Flip-Flop of Phospholipids in Vesicles: Kinetic Analysis with Time-Resolved Small-Angle Neutron Scattering", *J. Phys. Chem. B*, 113(19):6745-6748 (2009).
Nakao et al., "Membrane-Spanning Sequences in Endoplasmic Reticulum Proteins Promote Phospholipid Flip-Flop", *Biophysical Journal*, 110(12):2689-2697 (2016).
Nishioka et al., "A Photon-Fueled DNA Nanodevice that Contains Two Different Photoswitches", *Angewandte Chemie, International Edition*, 124:1191-1194 (2012).
Nosé, "A unified formulation of the constant temperature molecular dynamics methods", *J. Chem. Phys.*, 81:511-519 (1984).
Phillips et al., "Scalable molecular dynamics with NAMD", *Journal of Computational Chemistry*, 26(16):1781-1802 (2005).

(56) References Cited

OTHER PUBLICATIONS

Pomorski et al., "Lipid somersaults: Uncovering the mechanisms of protein-mediated lipid flipping", *Progress in Lipid Research*, 64:69-84 (2016).

Pomorski et al., "Tracking down lipid flippases and their biological functions", *Journal of Cell Science*, 117:805-813 (2004).

Ravichandran et al., "Engulfment of apoptotic cells: signals for a good meal", *Nature Reviews Immunology*, 7:964-974 (2007).

Sahu et al., "Phospholipid scramblases: An overview", *Archives of Biochemistry and Biophysics*, 462(1):103-114 (2007).

Schlosser et al., "Biologically Inspired Synthetic Enzymes Made from DNA", *Chemistry & Biology*, 16(3):311-322 (2009).

Seifert et al., "Bilayer-Spanning DNA Nanopores with Voltage-Switching between Open and Closed State", *ACS Nano.*, 9(2):1117-1126 (2015).

Shaw et al., "Anton 2: Raising the Bar for Performance and Programmability in a Special-Purpose Molecular Dynamics Supercomputer," *Proceedings of the International Conference for High Performance Computing, Networking, Storage and Analysis (SC14)*, Piscataway, NJ: IEEE, 2014, pp. 41-53.

Silverman, "Catalytic DNA: Scope, Applications, and Biochemistry of Deoxyribozymes", *Trends in Biochemical Sciences*, 41(7):595-609 (2016).

Siu et al., "Biomolecular simulations of membranes: Physical properties from different force fields", *J. Chem. Phys.*, 128:125103 (2008).

Skeel et al., "Correcting Mesh-Based Force Calculations to Conserve Both Energy and Momentum in Molecular Dynamics Simulations", *J. Comput. Phys.*, 225(1):1-5 (2007).

Vallabhapurapu et al., "Variation in human cancer cell external phosphatidylserine is regulated by flippase activity and intracellular calcium", *Oncotarget.*, 6(33):34375-34388 (2015).

Vanommeslaeghe et al., "Automation of the CHARMM General Force Field (CGenFF) I: Bond Perception and Atom Typing", *J. Chem. Inf. Model.*, 52(12):3144-3154 (2012).

Venkatesan et al., "Lipid bilayer coated $Al_2O_3$ nanopore sensors: towards a hybrid biological solid-state nanopore", *Biomedical Microdevices*, 13(4):671-682 (2011).

Williamson et al., "Continuous Analysis of the Mechanism of Activated Transbilayer Lipid Movement in Platelets", *Biochemistry*, 34(33):10448-10455 (1995).

Yang et al., "Photo-Controllable DNA Origami Nanostructures Assembling into Predesigned Multiorientational Patterns", *J. Am. Chem. Soc.*, 134(51):20645-20653 (2012).

Yoo et al., "Improved Parameterization of Amine-Carboxylate and Amine-Phosphate Interactions for Molecular Dynamics Simulations Using the CHARMM and AMBER Force Fields", *J. Chem. Theory Comput.*, 12(1):430-443 (2016).

Yoo et al., "In situ structure and dynamics of DNA origami determined through molecular dynamics simulations", *Proc. Natl. Acad. Sci. USA.*, 110(50):20099-20104 (2013).

Yoo et al., "Improved Parametrization of Li+, Na+, K+, and $Mg^{2+}$ Ions for All-Atom Molecular Dynamics Simulations of Nucleic Acid Systems", *J. Phys. Chem. Lett.*, 3(1):45-50 (2012).

Yoo et al., "Molecular Dynamics of Membrane-Spanning DNA Channels: Conductance Mechanism, Electro-Osmotic Transport, and Mechanical Gating", *J. Phys. Chem. Lett.*, 6(23):4680-4687 (2015).

Yu et al., "Identification of a lipid scrambling domain in ANO6/TMEM16F", Emory University School of Medicine (2015).

Zachowski, "Phospholipids in animal eukaryotic membranes: transverse asymmetry and movement", *Biochemical Journal*, 294(Pt. 1):1-14 (1993).

Zwaal et al., "Scott syndrome, a bleeding disorder caused by defective scrambling of membrane phospholipids", *Biochimica et Biophysica Acta (BBA)—Molecular and Cell Biology of Lipids*, 1636(1-2):119-128 (2004).

\* cited by examiner

NUCLEIC ACID AND OTHER COMPOSITIONS AND METHODS FOR THE MODULATION OF CELL MEMBRANES

CROSS-REFERENCE TO RELATED APPLICATIONS

This application claims priority from U.S. Provisional Patent Application No. 62/580,553, filed Nov. 2, 2017, which is incorporated by reference herein to the extent that there is no inconsistency with the present disclosure.

STATEMENT REGARDING FEDERALLY SPONSORED RESEARCH OR DEVELOPMENT

This invention was made with government support under DMR-1507985, PHY-1430124, and EEC-1227034 awarded by the National Science Foundation, P41-RR005969 awarded by the National Institutes of Health. The government has certain rights in the invention. The project leading to this application has received funding from the European Research Council (ERC) under the European Union's Horizon 2020 research and innovation programme (grant agreement No 647144).

BACKGROUND OF THE INVENTION

The cell membrane (also known as the plasma membrane) is a biological membrane that separates the interior of the cell from the outside environment. The basic function of the plasma membrane is to protect the cell from its surroundings. It comprises a lipid bilayer having an inner leaflet and an outer leaflet, where both leaflets contain phospholipids, glycolipids, embedded proteins, and other molecules. However, the exact composition will be different between the inner leaflet and the outer leaflet. In particular, the two leaflets of a mammalian plasma membrane are made up from chemically distinct mixtures of phospholipids (1). In other words, the composition of the leaflets is asymmetric. Control over the asymmetric partitioning of phospholipids and other molecules is critically important to cell health and function. For example, loss of asymmetry can trigger unregulated apoptosis (2) and could lead to the development of Alzheimer's disease (3). Three groups of enzymes, scramblases, flippases, and floppases (4, 5), are known proteins able to transport lipids from one leaflet to the other.

In contrast to flippases and floppases, which require energy input for maintaining the asymmetric lipid composition, scramblases are activated to rapidly and passively dismantle the asymmetric partitioning of the lipids, which typically occurs during critical events such as cell activation, blood coagulation and apoptosis (6-9). Defects in the enzyme-catalyzed scrambling of membrane phospholipids in blood cells can hinder thrombin formation and lead to Scott syndrome (10). Impaired lipid scrambling has also been shown to weaken the immune system and evoke the autoimmune response by exposing self-antigens (11). Thus, development of biocompatible and easy to adapt synthetic analogues to repair and/or control lipid scrambling activity in cell membranes is of considerable medical interest.

Membrane-spanning DNA nanopore structures have emerged as primary synthetic mimics of biological membrane channels (12-20). Critical for lipid membrane insertions of DNA nanopore structures was the inclusion of hydrophobic anchors (12, 14-20) as the hydrophobic core of the lipid bilayer presents a high energetic barrier for DNA (21). However, nanopores generated by conventional synthetic structures remain limited in the rate that they are able to transport molecules across the cell membrane. Additionally, the transport of molecules through conventionally generated nanopores is typically limited by the size of the pore which is formed in the center of the nanopore structure. Accordingly, what is needed are molecules which are able to be inserted into the membranes of selected cells and are able to transfer molecules between the two leaflets of the cell membrane more efficiently than conventional synthetic nanopore structures.

SUMMARY OF THE INVENTION

The present invention provides compositions and methods for transferring phospholipids and other molecules between the leaflets of a cell membrane. In particular, the compositions are able to be inserted into a lipid membrane and form a toroidal pore. As used herein, a "toroidal pore" refers to a channel or nanopore in a lipid bilayer where the hydrophilic surfaces of the inner and outer leaflets are fused together to form a continuous structure. This is in contrast to nanopores formed by conventional nanostructures, which form a tube or barrel structure through the bilayer where the hydrophilic surfaces of the inner and outer leaflets do not fuse and instead remain distinct from one another. A toroidal pore between the inner and outer leaflet allows for easier transport of lipids within the bilayer to move from one leaflet to the other, and may allow smaller nanostructures to be used.

The present invention also provides methods for scrambling lipids and other molecules in a cell membrane by administering the compositions of the present invention to the cell membrane. These methods can be used to alter the function of a selected cell, to facilitate the death of the cell, or even transport a drug, chemical agent, or lipid vesicle into the interior of the cell. An aspect of the present invention provides fully functional synthetic scramblases that facilitate rapid mixing of lipids and other molecules between membrane leaflets. The scrambling activities of synthetic scramblases described herein outperform previously known enzymatically active DNA nanostructures and naturally occurring scramblases, preferably by several orders of magnitude.

In an embodiment, the present invention provides a composition comprising one or more hydrophilic regions forming a nanostructure and one or more hydrophobic or amphiphilic molecules attached to the one or more hydrophilic regions, wherein the one or more hydrophobic or amphiphilic molecules are able to insert the composition into a lipid membrane and wherein the nanostructure forms a toroidal pore in the lipid membrane.

The composition described in the embodiments herein comprises one or more nucleic acids, nanoparticles, nanotubes, proteins, carbohydrates, or combinations thereof, which form the nanostructure. In an embodiment, the composition comprises one or more: (i) nucleic acids, (ii) functionalized organic and inorganic nanoparticles, including but not limited to nanotubes, where the hydrophilic core of the nanoparticle is decorated with hydrophobic or amphiphilic tags that facilitate insertion; (iii) peptides that optionally have a central or cylindrical hydrophilic charge (for example, a peptide nanotube) and hydrophobic/amphiphilic flexible N and C terminals; (iv) similar objects having a hydrophilic core and one or more hydrophobic/amphiphilic tags made from a combination of synthetic and/or biological materials; and (v) combinations thereof. Preferably, the nanostructure has a width or diameter of 0.1 nm to 10 nm, 0.5 nm to 5 nm, 0.5 nm to 3 nm, or 1 nm to 3 nm. The height of the nanostructure (i.e., the dimension of the nanostructure that extends from above the outer surface of the membrane to below the inner surface of the membrane) should preferably be at least as large as the thickness of the membrane, but can be much greater. In an embodiment, the nanostructure has a height of at least 3 nm, at least 5 nm, at least 7 nm, at least 10 nm, at least 12 nm, at least 15 nm, at least 20 nm, or at least 25 nm.

Increasing the size of the nanostructure will generally make it more difficult to insert the hydrophilic nanostructure into the lipid membrane. However, increasing the size of the nanostructure, particularly the width or circumference of the nanostructure, will also increase the size of the toroidal pore and will increase the scrambling rate caused by the composition.

Preferably, the composition comprises one or more nucleic acids which form the nanostructure. Nucleic acids suitable for use in the present invention include deoxyribonucleic acid (DNA), ribonucleic acid (RNA), locked nucleic acid (LNA), peptide nucleic acid (PNA), glycol nucleic acid (GNA), threose nucleic acid (TNA), phosphorodiamidate morpholino oligomers (PMO), and combinations thereof. Preferably, the one or more nucleic acids which form the nanostructure are DNA, RNA, or combinations thereof.

In an embodiment, the composition comprises one or more nucleic acids, where at least one of the nucleic acids comprises a polynucleotide sequence having at least 90% sequence identity (preferably at least 95%, 97%, or 100% sequence identity) to any of SEQ ID NOs:1-8. In a further embodiment, each nucleic acid comprises a polynucleotide sequence having at least 90% sequence identity (preferably at least 95%, 97%, or 100% sequence identity) to any of SEQ ID NOs:1-8. In an embodiment, the composition comprises one or more nucleic acids able to form a nanostructure substantially similar to a nanostructure formed by any one of the nucleic acids of SEQ ID NOs:1-8 or combinations thereof.

In an embodiment, the composition comprises one or more nucleic acids forming a nanostructure comprising at least one interconnected nucleic acid duplex. Optionally, the composition comprises two nucleic acids forming a nanostructure comprising an interconnected nucleic acid duplex, four nucleic acids forming a nanostructure comprising two interconnected nucleic acid duplexes, six nucleic acids forming a nanostructure comprising three interconnected nucleic acid duplexes, eight nucleic acids forming a nanostructure comprising four interconnected nucleic acid duplexes, or ten or more nucleic acids forming a nanostructure comprising five or more interconnected nucleic acid duplexes.

The molecules able to insert the composition into a lipid membrane can be any molecule having hydrophobic or amphiphilic moieties and which are known in the art able to be inserted into a lipid membrane. For example, such molecules include, but are not limited to, cholesterol, α-tocopherol, stearate, palmitate, porphyrine, and derivatives thereof (further examples can be found at www<dot>biomers<dot>net/en/products/DNA_Lipophilic_modifications.html). Preferably, the molecules are hydrophobic molecules. The hydrophobic or amphiphilic molecules are attached to hydrophilic regions of the composition, preferably through a linker group.

Preferably, the linker group is a substituted or unsubstituted aliphatic group having from 1-30 carbon atoms, 1-20 carbon atoms, 1-16 atoms, 1-12 carbon atoms, 1-10 carbon atoms, 1-6 carbon atoms, or 1-3 carbon atoms. In a further embodiment, one or more carbons in the linker group are substituted with an oxygen atom to form an ether (—C—O—C—) group. Optionally, the linker group comprises triethylene glycol (TEG), diethylene glycol (DEG), ethylene glycol (MEG), or polyethylene glycol (PEG).

The length of the linker may be used to control the size of the toroidal pore. Adjusting the linker length and composition, including its charge, can also make the present compounds selective to specific lipid types and sizes. For example, increasing the length of the linker may increase the distance between the hydrophilic regions of the nanostructure and the surface of the membrane leaflets, which may allow bulkier lipids to more easily move pass the nanostructure from one leaflet to the other.

In an embodiment, the molecule capable of inserting the composition into a lipid membrane has the structure:

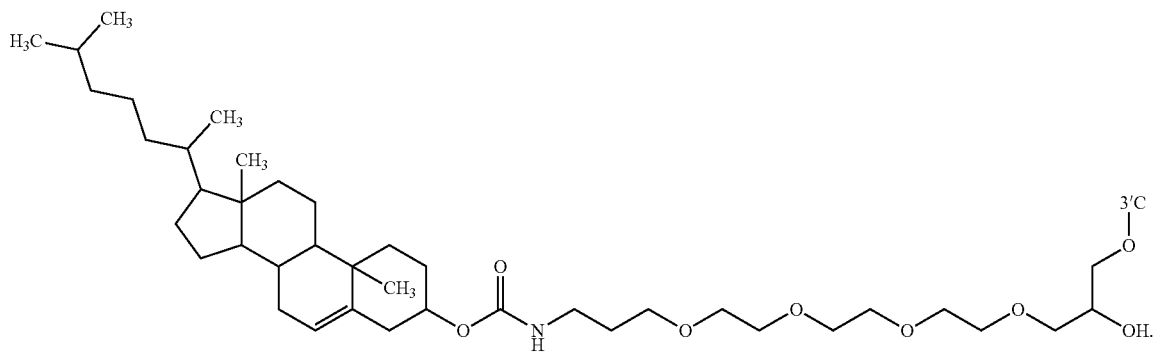

The hydrophilic groups can also be modified to allow the compound to be more efficiently inserted into a selected lipid membrane, or to selectively transport specified molecules between the plasma membrane leaflets. For example, the charge of the nucleic acid backbone can be reduced by chemistry to allow the nucleic acids to insert into a lipid membrane more easily.

The hydrophilic regions of the composition can be modified to attach to the linker group or directly to the hydrophilic or amphiphilic moiety. For example, where the nanostructure is formed by one or more nucleic acids, the one or more molecules able to insert the composition into a lipid membrane are attached to the 5' ends or 3' ends of the nucleic acids. In an embodiment, the composition comprises two or more molecules able to insert the composition into a lipid membrane, which are attached to the 5' ends or 3' ends of at least two nucleic acids.

In an embodiment, the nanostructure comprises an assembly of eight nucleic acids having at least 90% sequence identity (preferably at least 95%, 97%, or 100% sequence identity) to SEQ ID NO:1-8. Preferably, the one or more hydrophobic or amphiphilic molecules able to insert the composition into the lipid membrane are attached to the nucleic acids corresponding to SEQ ID NO:2 and SEQ ID NO:4.

The composition may further comprises a tag capable of allowing the composition to be detected once administered to a cell or tissue. The tag can be any tag suitable for use with biological systems and include, but are not limited to, dyes, fluorescent markers, isotopically labeled molecules, and radioactive tags. In an embodiment, the tag is a fluorescent marker, preferably Cy3.

In an embodiment, the composition further comprises a cell-specific anchor to target the composition to a specific cell type. For example, the cell specific anchor is optionally a peptide or nucleic acid that directs the body of a subject to deliver the composition to a specific cell type, that causes the composition to bind to a receptor of a specified cell type, or that causes the specified cell type to partially absorb the composition. In an embodiment, the cell type specific anchor includes, but is not limited to, RNA, DNA, peptides, cell specific antibodies, and nanobodies. The composition may further comprise a peptide or other molecule having enzymatic activity other than the scrambling function of the composition.

In an embodiment, the present invention provides a method of scrambling lipids or other molecules in a first and second leaflet of a biological membrane, the method comprising:
(a) contacting the biological membrane with a composition comprising one or more hydrophilic regions forming a nanostructure and one or more hydrophobic or amphiphilic molecules attached to the one or more hydrophilic regions, wherein said one or more hydrophobic or amphiphilic molecules are able to insert the nanostructure into the biological membrane; and
(b) inserting the nanostructure into the biological membrane and forming a toroidal pore in the biological membrane surrounding the nanostructure, where the hydrophilic surfaces of the first and second leaflets are fused together to form a continuous structure, Lipids and molecules within a cell membrane may be naturally transported from one leaflet to another by naturally occurring biological enzymes. Preferably, the lipids and/or other molecules of the present invention are transported to the opposite leaflet at a rate greater than the transport rate of a control biological membrane which was not contacted with the composition. A control biological membrane refers to biological membrane which is of the same type (i.e., same composition or cell type) of the treated biological membrane.

In an embodiment, the lipids and/or other molecules are transported to the opposite leaflet at a rate at least 2 times greater than a control biological membrane, preferably at a rate at least 3 times greater than a control biological membrane, at a rate at least 4 times greater than a control biological membrane, at a rate at least 5 times greater than a control biological membrane, at a rate at least 10 times greater than a control biological membrane, at a rate at least 20 times greater than a control biological membrane, at a rate at least 50 times greater than a control biological membrane, at a rate at least 100 times greater than a control biological membrane, at a rate at least 500 times greater than a control biological membrane, or at a rate at least 1,000 times greater than a control biological membrane.

The lipids, other molecules, or both, can be selectively transported so that just the lipids or other molecules in the first leaflet are transported to the second leaflet, just the lipids or other molecules in the second leaflet are transported to the first leaflet, or the lipids or other molecules in both leaflets are transported. Additionally, the lipids, other molecules, or both, can be selectively transported so that only selected lipids or molecules are transported from one leaflet to the other.

In an embodiment, the present invention provides a method for altering a biological state of a cell having a lipid membrane with a first leaflet and a second leaflet, the method comprising:

(a) contacting the lipid membrane of the cell with a composition comprising one or more hydrophilic regions forming a nanostructure and one or more hydrophobic or amphiphilic molecules attached to the one or more hydrophilic regions, wherein said one or more hydrophobic or amphiphilic molecules are able to insert the nanostructure into the lipid membrane; and (b) inserting the nanostructure into the lipid membrane and forming a toroidal pore in the lipid membrane surrounding the nanostructure, where the hydrophilic surfaces of the first and second leaflets are fused together to form a continuous structure, wherein selected lipids, other molecules, or both, in the first leaflet are transported to the second leaflet at a rate greater than a transport rate of a control lipid membrane which was not contacted with the composition, and wherein the increased rate of transportation alters the amount of the selected lipids, other molecules, or both, in the first and second leaflets, thereby altering the biological state of the cell.

In a further embodiment, the increased rate of transportation of the selected lipids homogenizes the lipid composition between the first and second leaflet. Homogenizing the lipid composition of specified cells can increase thrombin formation and blood clotting. Alternatively, homogenizing the lipid composition induces or marks cells for apoptosis.

The increased rate of transportation of the selected lipids, other molecules, or both, may also regulate the amount of the selected lipids, other molecules, or both in the first and/or second leaflet in order to treat a medical condition. In an embodiment, the increased rate of transportation may increase the amount of antigens, receptors, or signaling peptides in the outer leaflet of the membrane, thereby increasing a cellular activity. For example, the increased rate of transportation may increase the number of antigens present in the outer leaflet of the cell membrane thereby increasing an antibody response directed against the cell.

In another embodiment, the increased rate of transportation may decrease the amount of antigens, receptors, or signaling peptides in the outer leaflet of the membrane, thereby decreasing a cellular activity. For example, the increased rate of transportation may decrease the number of self-antigens present in the outer leaflet of the cell membrane thereby reducing an autoimmune disease response.

Altering the biological state of a cell may further be directed to specific selected cells. In an embodiment, the composition further comprises an activation molecule or mechanism able to cause a conformal change in the composition structure when exposed to stimuli, where the conformal change activates the nanostructure to be inserted into the lipid membrane and to form the toroidal pore. Thus, the composition will not cause molecules to be transported between the different leaflets of the cell membrane until the composition is exposed to the stimuli.

The stimuli can be any external stimuli or internal cellular changes including, but not limited to, chemical, thermal, mechanical, electric potential, or electromagnetic triggering of structural changes within the nanostructure. In an embodiment, the stimuli comprise exposure to electromagnetic radiation, including but not limited to ultraviolet light, a change in pH, or a chemical agent. In a further embodiment, the activating mechanism comprises an azobenzene molecule attached to the composition and the stimuli comprises ultraviolet light which causes the azobenzene to stabilize the molecule forming the nanostructure. In another embodiment, the activating mechanism comprises one or more molecules attached to the composition, wherein the one or more molecules are able to undergo conformational changes in response to a change in pH, particularly decrease in the pH in the local environment. This can be beneficial as cancer cells are often associated with a relatively lower pH environment.

Accordingly, the biological state of a cell can be selectively altered by exposing only desired cells with the activating stimuli. For example, the composition can be widely administered to a plurality of cells in a subject but only a selected portion of the plurality of cells is exposed to the stimuli. As a result, only nanostructures within the selected portion of the plurality of cells will be activated. In a further example, the compositions comprise an anchor molecule which allows the composition to bind to a molecule on specific desired cells in a subject (such as a peptide present on the surface of a cancer cell). After the compositions have been bound to the desired cells, the subject (or a specific region of the subject) is exposed to an activating light source which causes the nanoparticles to be inserted into the cell membranes and facilitate the transport of lipids and/or other molecules between the two leaflets. In instances where the nanostructures cause the rapid homogenization of lipids, and therefore cell apoptosis, this method can be used as a way to kill the selected cells.

In another embodiment, the present invention provides a method for delivering a drug, chemical agent, or lipid vesicle into the interior of a cell having a lipid membrane, the method comprising:
  (a) administering a therapeutic amount of the drug, chemical agent, or a lipid vesicle containing a vesicle lipid membrane and a therapeutic amount of the drug or chemical agent, to the surface of the lipid membrane of the cell;
  (b) contacting the lipid membrane of the cell or the lipid membrane of the vesicle with a composition, said composition comprising one or more hydrophilic regions forming a nanostructure, and one or more hydrophobic or amphiphilic molecules attached to the one or more hydrophilic regions, wherein said one or more hydrophobic or amphiphilic molecules are able to insert the nanostructure into the lipid membrane of the cell or lipid vesicle; and
  (c) inserting the nanostructure into the lipid membrane of the cell or lipid vesicle and forming a toroidal pore in the lipid membrane surrounding the nanostructure;
wherein the therapeutic amount of the drug or chemical agent, or vesicle containing the therapeutic amount of the drug or chemical agent, is transported into the interior of the cell. The drug or chemical agent can be any therapeutic compound or agent that can be inserted into the outer leaflet of the cell membrane, or is capable of being encapsulated by a lipid vesicle. In an embodiment, the drug or chemical agent is hydrophobic. Optionally, the lipid vesicle, cell membrane, or both, contain a receptor protein able to bind the lipid vesicle to the cell membrane. Furthermore, the insertion of the nanostructure into the cell membrane or vesicle lipid membrane may be activated by the binding of the receptor.

In an embodiment, the nanostructure is inserted in the lipid membrane of the cell, and the therapeutic amount of the drug or chemical agent, or the vesicle containing the therapeutic amount of the drug or chemical agent, is transported into the interior of the cell via the toroidal pore formed in the lipid membrane of the cell. Alternatively, the nanostructure is inserted in the lipid membrane of the vesicle, and the drug or chemical agent within the lipid vesicle is transported to the surface of the cell through the toroidal pore where it is subsequently absorbed or taken in by the cell. In an embodiment, the interior of the lipid vesicle, such as the interior leaflet of the vesicle membrane, contains an activating lipid able to induce endocytosis or absorption by the cell. In this scenario, the nanostructure is inserted in the lipid membrane of the vesicle, wherein the activating lipid is transported to the surface of the cell through the toroidal pore and causes the cell membrane to absorb the drug, chemical agent or lipid vesicle.

The features, objects and advantages other than those set forth above will become more readily apparent when consideration is given to the detailed description below and the drawings described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3. Selective scrambling of lipids and other molecules produced by a DNA nanopore. The nanostructure, linker, and/or hydrophilic or amphiphilic molecule form a nanopore which allows certain lipids and other molecules (PC and PA) to pass through the nanopore, while preventing other lipids or molecules (PE) from passing through.

Cut-away view showing the DNA nanostructure (blue and yellow) embedded in a DPhPE lipid membrane (gray) via cholesterol tags (red). Lipid head groups located in the upper and lower leaflet of the bilayer at 0.2 µs are highlighted using purple and green spheres, respectively. Bottom: Top view of the simulated system; the electrolyte solution is not shown for clarity. Black ellipses highlight DPhPE head groups that resided at 0.2 µs in the lower leaflet of the bilayer.

Figure 6:
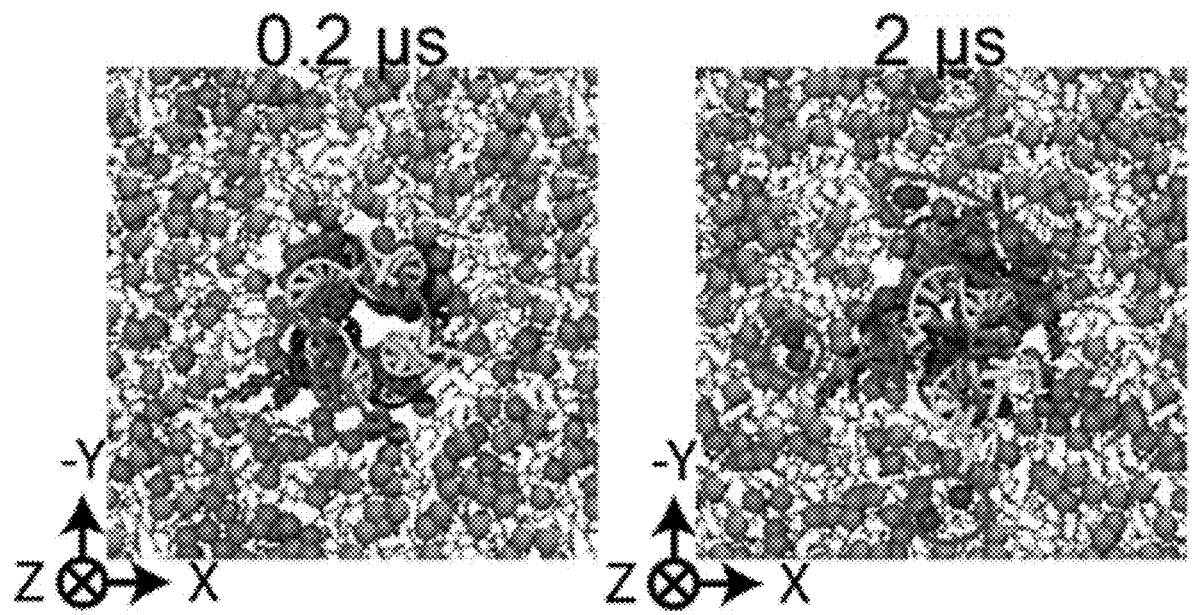

FIG. 6. Bottom-side view of the simulated system at the beginning and at the end of the free equilibration simulation. The DNA nanostructure consisting of four interconnected DNA duplexes (blue and yellow) is embedded in a DPhPE lipid membrane (gray) via cholesterol tags (red). The head groups of the DPhPE molecules found in the upper/lower leaflets of the bilayer at 0.2 µs are highlighted using purple/green spheres, respectively. The DPhPE head groups that reside at 0.2 µs in the upper leaflet of the bilayer are highlighted using red circles. The electrolyte solution is not shown for clarity.

Figure 7:
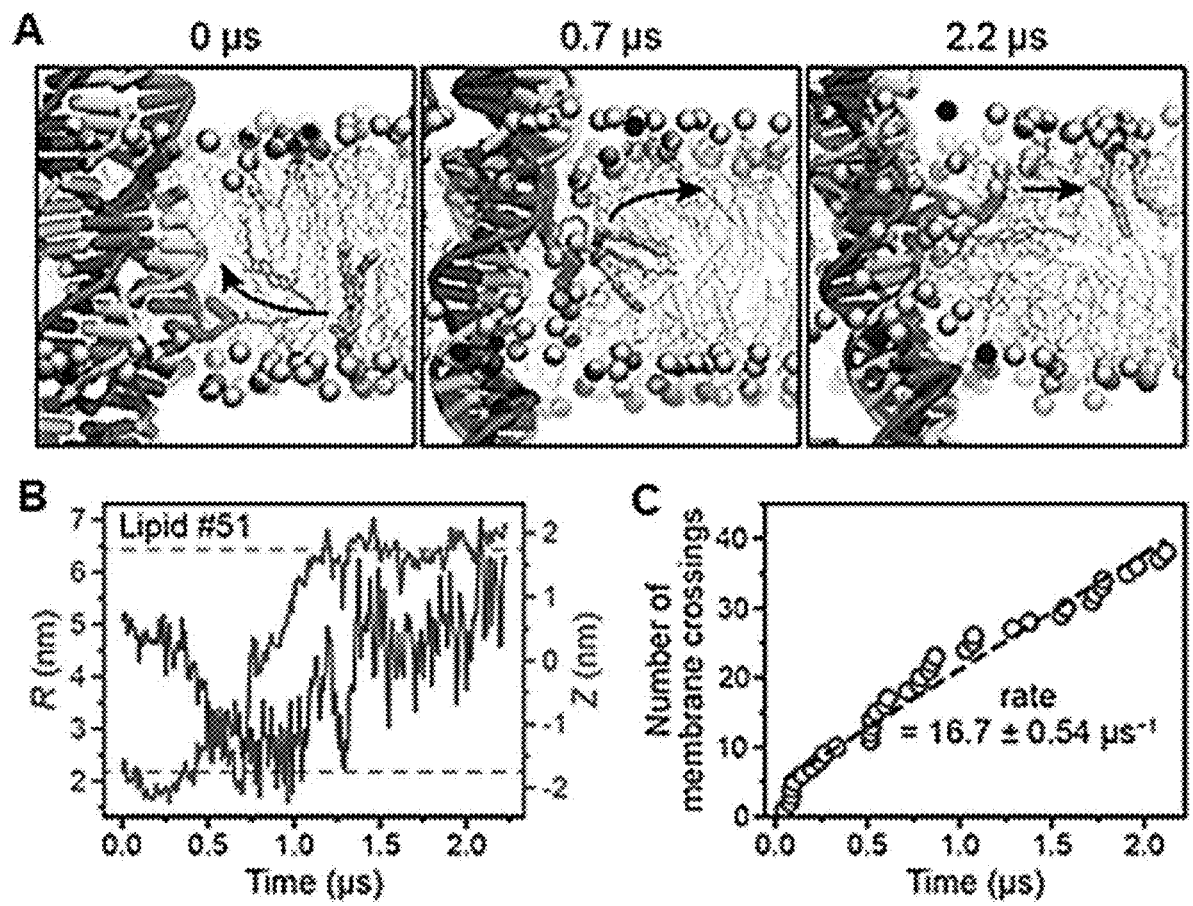
Figure 8:
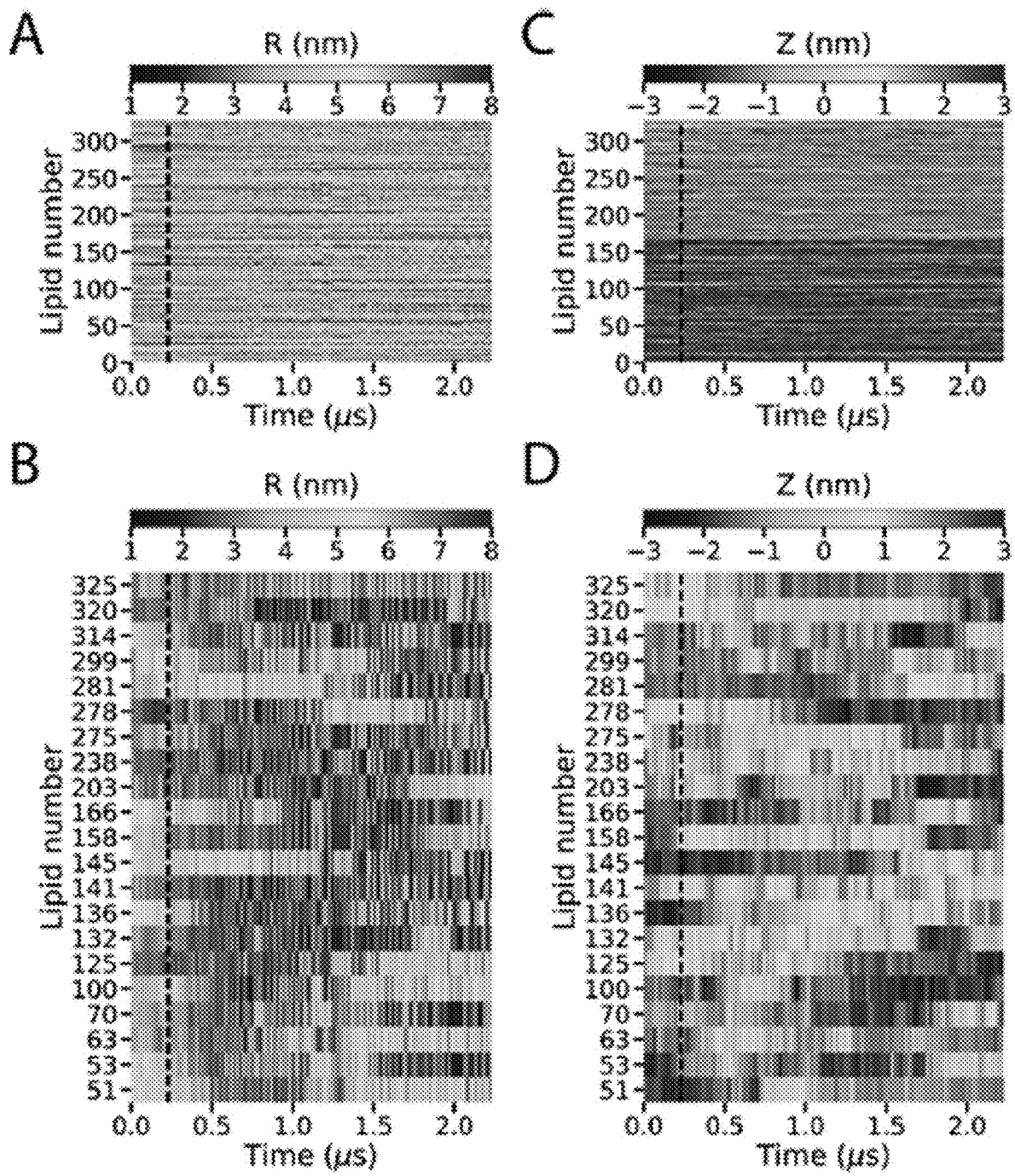

FIG. 7. Sequence of microscopic conformations illustrating spontaneous inter-leaflet transfer of one lipid molecule (#51) during the 2.2 µs MD simulation (panel A). For clarity, all other lipid molecules are shown as a different representation; the electrolyte solution is not shown. (Panel B) Radial distance relative to the center of mass of the nanostructure R (left axis) and the Z coordinate of the phosphorus atoms (right axis) of a lipid molecule (#51, see FIG. 2, panel B, and FIG. 4, panel A) undergoing a complete transfer from the lower to the upper leaflet of the bilayer. Dashed red lines indicate Z-coordinate thresholds for the upper and lower bilayer leaflet. Data shown were sampled at 0.24 ns and averaged in 9.6 ns blocks. FIG. 8 shows additional examples of inter-leaflet lipid transfer. (Panel C) Cumulative number of inter-leaflet transfer events versus simulation time. A linear fit (black line) yields the average transfer rate lipids per µs; the error indicates the estimated standard deviation of the non-linear least squares fit.

FIG. 8. Spontaneous displacement of lipids during MD simulations of the DNA nanostructure embedded in the DPhPE lipid membrane. The color maps indicate the radial distance from the center the nanostructure R (panels A and B) and the Z coordinate (panels C and D) of the lipid molecules versus simulation time. The radial distance was computed relative to the center of mass of the DNA nanostructure; Z=0 was defined to be at the center of mass of the lipid membrane. Panels A and C characterize displacements of all lipids in the simulation system whereas panels B and D characterize displacements of only those lipids that moved from one leaflet of the membrane to the other ($Z_{max}$>1.75 nm and $Z_{min}$<−1.75 nm). The black dashed lines (at 0.23 µs) indicate the beginning of free equilibration. Data shown were sampled every 0.24 ns.

Figure 9:
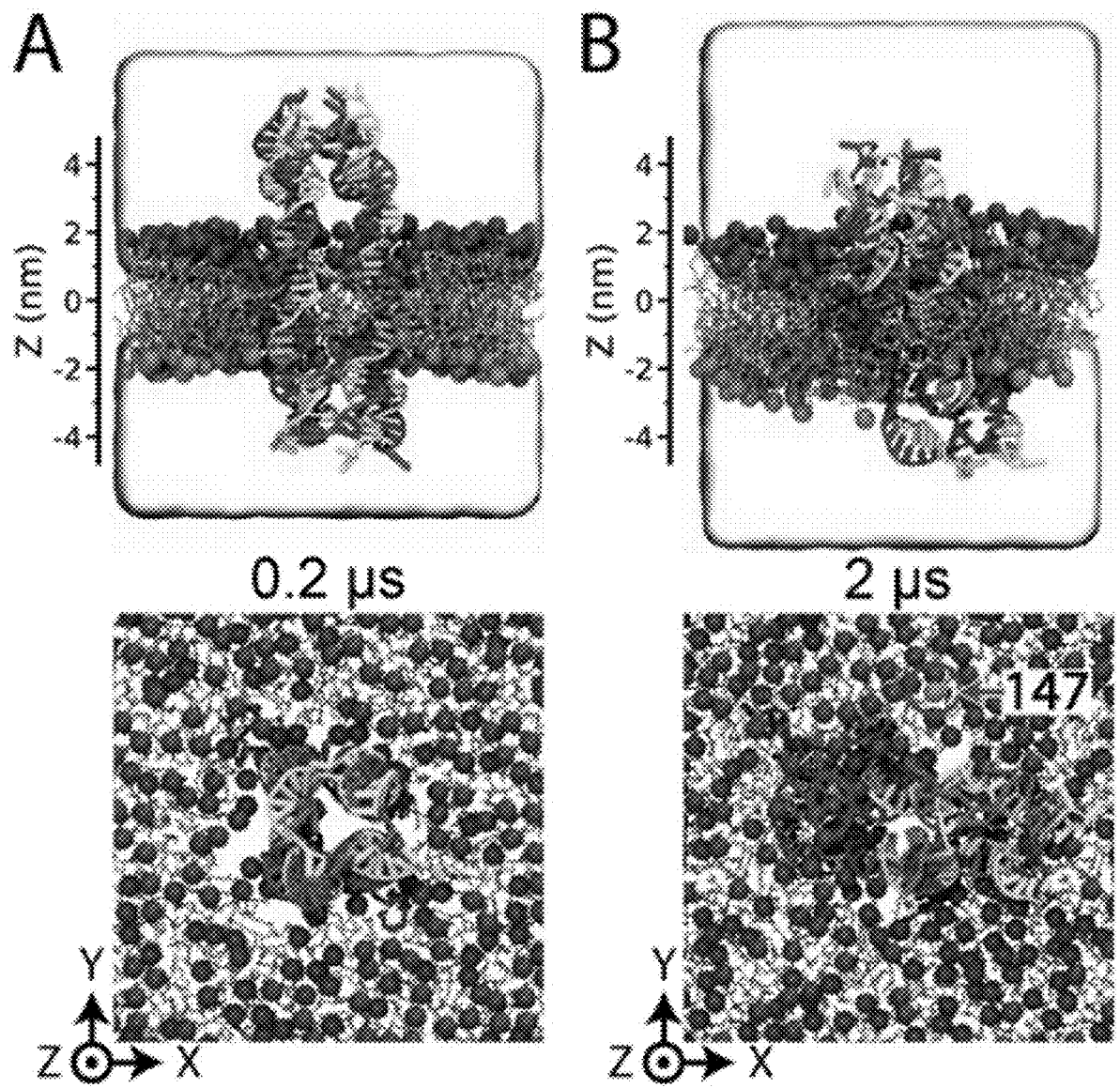

FIG. 9. Repeat all-atom simulation of lipid scrambling induced by a DNA nanostructure. Microscopic configuration of the simulated system at the beginning (panel A) and the end (panel B) of free equilibration simulation. (Top) Cut-away view of the simulated system, showing a DNA nanostructure (blue and yellow) embedded in a DPhPC lipid membrane (gray) via cholesterol tags (red). The head groups of the DPhPC molecules found in the upper and lower leaflets of the bilayer at 0.2 µs are highlighted using purple and green spheres, respectively. The semitransparent molecular surface illustrates the volume occupied by 1 M KCl electrolyte, revealing a toroidal water-filled pore surrounding the nanostructure. (Bottom) Top-view of the simulated system; the electrolyte solution is not shown for clarity. The DPhPC head groups that reside at 0.2 µs in the lower leaflet of the bilayer are highlighted using red circles.

Figure 10:
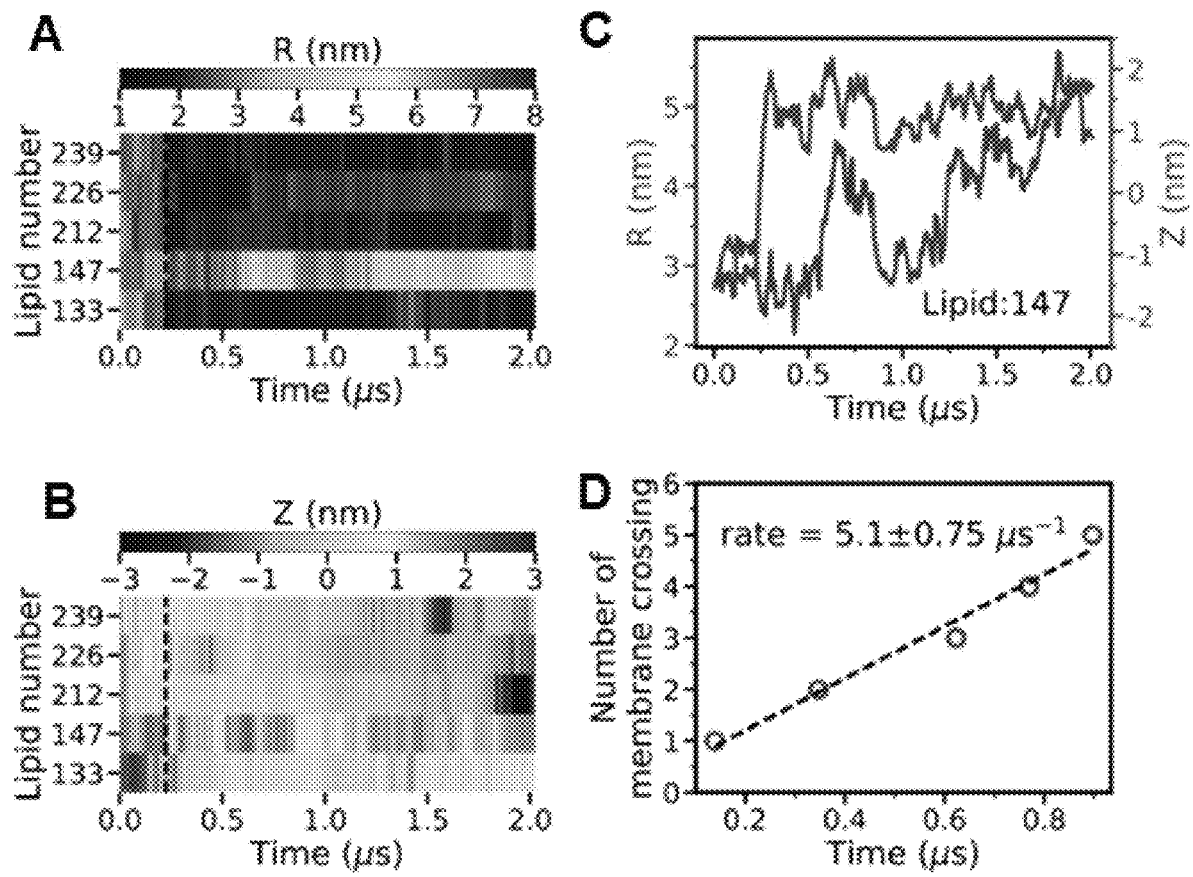

FIG. 10. The radial distance from the center of mass of the nanostructure R (panel A) and the Z coordinate (panel B) of the phosphorus atoms of several lipids during the simulation. The black dashed lines (at 0.22 µs) indicate the beginning of free equilibration. The lipids featured in the plot moved from one leaflet to the other ($Z_{max}$>1.75 nm and $Z_{min}$<−1.75 nm). Data shown were sampled every 0.24 ns. (Panel C) R and Z traces of one lipid molecule (number 147, see FIG. 9, panel B) undergoing a complete passage from the lower to the upper leaflets of the bilayer. The data shown was sampled at 0.24 ns and averaged in 9.6 ns blocks. (Panel D) The cumulative number of inter-leaflet lipid transfer events versus simulation time. The black line shows a linear fit. The simulated transfer rate is 5.1 lipids per µs. A lower inter-leaflet transfer rate (is comparison to the DPhPE system) could result from the overestimation of the attractive interactions between DNA phosphates and the head groups of DPhPC lipids.

Figure 11:
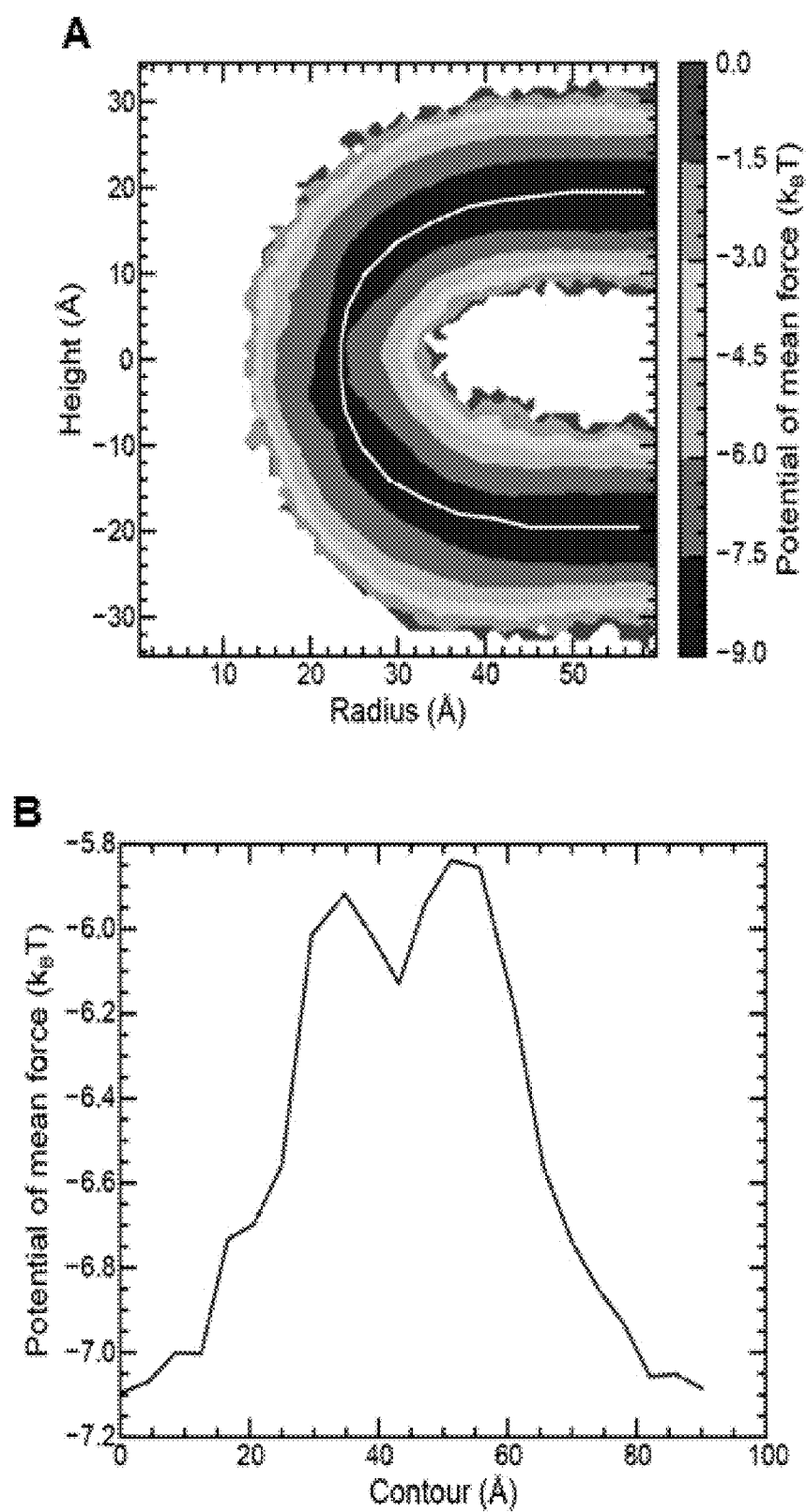

FIG. 11. Energetics of lipid scrambling. (Panel A) Two-dimensional potential of mean force (PMF) for a lipid headgroup near the toroidal pore. The PMF was obtained by Boltzmann inversion of the average density of lipid phosphorus atoms. To obtain the density, the system was translated at each frame of the trajectory so that the center of mass of all lipid atoms within 2 nm of DNA was at the origin. Following that, a two-dimensional histogram was constructed by binning the radial- and Z-coordinates of each phosphorus atom during the 2-µs MD trajectory. An approximate transition path for moving a lipid molecule from one leaflet to the other is drawn as a white line. The transition path was obtained by selecting all bins with a density greater that 1% of the maximum and iteratively removing bins from the edges until a single path of bins remained. (Panel B) Free energy profile along the transition path for a lipid moving from one leaflet to the other. To compute the free energy profile, all bins in the 2D histogram were assigned to the nearest transition path bin. The free energy at each transition path bin was calculated from the Boltzmann-weighted average of the free energies of its assigned bins from panel a. The contour at zero corresponds to the bin with radial and Z-coordinates of 59 and −20 Å, respectively.

Figure 12:
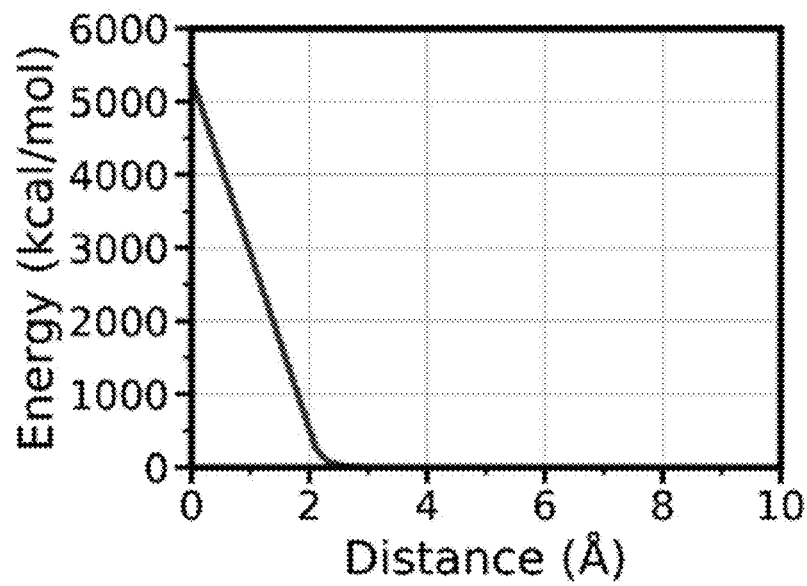

FIG. 12. Potential energy of two BD beads as a function of the inter-bead distance.

Figure 13:
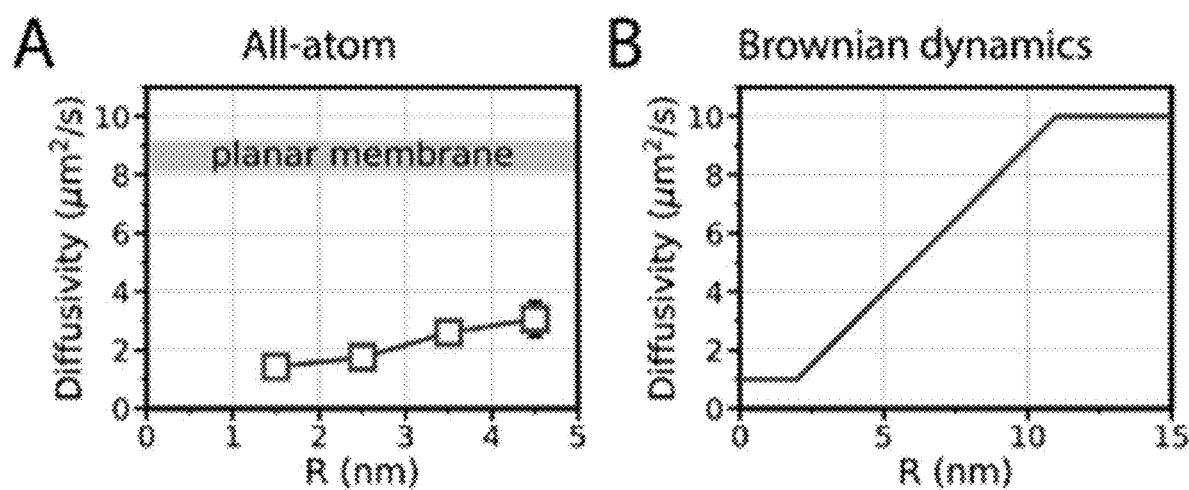

FIG. 13. Local diffusivity of lipid head groups as a function of the distance to the central axis of the DNA nanostructure R derived from the analysis of the all-atom MD simulation (panel A) and defined in BD simulations of the toroidal pore (panel B). In panel A, the error bars indicate standard deviation evaluated by bootstrapping the MD trajectory into four equal-length parts. The green area indicates the range of lipid diffusivity values observed in the simulations of a planar DPhPC bilayer system. The membrane patch simulated using the all-atom MD method is too small for the lipids to attain diffusive properties of a free bilayer system. Calculations of local diffusivities are described below.

Figure 14:
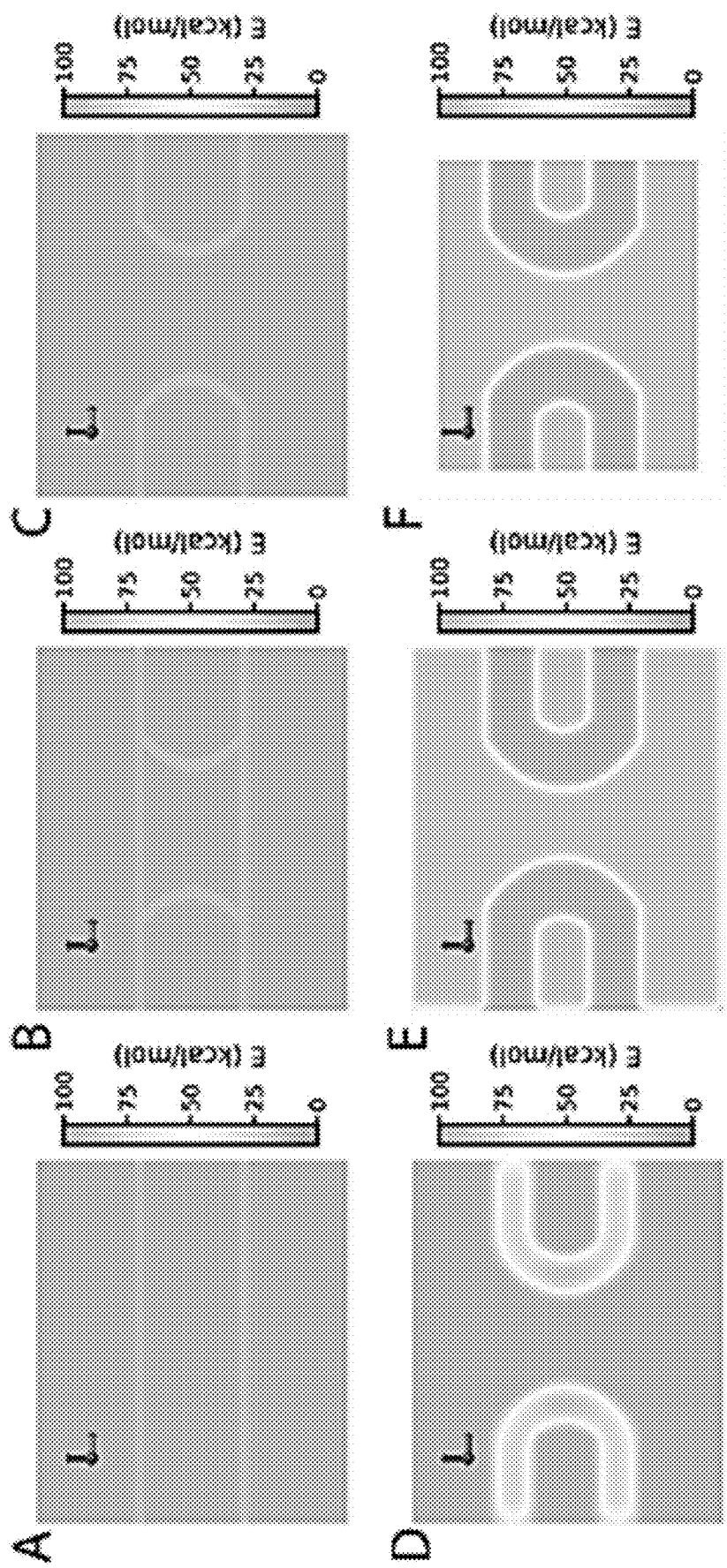

FIG. 14. Generation of a 3D grid-based potential for BD simulation of the toroidal pore. The sequence of images (panels A-F) illustrate the six steps of the potential generation procedure. Each image shows the same cross section of the 3D potential map; the plane of the cross section passes normal to the membrane through the central axis of the toroidal pore.

Figure 15:
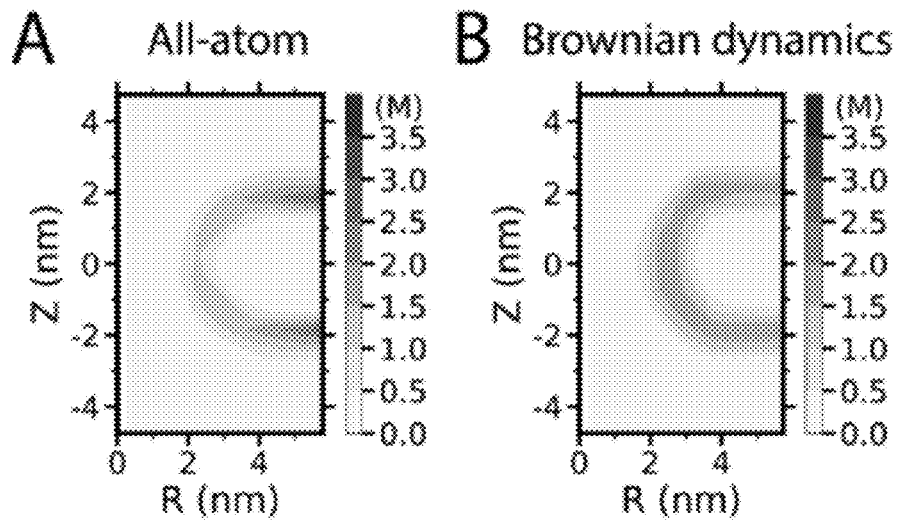

FIG. 15. Steady-state local concentration of phosphorus atoms of the lipid head groups in all-atom (Panel A) and Brownian dynamics (Panel B) simulations of the L=12 nm system. The data shown were radially averaged as described further below.

Figure 16:
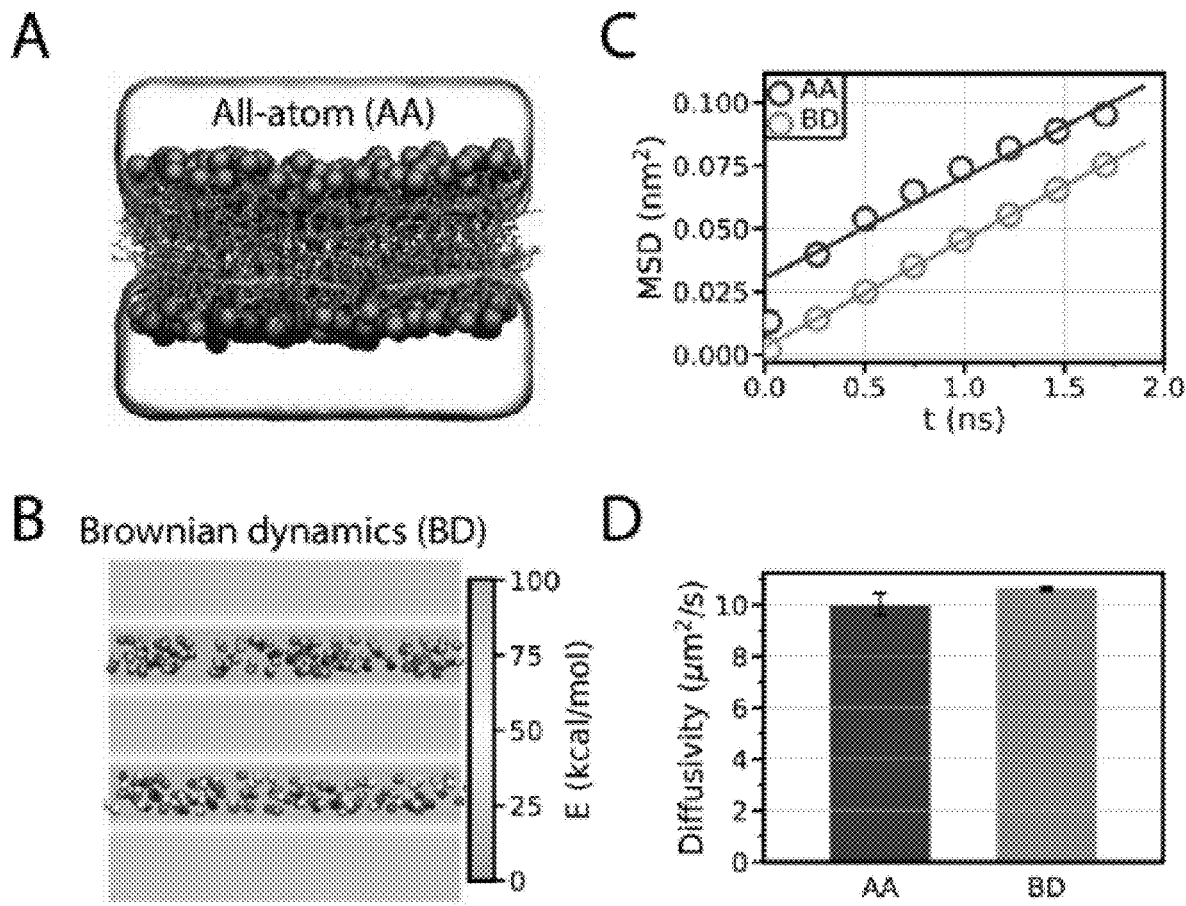

FIG. 16. Time scale comparison of the all-atom MD and BD approaches. (Panel A) All-atom model of a planar DPhPC lipid bilayer. The head and tail parts of the lipids are colored in black and green, respectively. The electrolyte solution (1 M KCl and 50 mM $MgCl_2$) is shown using a semitransparent molecular surface, ions are not explicitly shown. (Panel B) BD model of a planar lipid bilayer system. The green and yellow spheres represent the phosphorus atoms of the lipid bilayer membrane in the upper and lower leaflet, respectively. The color map illustrates a cross section of the potential energy grid that mimics the presence of the water-lipid interface. (Panel C) Mean squared displacement (MSD) of the phosphorus atoms (AA) and BD beads (BD) versus time. (Panel D) The 2D diffusivity of lipid head groups in all-atom (AA) and BD simulations. The error bars represent the standard deviation of the diffusivity values among the four quarters of the original trajectories.

Figure 17:
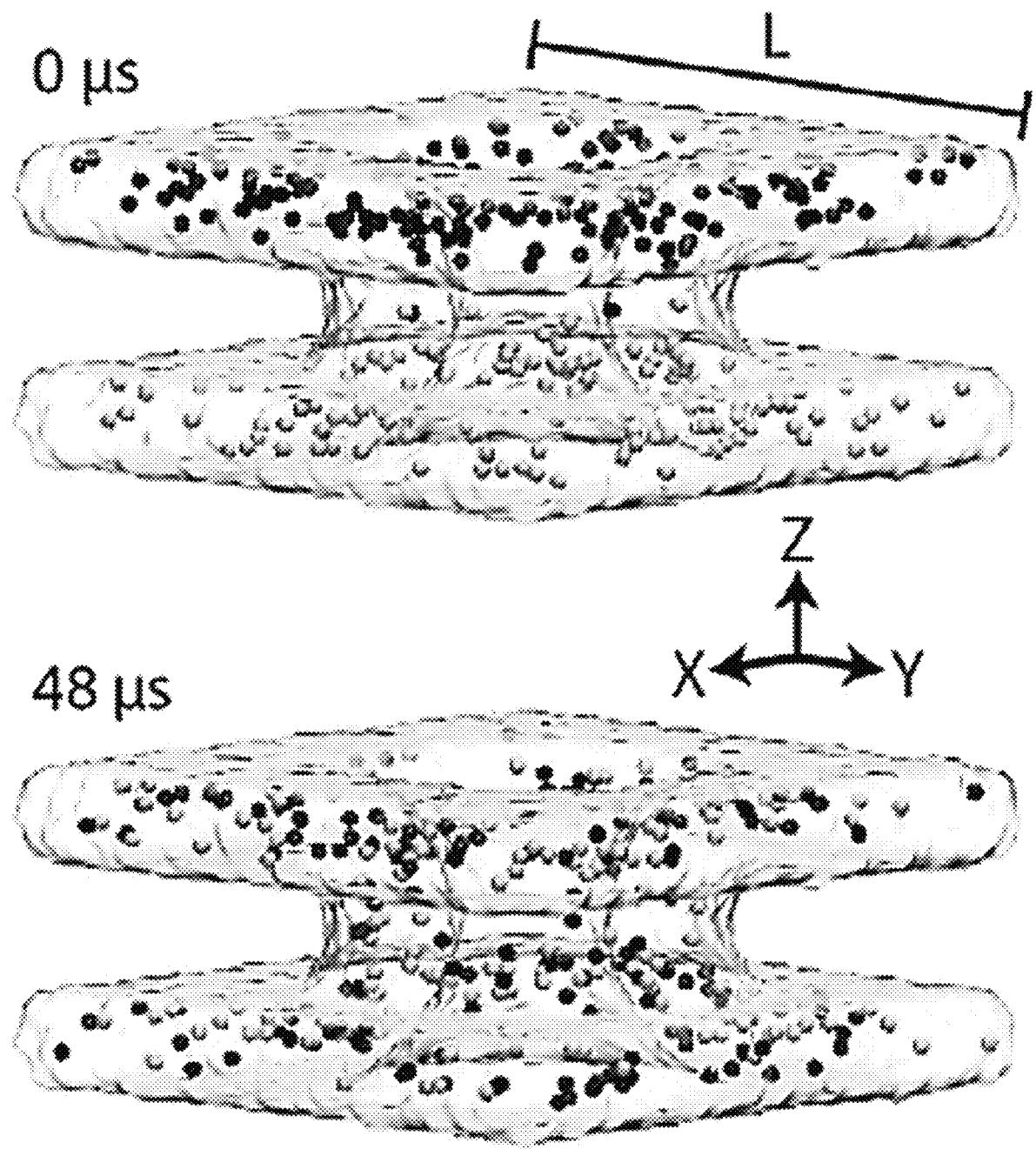

FIG. 17. BD simulation of lipid scrambling. Distribution of lipid head groups at the beginning (0 μs) and after 48 μs of BD simulation. Black and yellow spheres represent lipid head groups initially located in the upper and lower bilayer leaflets, respectively. The cyan semi-transparent surface schematically illustrates the volume accessible to lipid head groups during the simulation; L denotes the size of the lipid patch (here L=12 nm).

Figure 18:
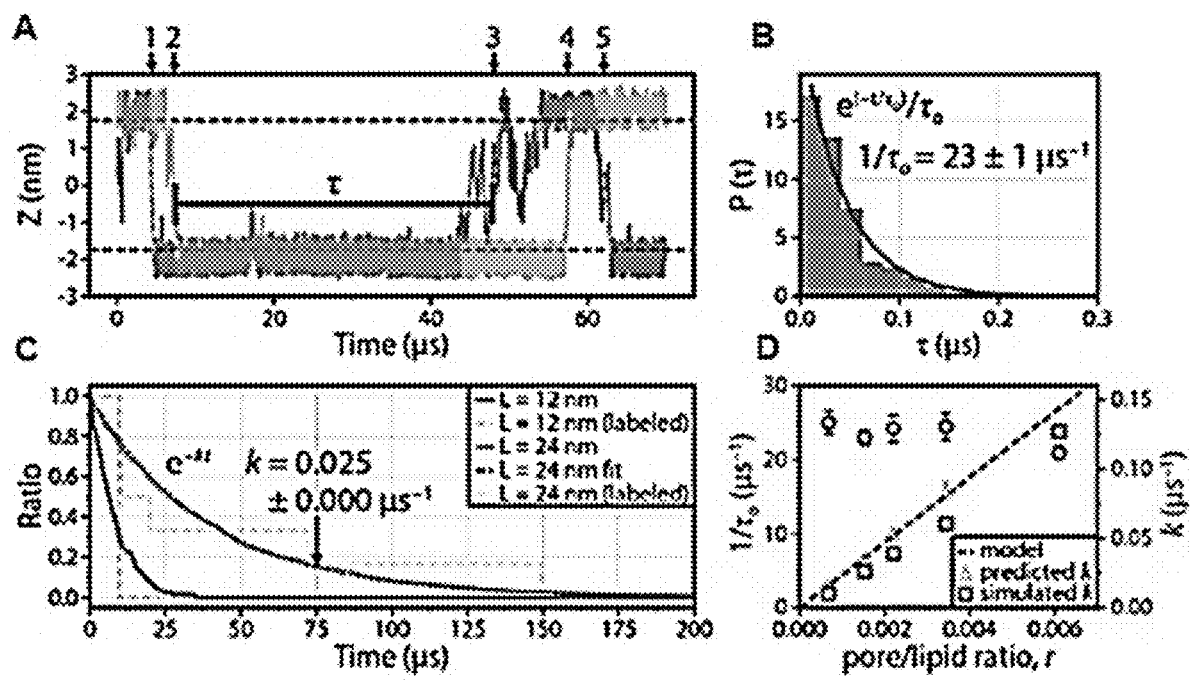

FIG. 18. Z coordinates of two representative lipid head groups (Panel A). Horizontal lines (at Z=±1.75 nm) indicate approximate boundaries of upper and lower leaflets. The traces feature five inter-leaflet transfer events; T defines the interval between two consecutive events. Head group trajectories were sampled every 24 ns. (Panel B) Normalized probability of observing an inter-leaflet transfer event within time interval T. An exponential fit (red line) yields the average transfer rate $1/\tau_o=23.0\pm1.03$ $\mu s^{-1}$. Data were obtained from a 500 μs trajectory of the L=24 nm system sampled every 24 ns. (Panel C) Fraction of lipid head groups remaining in the upper bilayer leaflet versus time elapsed from the beginning of the simulation. Data are shown for two systems differing by the size of the lipid patch. Lipids reentering the leaflet were not included in the fraction calculation. The black dashed line shows an exponential fit to the curves; the fitting parameter k is the scrambling rate. Dashed lines plot the same quantity for randomly chosen lipids mimicking experimental conditions where only a small amount of fluorescently labeled lipids is used to assess lipid scrambling. (Panel D) Simulated transfer rate (left axis) and scrambling rate (right axis) versus pore-to-lipid ratio. Data were derived from BD simulations of systems of different lipid patch size (L=12, 16, 20, 24 and 36 nm). Scrambling rate extracted directly from the simulation is plotted using squares. Dashed line plots $k=r/\langle\tau_o\rangle$ curve; transparent triangles indicate $k=r/\tau_o$, where $1/\langle\tau_o\rangle$ and $1/\tau_o$ are system size-averaged and system size-specific lipid transfer rates, respectively. Error bars indicate standard deviation.

Figure 19:
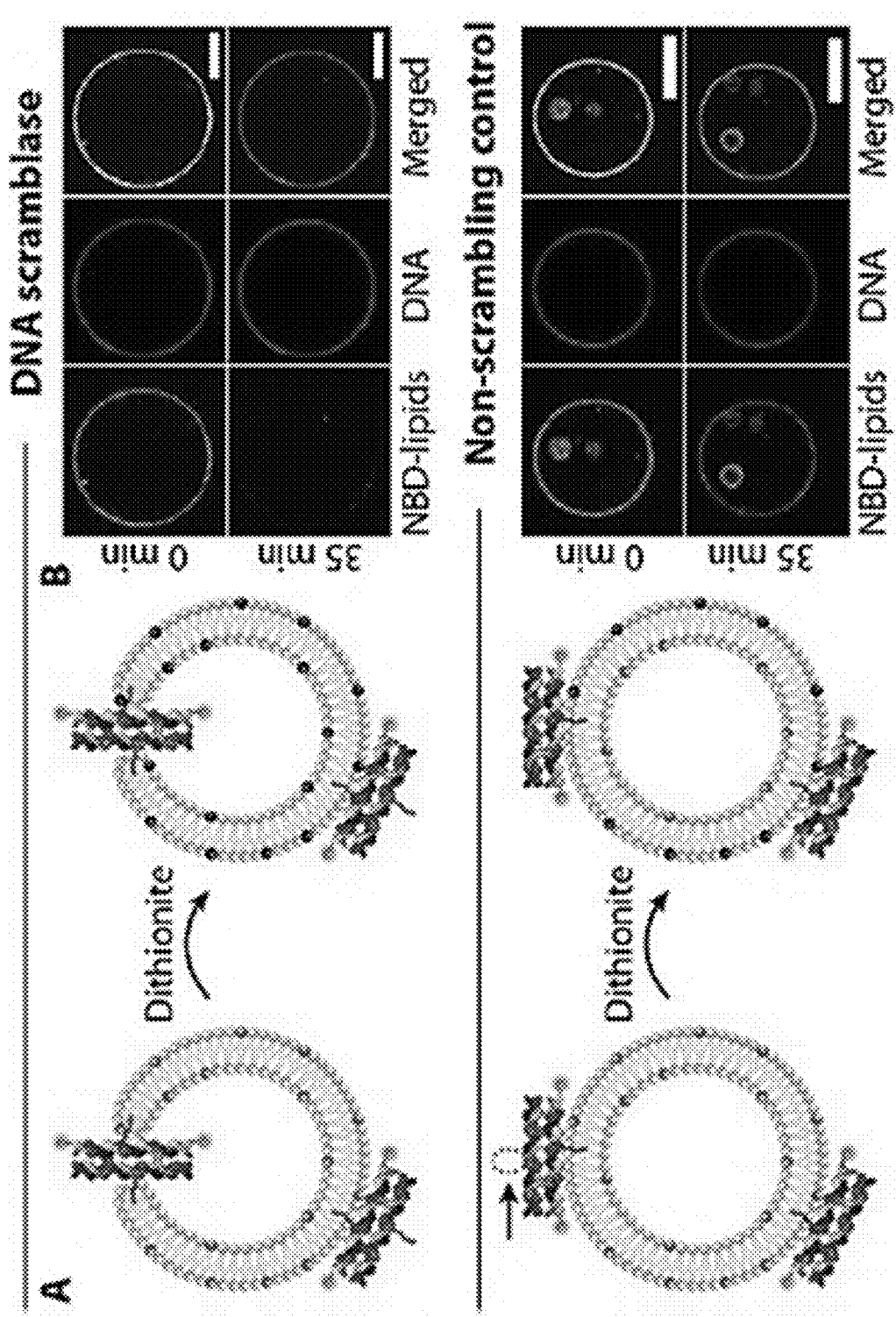

FIG. 19. Experimental demonstration of lipid scrambling by DNA nanostructures in lipid vesicles and human cells. (Panel A) Schematic illustration of dithionite reduction assay. POPC (gray) vesicles containing a fraction of NBD-labeled lipids (green) are incubated with DNA constructs tagged with Cy3 dye (red spheres). Upon dithionite addition, NBD fluorophores are irreversibly reduced (black). The nanostructure design containing two cholesterol modifications (2C, top) allows for membrane insertion to induce lipid scrambling whereas the constructs with one cholesterol (1C, bottom) do not. (Panel B) Confocal fluorescence microscopy images of GUVs containing NBD fluorophores (green) and incubated with Cy3-labeled DNA nanostructures (red) showing the same vesicle before and 35 minutes after dithionite addition roughly at the equatorial plane. The third column displays a merged image of the red and green channels. Scale bars are 10 μm.

Figure 20:
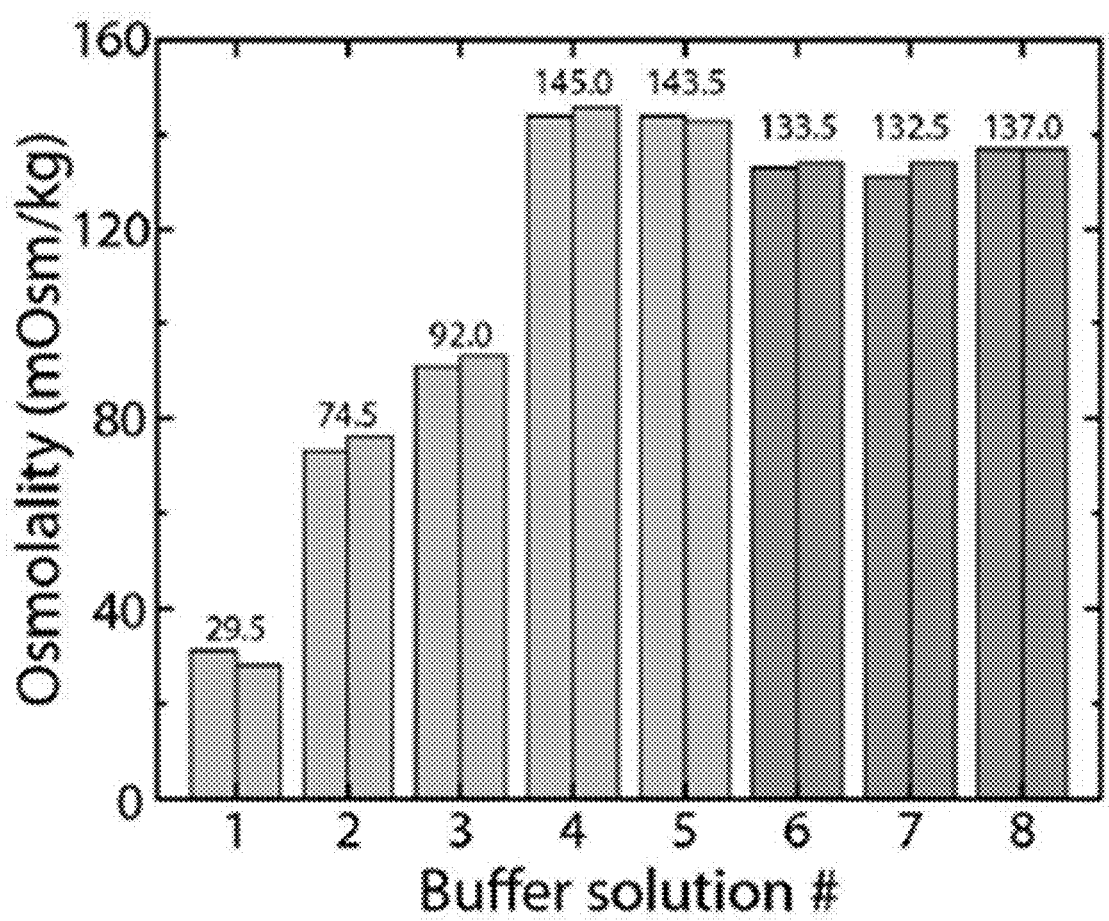

FIG. 20. Osmolality measurements of buffer solutions used in dithionite reduction assays. A freezing point osmometer (Automatic Micro-Osmometer Type 11, Roebling) was calibrated at 0 mOsm/kg with distilled water and at 300 mOsm/kg with a standard solution. Columns represent two measurement repeats and values their mean (for buffer conditions see Table 3). Blue bars denote solutions that giant unilamellar vesicles were in contact with.

Figure 21:
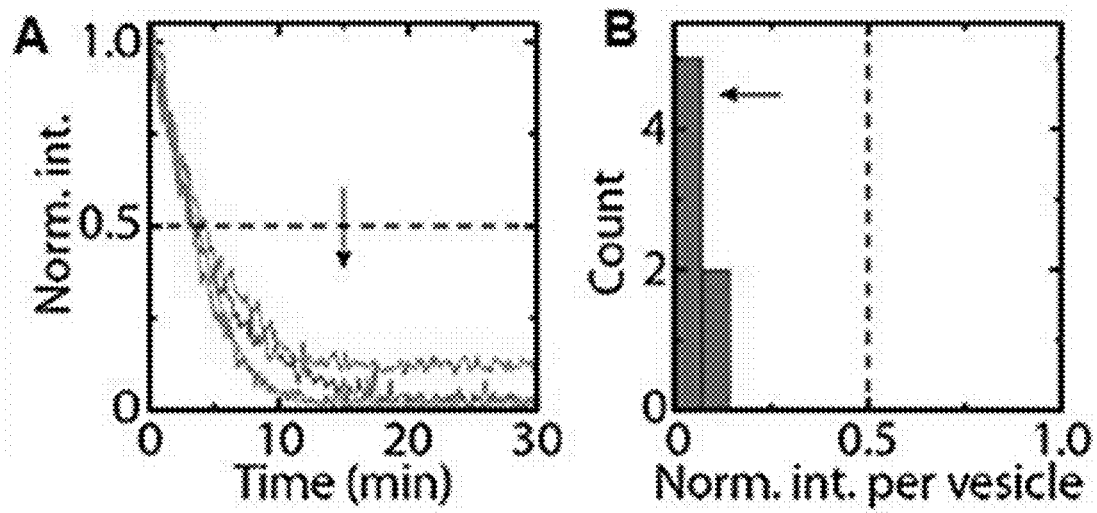
Figure 21:
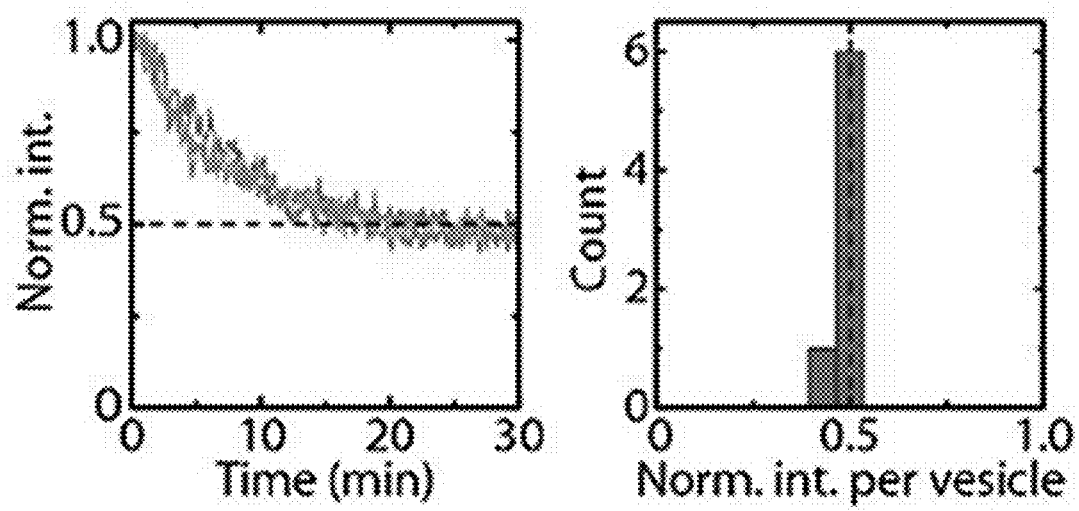

FIG. 21. Graphs showing four representative fluorescence intensity traces of NBD fluorescence reduction over time for both 1C and 2C designs (Panel A). Values have been normalized to the initial intensity per vesicle and aligned to the onset of dithionite reduction. (Panel B) Histograms of residual NBD fluorescence intensity at 35 minutes after dithionite addition normalized to the initial intensity for each vesicle. Data was obtained from four (2C) and one (1C) experiments using the same GUV stock solution (see dithionite quenching assay in methods section below for further details). Black arrows and dashed lines in (panels A and B) highlight the shifted fluorescence intensity values for 2C nanostructures in contrast to the 1C control. Data shown were collected from vesicles with a diameter above 6 μm (for smaller vesicles see FIG. 22).

Figure 22:
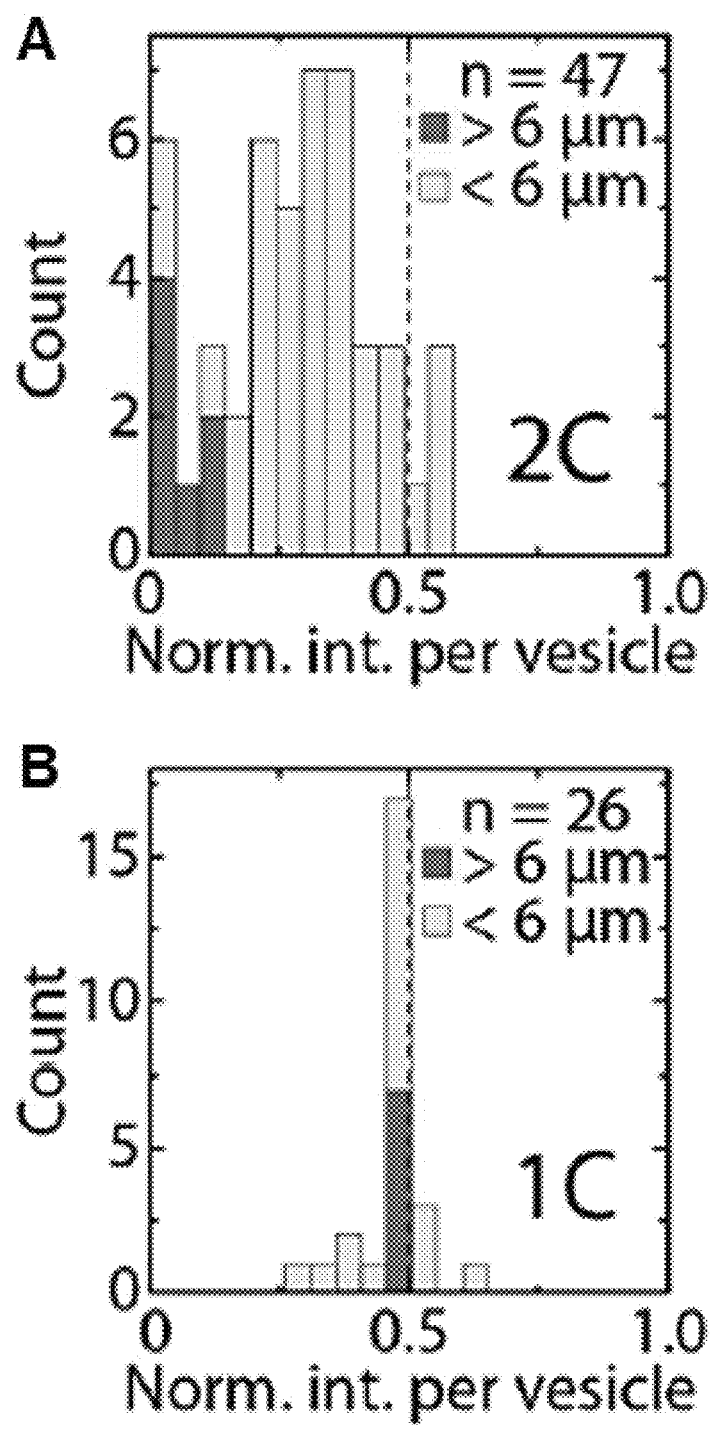

FIG. 22. Histograms of residual, normalized NBD fluorescence intensity at 35 minutes after dithionite addition for vesicles incubated with the 2C (Panel A) or the 1C (Panel B) design. Data for larger vesicles (d>6 μm, green) are the same as presented in FIG. 21, panel B. Additionally, values for smaller vesicles (d<6 μm, gray) are shown. Data were acquired from the same experiments as those described in the caption to FIG. 21, panel B. The smallest vesicle included in the analysis was 2.6 μm in diameter. Almost all vesicles incubated with the 1C design showed a fluorescence intensity reduction to the 0.5 value whereas the majority of vesicles incubated with the 2C design displayed a reduction considerably below the 0.5 value. Bin size is 0.049.

Figure 23:
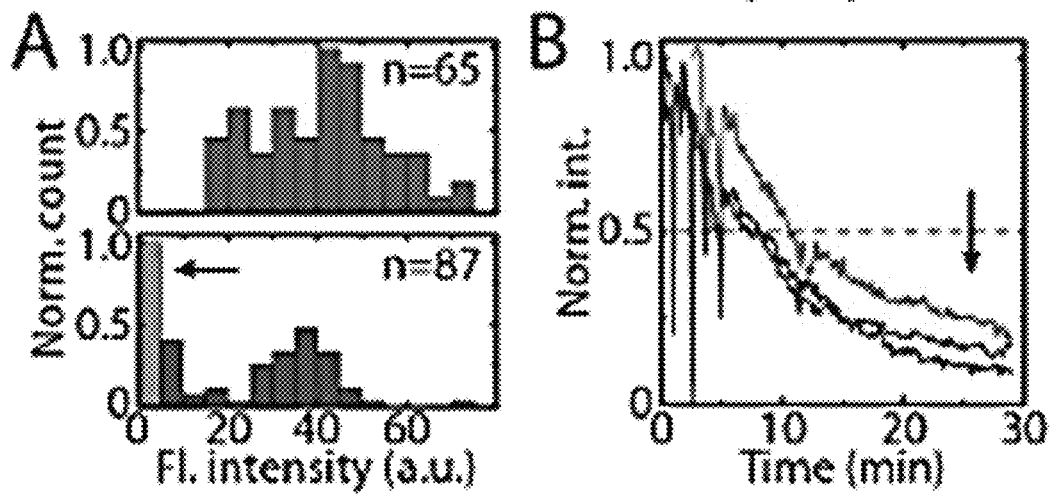
Figure 23:
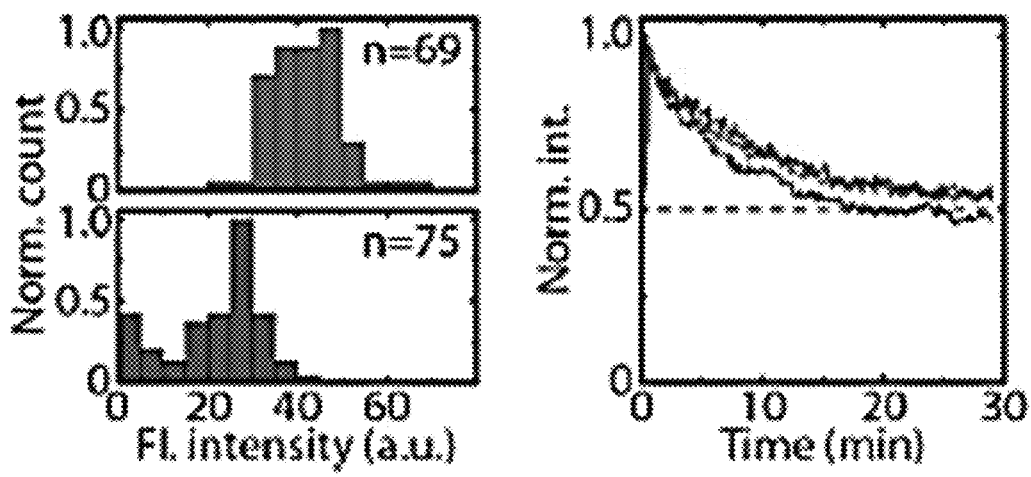

FIG. 23. Results of dithionite reduction experiments performed using an alternative measurement protocol. (Panel A) Absolute NBD fluorescence intensities before (green) and approximately one hour after (grey) dithionite addition. Arrow and red column highlight a shift in the population down to no residual fluorescence intensity. Counts were normalized to the maximum for each histogram. The fluorescence intensity for 2C data has been scaled by the ratio of the average fluorescence intensity before dithionite addition of 2C-incubated vesicles over 1C-incubated vesicles. Number of analyzed vesicles is denoted by n. (Panel B) Exponential reduction of NBD fluorescence from vesicles incubated with 2C and 1C nanostructures. The experiment was performed as described in Table 4 but this time one field of view containing vesicles was imaged every 5 s over time. Fluorescence reduction below 0.5 indicates lipid scrambling. Large intensity spikes are caused by vesicles temporarily not being in focus. The shifted red trace in the top graph is caused by the vesicle entering the field of view only some moments after dithionite addition.

Figure 24:
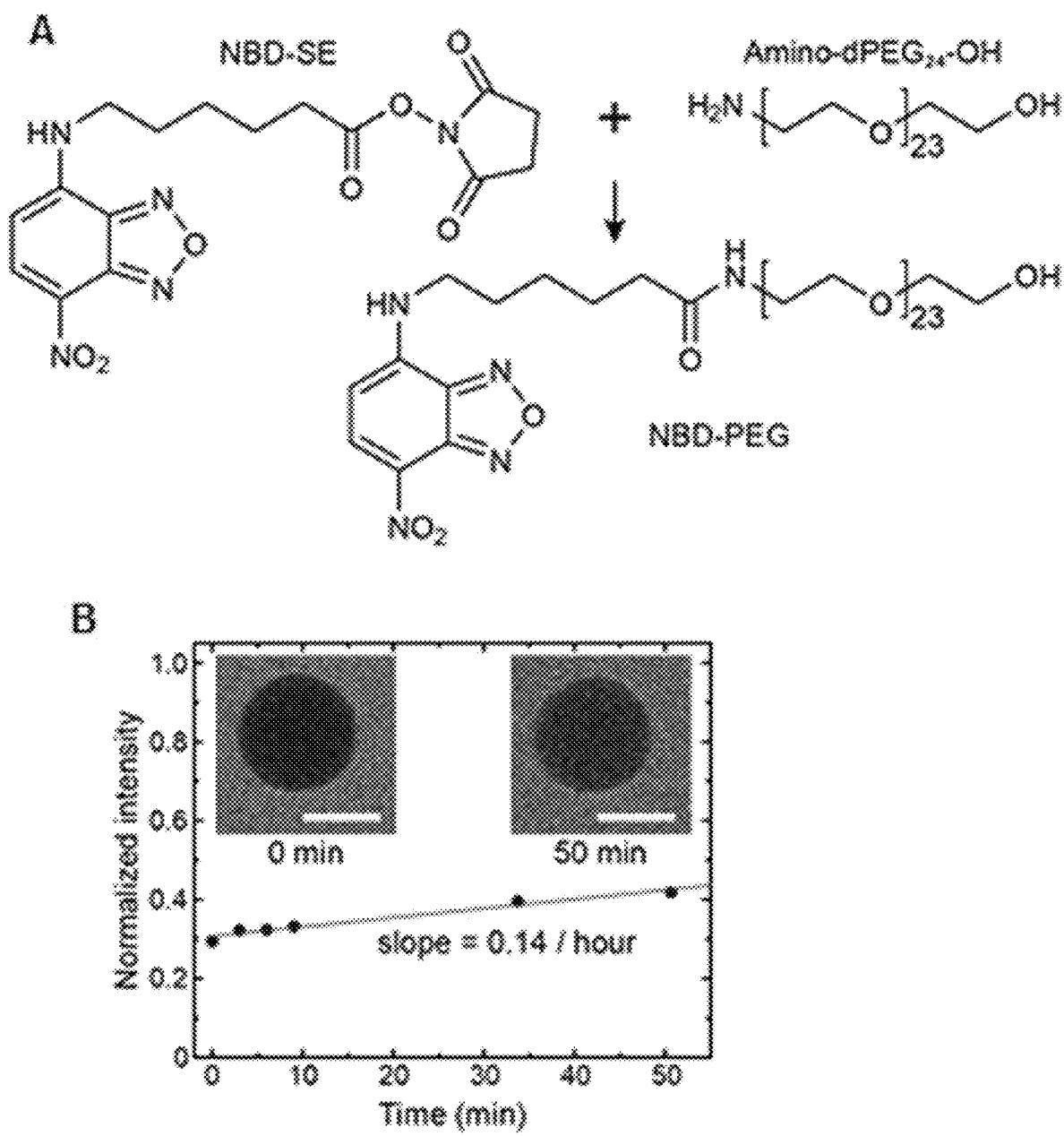

FIG. 24. Synthesis and membrane permeability of NBD-PEG. (Panel A) Chemical structures of succinimidyl 6-(N-(7-nitrobenz-2-oxa-1,3-diazol-4-yl)amino)hexanoate (NBD-SE; Invitrogen), an NHS-ester of the fluorescent dye NBD, an amine-terminated 24-unit polyethylene glycol (PEG24; Quanta Biodesign), and their reaction product NBD-PEG. (Panel B) Insets confocal microscopy images showing the fluorescence intensity directly after NBD fluorophores inside a vesicle were photobleached (0 minutes) and 50 minutes later (scale bars represent 5 μm). The graph displays the recovery of the fluorescence intensity inside the vesicle over time after photobleaching normalized to the intensity outside the vesicle at 0 minutes. Red line represents a linear fit. Its slope of 14% per hour indicates a slight rate of NBD-PEG permeation back into the vesicle.

Figure 25:
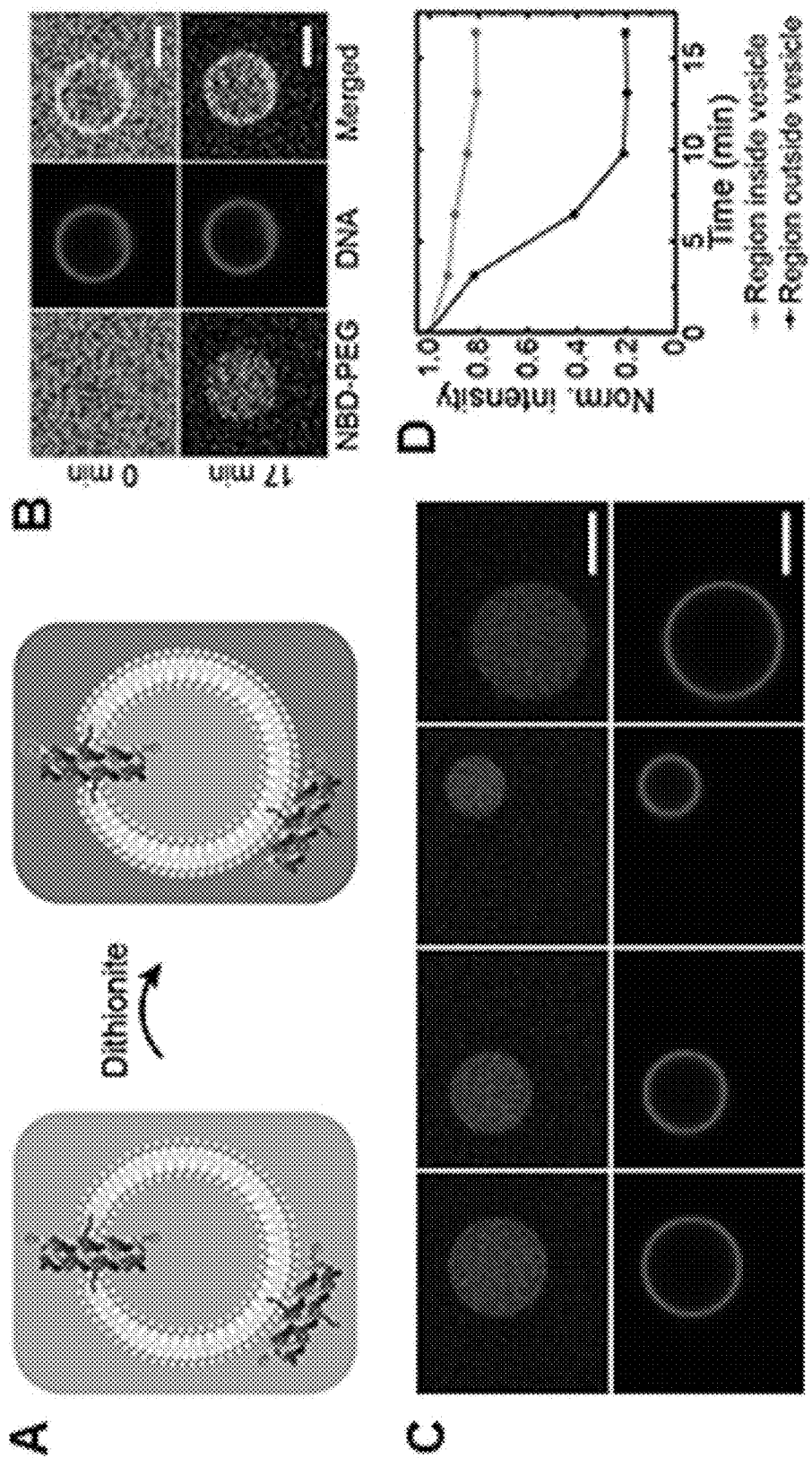

FIG. 25. Dithionite reduction assay performed on GUVs with equal concentrations of NBD-PEG inside and outside vesicles and incubated with 2C DNA nanostructures. (Panel A) Scheme illustrating how addition of dithionite would only reduce the fluorescence of NBD-PEG outside vesicles if 2C DNA nanostructures do not facilitate permeation of dithionite into the vesicles. (Panel B) Confocal fluorescence microscopy images of GUVs incubated with the Cy3-labeled 2C DNA scramblase design (red) and with NBD-PEG (green) in solution at equal concentrations inside and outside the vesicles. (Panel C) Vesicles at other locations within the chamber used in the assay described in B but imaged at time points between 37 and 48 minutes after dithionite addition. Scale bars are 5 μm and the same for all images. (Panel D) Graph showing normalized NBD-PEG fluorescence intensity traces after dithionite addition from regions inside (green) and outside (black) the vesicle displayed in B.

Figure 26:
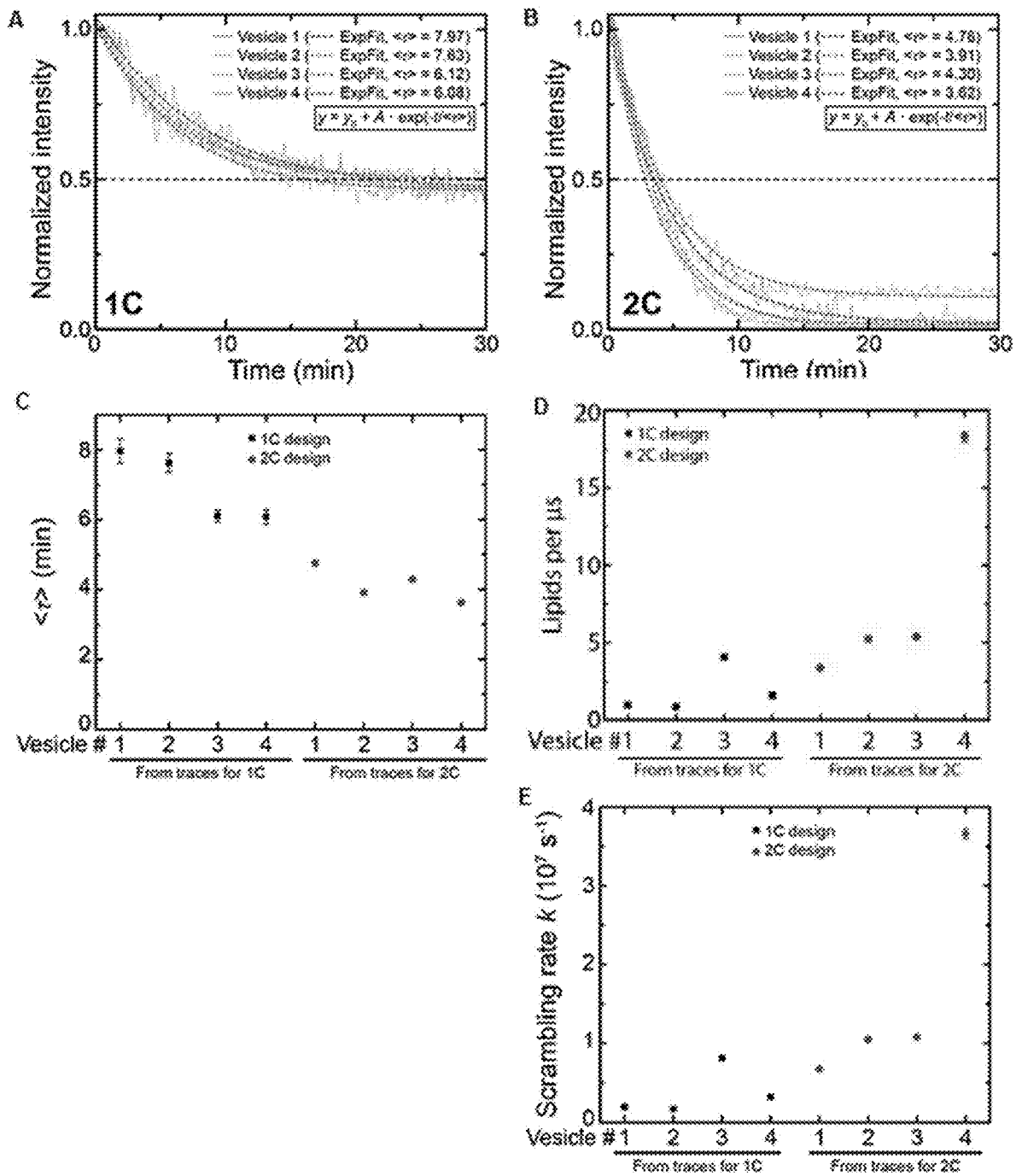

FIG. 26. Dithionite reduction rates determined from experiments. (Panels A and B) Exponential fits (dotted lines) of dithionite reduction traces (solid lines) shown in FIG. 21 for 1C and 2C nanostructures, respectively. Fit values k of decay rates are shown in the legend with the fitting equation below. (Panel C) Graph comparing the fitted normalized decay rates k (error bars denote fitting error) of the different dithionite reduction traces together with their mean±standard deviation for 1C and 2C designs. (Panel D) Decay rates in lipids per μs approximated from normalized rates shown in (Panel C). Using literature values for POPC lipids for Luzzati thickness $D_B$=3.68 nm and area of a lipid A=0.683 nm$^2$, the volume of a lipid can be determined (61). By measuring the diameter of the specific vesicle the total volume of the membrane can be calculated and divided through the volume of a single lipid to obtain the total number of lipids. Normalized rates were only multiplied by the number of lipids per vesicle since simulations showed that the scrambling rate does not depend on the ratio of labeled lipids (see FIG. 18). (Panel E) Scrambling rates approximated from characteristic decay times shown in (Panel C) with error bars originating from error of τ. For scrambling rate calculations, the number of lipids per vesicle without an additional factor was divided by τ since simulations showed that the scrambling rate does not depend on the ratio of labeled lipids (see FIG. 18).

Figure 27:
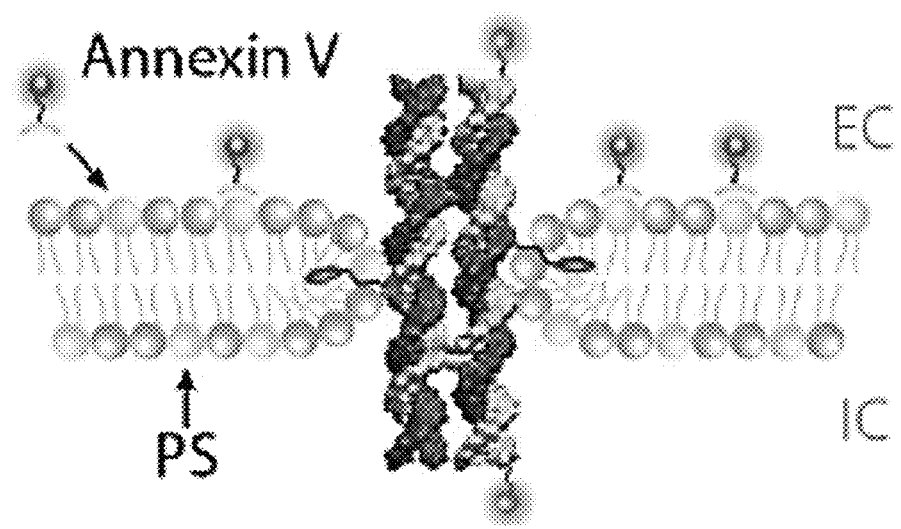

FIG. 27. Schematic illustration of FITC-labeled Annexin V binding assay to assess DNA nanostructure-induced lipid scrambling in human cells via an increased amount of surface-exposed PS lipids (light blue). EC and IC indicate extra- and intracellular volumes.

Figure 28:
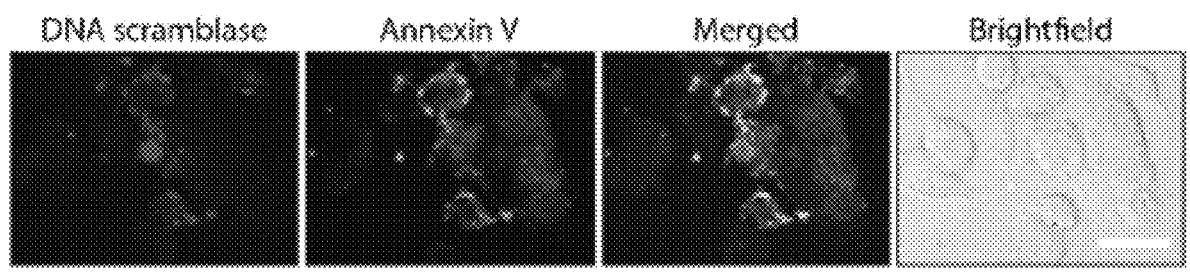

FIG. 28. Confocal microscopy images of fixed cells after incubation with Cy3-labeled DNA scramblases show cell attachment of the DNA nanostructures (red) associated with increased Annexin V (green) binding (see merged signal of both channels). Corresponding brightfield image is shown for reference (scale bar is 20 μm).

Figure 29:
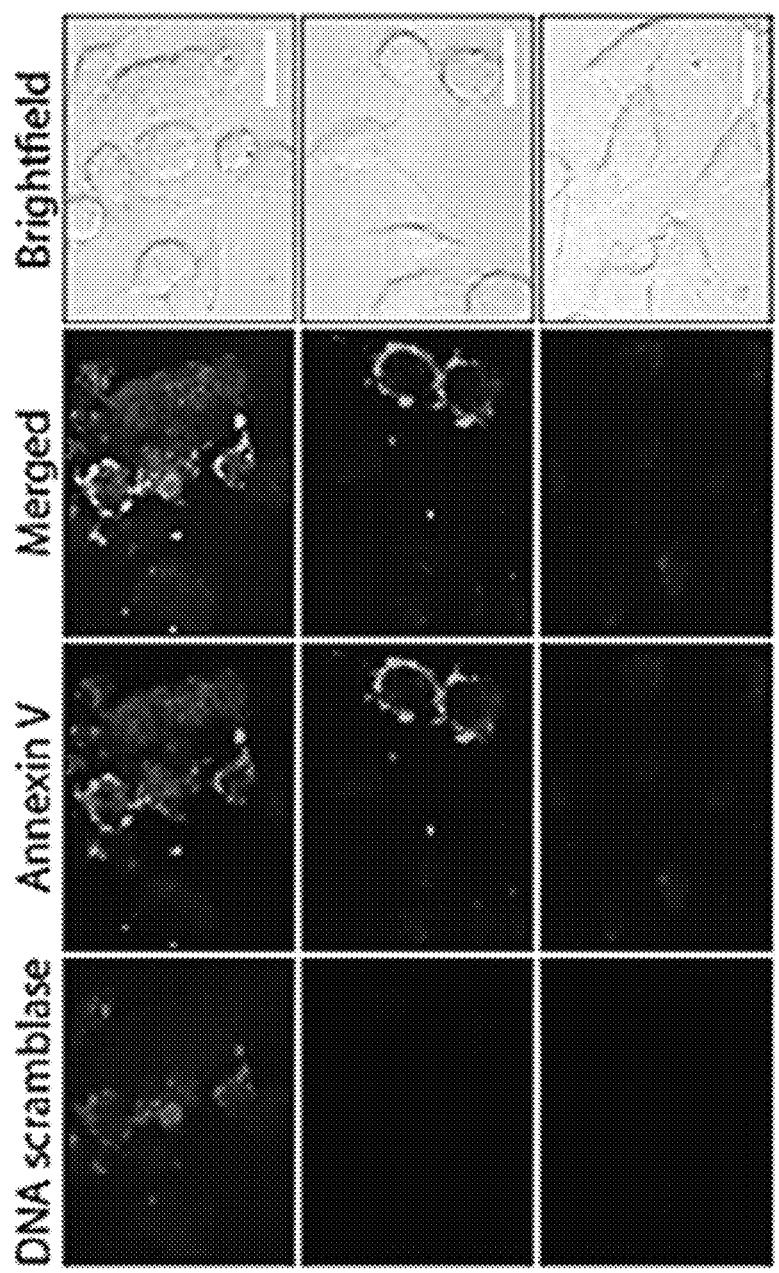

FIG. 29. Schematic illustrations and confocal microscopy images of scrambling experiments in human cells together with two controls. (Panel A) Same experiment and results as shown in FIGS. 27 and 28, but kept for direct comparison to controls. (Panel B) Positive control experiment in which cells were incubated in the presence of 10 μM staurosporine (S5921, Sigma) under the same conditions as performed for DNA scramblases. (Panel C) Negative control experiments in which only 120 μl of the DNA folding buffer used for cell experiments (PBS at pH 7.4 supplemented with 8 mM MgCl$_2$) were added. Cells generally showed very low to no fluorescence intensity in the green channel used to detect Annexin V. No signal was detected in the red channel in (Panels B and C) illustrating sufficient spectral separation of the FITC dye from the Cy3. All imaging settings were the same for the equivalent images in all experiments. Scale bars are 20 μm.

Figure 30:
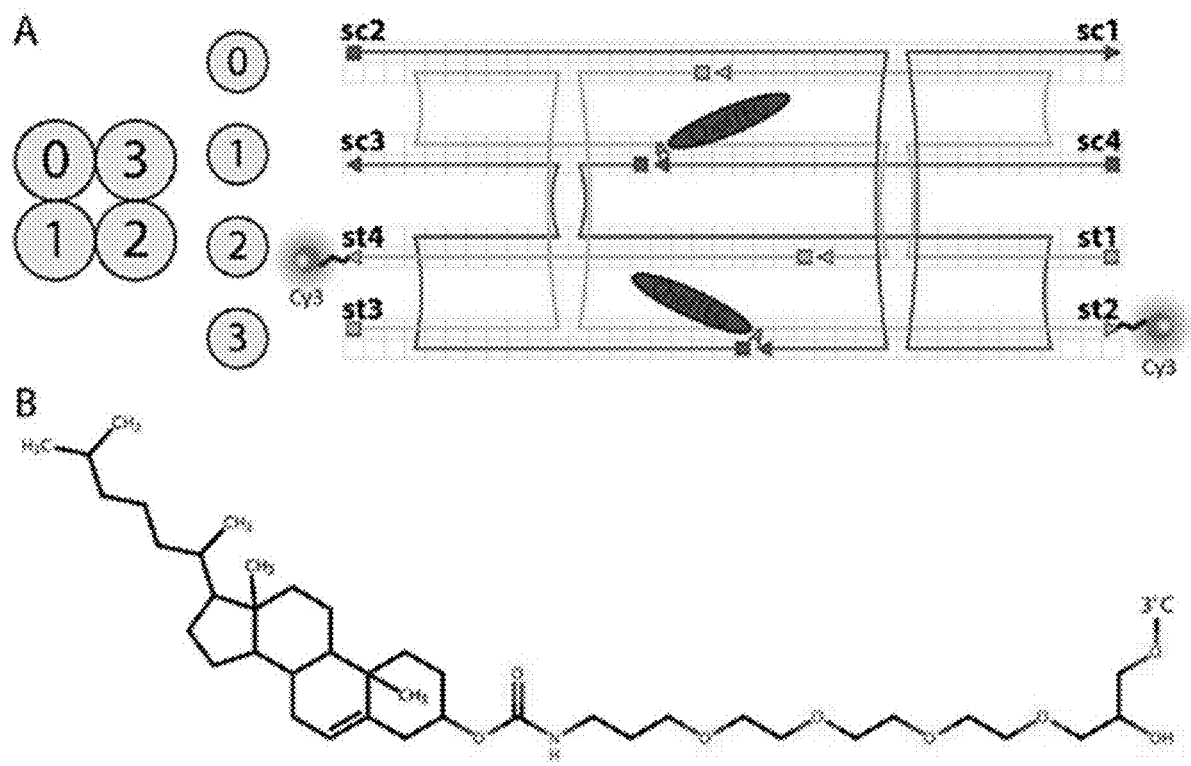

FIG. 30. Chemical architecture of DNA nanostructure. (Panel A) CaDNAno design of the DNA nanostructure. The nucleotide sequence of each strand is listed in Table 1. The"CholTEG" tag indicates a cholesterol group chemically linked to a nucleotide. Cy3-tags were employed for vesicle and cell experiments. (Panel B) Chemical structure of cholesterol group with TEG linker. The "3'C" tag indicates the 3' carbon of the modified nucleotide.

Figure 31:
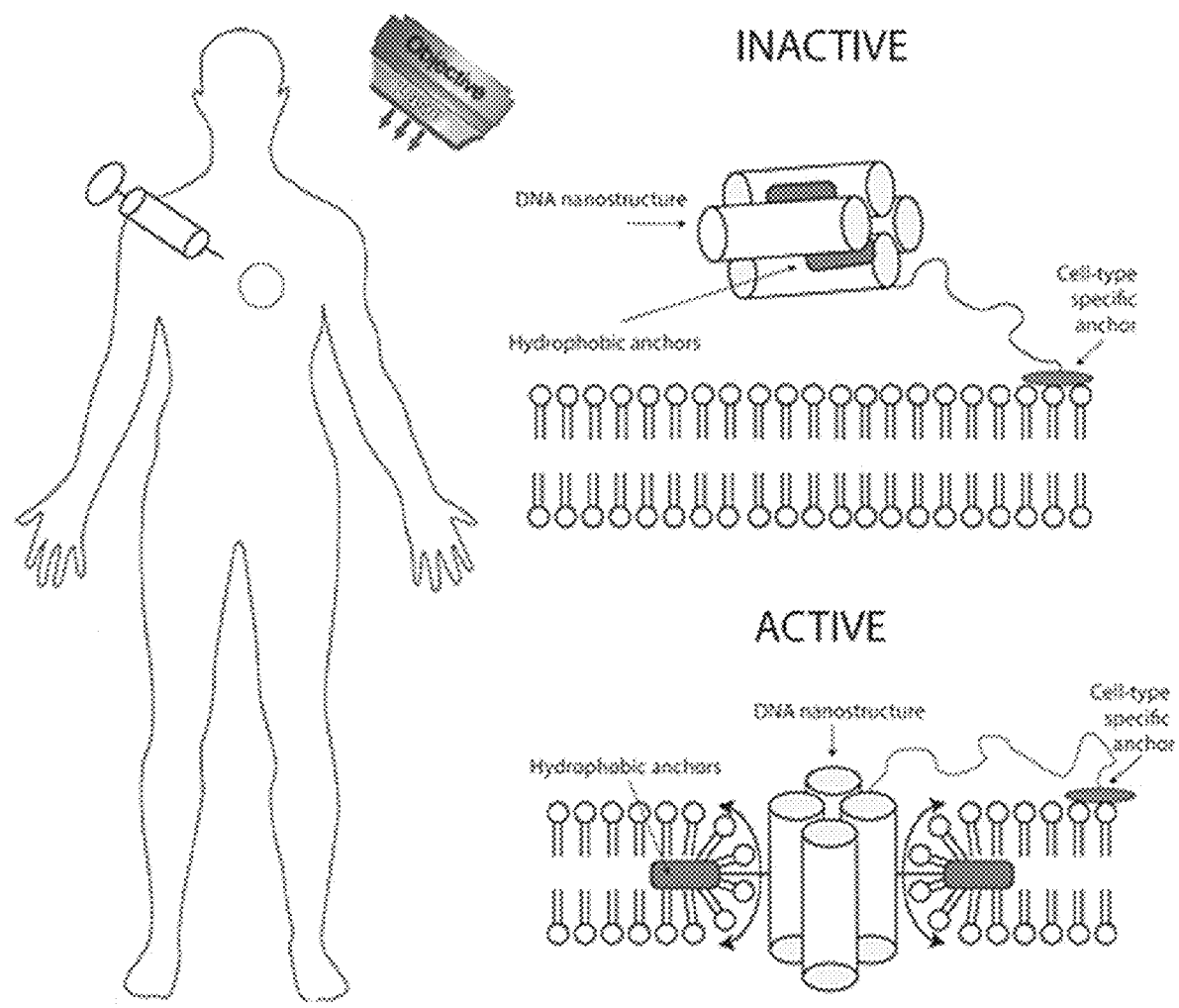

FIG. 31. An overview of one embodiment of how composition can be used. Synthetic DNA, RNA or nucleic acid analogue based scramblase binds specific cell types via a cell-type specific anchor. Upon activation, the DNA scramblase inserts into a cell membrane, where it provides a continuous path for lipids to diffuse from one leaflet of the membrane to the other. Rapid homogenization of lipid composition can be used to alter the biological state of the cells, including inducing a programmed cell death (apoptosis).

Figure 32:
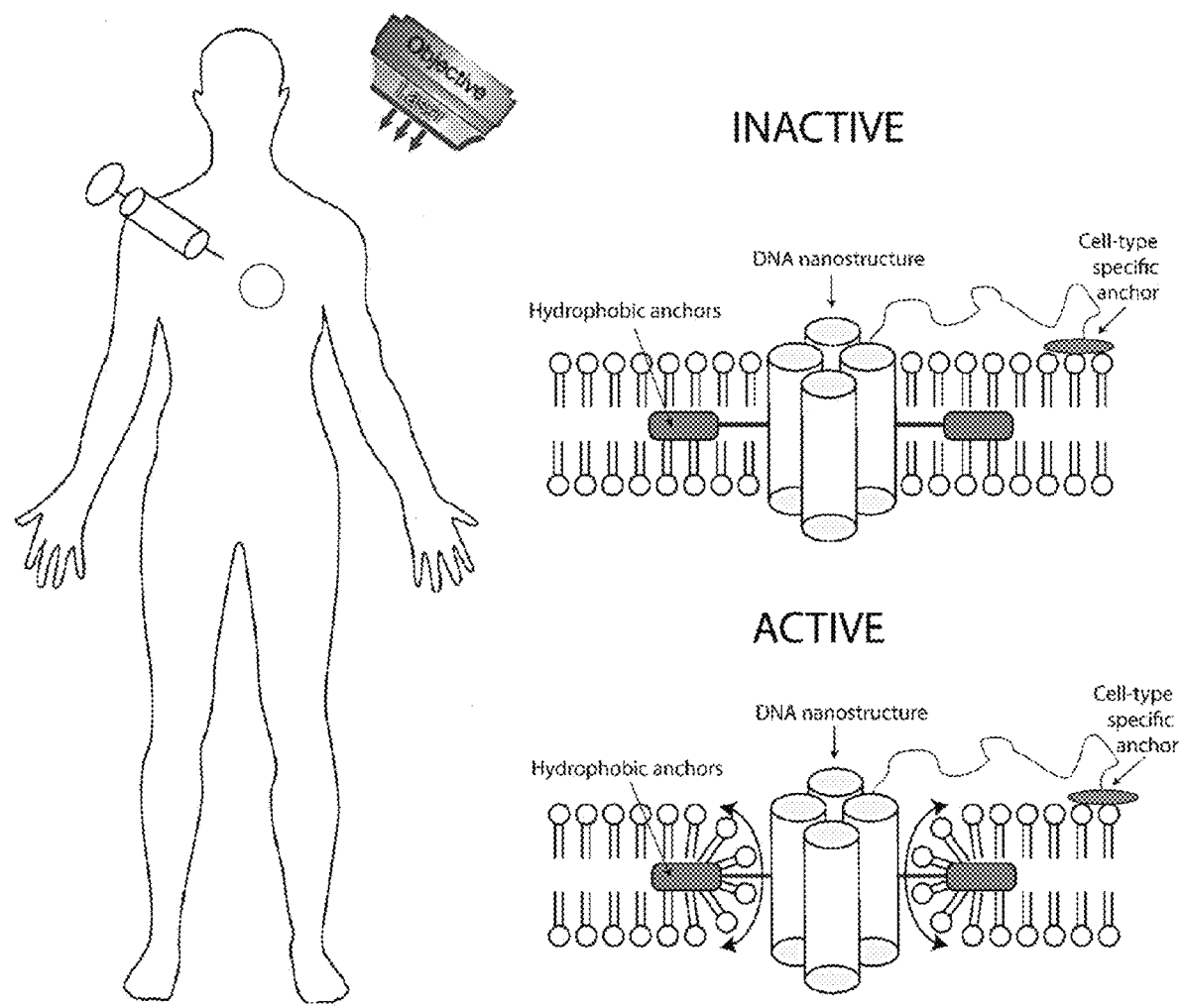

FIG. 32. An overview of an additional embodiment of how the composition can be used. Synthetic DNA scramblase binds specific cell types via a cell-type specific anchor and inserts into a cell membrane. The activation of the DNA scramblase reduces the hydrophobicity of the DNA construct, which produces rearrangement of lipids into a toroidal pore that provide a continuous path for lipids to diffuse from one leaflet of the membrane to the other. Rapid homogenization of lipid composition can be used to alter the biological state of the cells, including inducing a programmed cell death (apoptosis).

Figure 33:
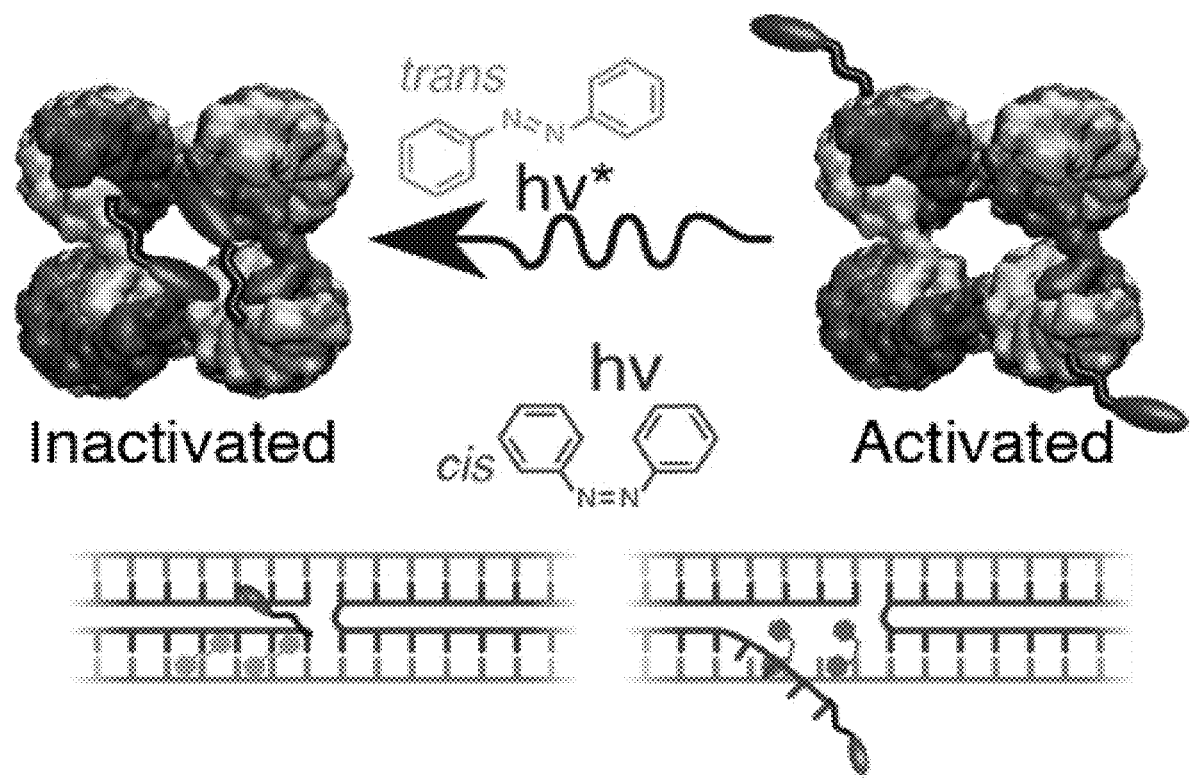

FIG. 33. Light-induced insertion of DNA nanopores. Reversible and controlled by light frying of azobenzene-modified DNA modulates placement of hydrophobic anchors (red) within a DNA nanopore. Placement of the anchors outside/inside the nanopore facilitates its insertion/expulsion from a lipid membrane.

Figure 34:
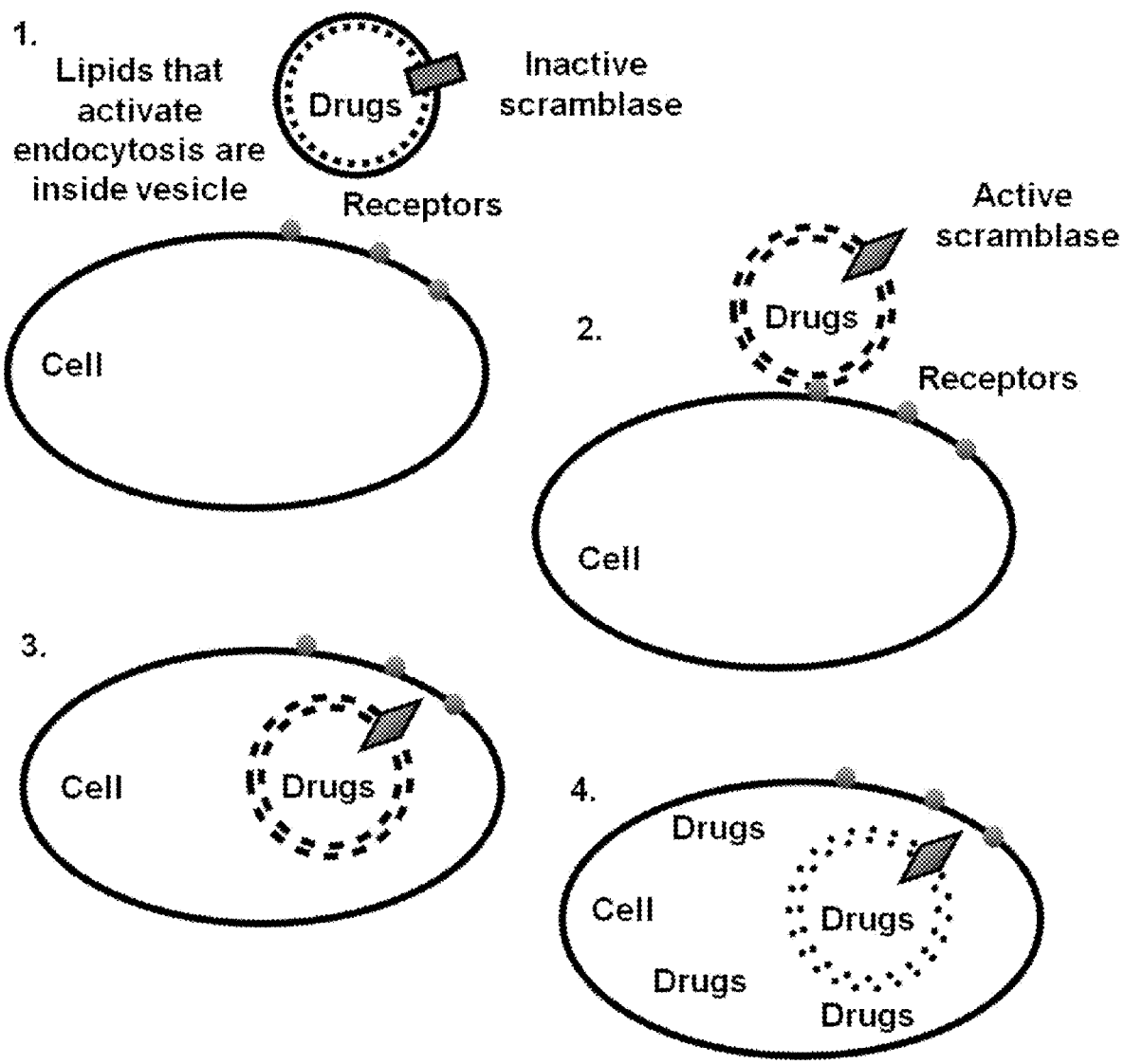

FIG. 34 illustrates a method of using a synthetic scramblase of the present invention to controllably deliver a drug into a cell.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION OF THE INVENTION

The compositions and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Definitions

The term "nucleic acid" or "nucleotide" as used herein, includes DNA, RNA, LNA, PNA, GNA, TNA, PMO, or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

Figure 1:
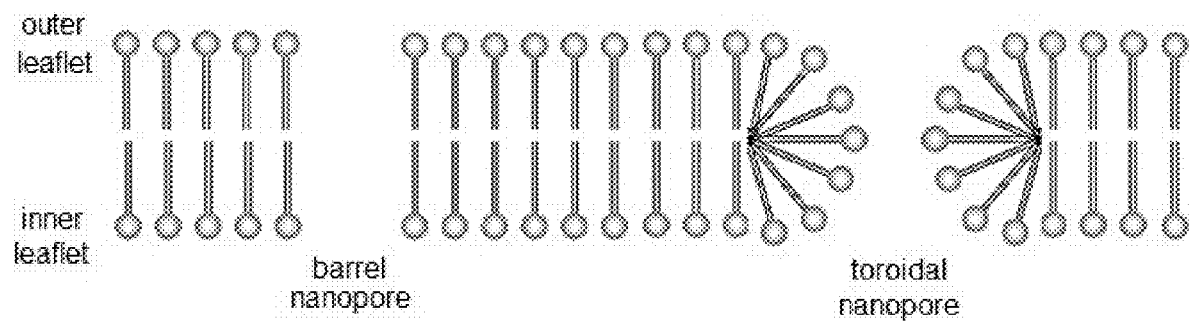
FIG. 1 illustrates a lipid bilayer having a barrel nanopore, such as those cause by conventional transport nanostructres, and a toroidal nanopore formed by the nanostructures of the present invention.

As used herein, a "toroidal pore" refers to a channel or nanopore in a lipid bilayer where the hydrophilic surfaces of the inner and outer leaflets are fused together to form a continuous structure. This is in contrast to nanopores formed by conventional nanostructures, which form a tube or barrel through the bilayer where the hydrophilic surfaces of the inner and outer leaflets do not fuse and remain distinct from one another (see FIG. 1).

The term "nanostructure" refers to structures having one or more dimensions in the nanometer scale range. As used herein, nanometer scale range is meant to include ranges from 0.1 nm to 100 nm. For example, the diameter of a DNA helix is approximately 2.0-2.5 nm.

The term "nanopore" as used herein refers to a pore or channel of approximate nanometer size. With regard to biological membranes, a nanopore can be created by a pore-forming protein or nanostructure. Typical pore-forming proteins or nanostructures contain a hollow core which forms a tube or barrel structure through the membrane.

As used herein, "scrambling" refers to the transfer of phospholipids or other molecules between the two leaflets of a cell membrane, and a "scramblase" refers to a molecule able to transfer the phospholipids or other molecules from one leaflet of a cell membrane to the other.

Overview and Unique Features

Membrane-spanning DNA nanostructures have primarily emerged as synthetic mimics of biological membrane channels (12-20). Critical for lipid membrane insertions of DNA nanostructures was their decoration with hydrophobic anchors (12, 14-20) as the bilayer's hydrophobic core presents a high energetic barrier for DNA (21). However, in contrast to nanopores formed by conventional nanostructures, which form a tube or barrel through the bilayer (71), a toroidal pore will cause the inner and outer leaflets to fuse together (see FIG. 1). This allows for easier transport of lipids within the bilayer to move from one leaflet to the other, and may allow smaller nanostructures to be used. Recently, it has been shown that a porphyrin-modified and membrane-inserted single DNA duplex promotes formation of a toroidal water-filled pore surrounding the duplex (18).

In the examples described below, a DNA-induced toroidal pore was used to design fully functional synthetic scramblases that facilitate rapid mixing of lipids between membrane leaflets. Strikingly, the scrambling activity of the de novo designed DNA-made enzyme outperforms any known biological scramblase by several orders of magnitude. This is remarkable given that the catalytic rates of previous enzymatically active DNA nanostructures fall orders of magnitude below natural benchmarks (22, 23).

Figure 2:
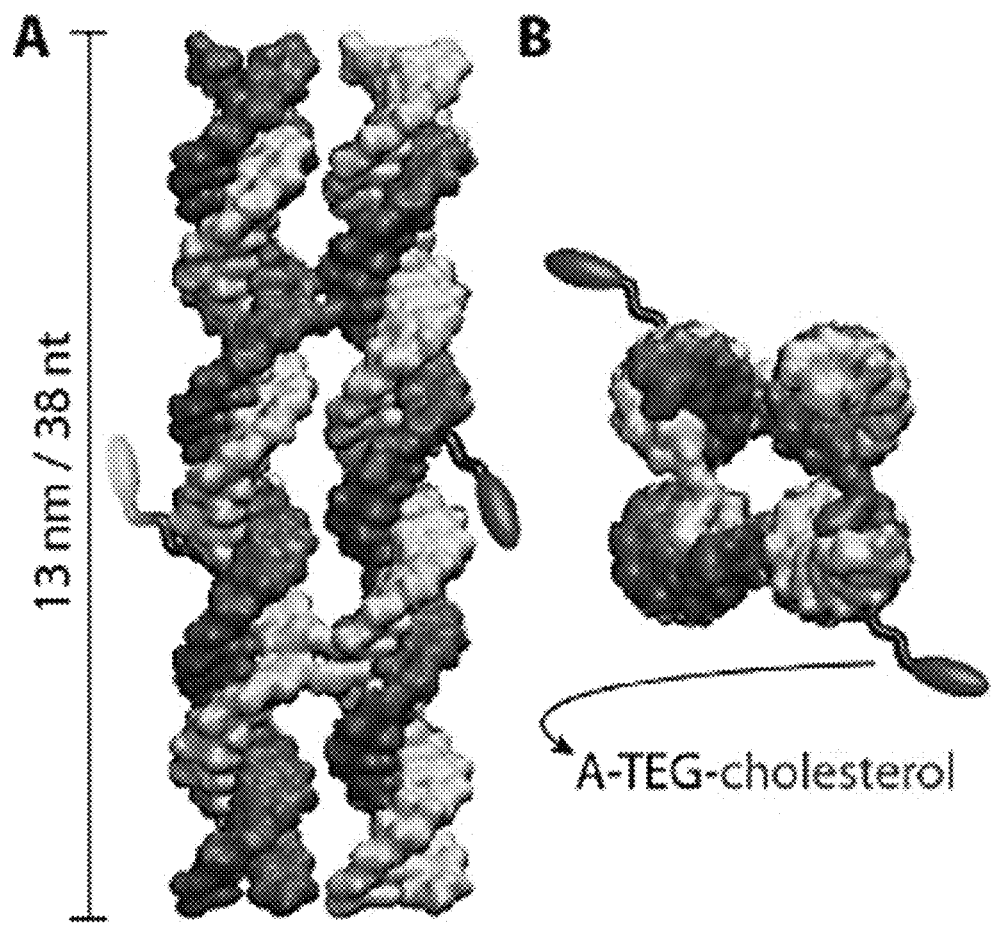
FIG. 2. Design of a lipid-scrambling DNA nanostructure. (Panel A) Side and (panel B) top view of a 3D representation of the assembled DNA nanostructure. Complementary DNA strands are displayed in blue and yellow. Cholesterol modifications (red) at two specific locations are covalently bound to the DNA via an adenine-triethyleneglycol linker (A-TEG, black).

Certain examples describe a DNA nanostructure comprising eight chemically synthesized DNA strands, two of which are modified with a covalently linked cholesterol group on their 3' ends (see FIG. 2 and FIG. 30 for design details as well as Table 1). Diluted in a salt buffer containing $Mg^{2+}$-ions and following a previously described temperature annealing protocol (16), the strands self-assemble into four interconnected DNA duplexes with a designed length of ~13 nm (FIG. 2, panel A). The hydrophobic cholesterol modifications, which are necessary to anchor the charged nanostructures into a lipid bilayer, are strategically positioned in the center of the construct pointing diagonally away from the central pore (FIG. 2, panel B).

Additional synthetic scramblase can be made of any number molecules having hydrophilic regions able to be inserted into a cell membrane including, but not limited to, proteins, carbohydrates, DNA, RNA, and other nucleic acid derived helices. The synthetic scramblase may interact to any other lipid-based membrane of all prokaryotes and eukaryotes. The overall rate of lipid scrambling is controlled by the circumference and chemical composition of the toroidal pore.

In addition to forming a toroidal pore, the synthetic scramblase may or may not contain a central pore. While a synthetic scramblase of the present invention may contain a central pore through the center of its structure, the synthetic scramblases of the present invention are able to facilitate the transport of lipids and other molecules between the leaflets of a cell membrane without use of a central pore. This is in contrast to nanopores formed by conventional nanostructures, such as disclosed in (71).

Figure 3:
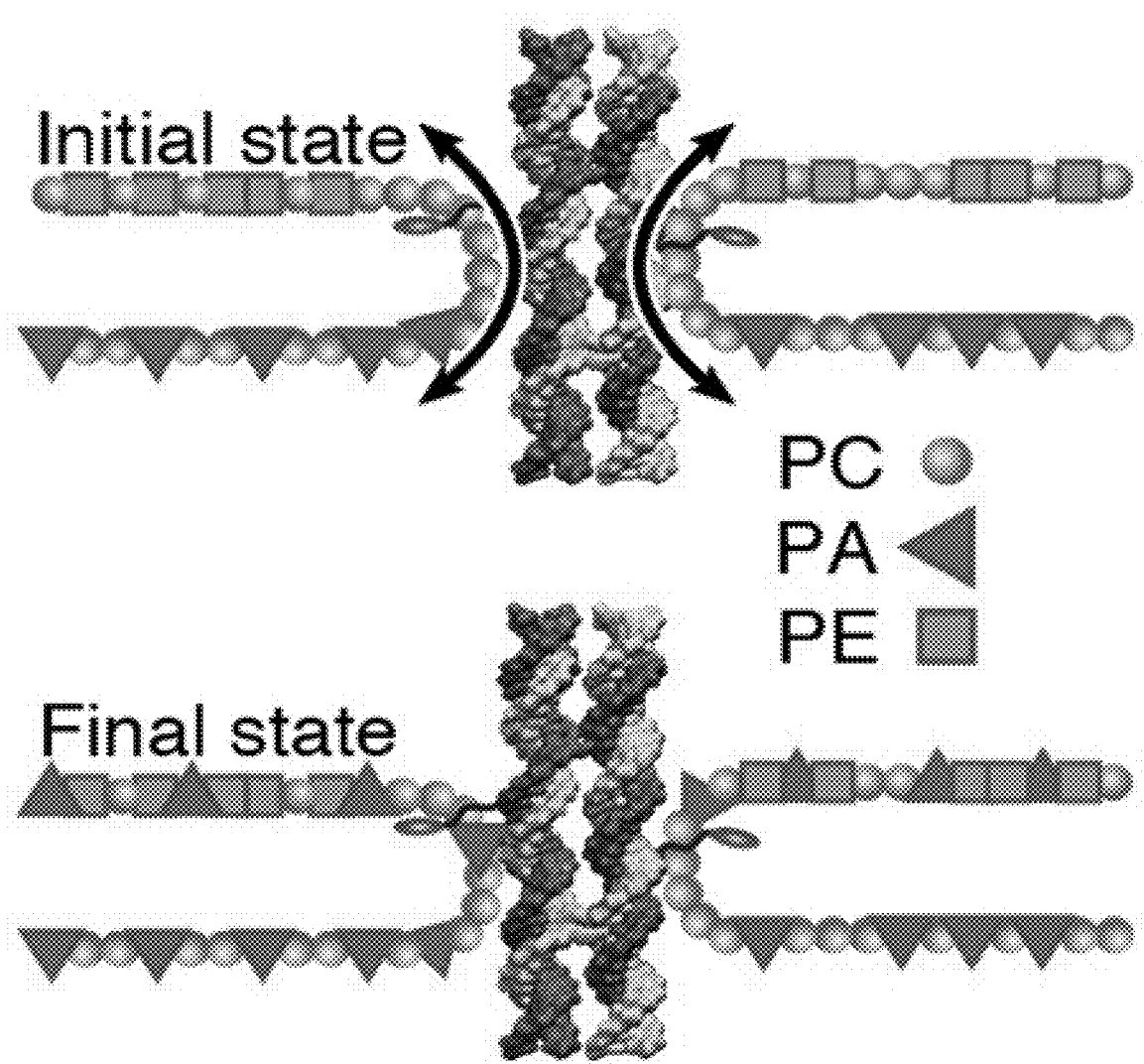

The nanostructure, linker and/or hydrophilic or amphiphilic molecule are also able to be selected in order to selectively transport lipids and other molecules through the toroidal pore. For example, the length of the linker, or the size and/or charge of the hydrophilic or amphiphilic molecule, may allow bulkier lipids or molecules of different charges to more easily move pass the nanostructure from one leaflet to the other. As shown in FIG. 3, a first lipid (PC) is present in both the outer and inner leaflet and is free to pass across the toroidal pore. A second lipid or molecule (PA) is initially present in the inner leaflet of the membrane but is able to pass through the toroidal pore to the outer leaflet. However, a third lipid or molecule (PE) is not able to pass through the toroidal pore due to its size or charge and remains in the outer leaflet.

The synthetic scramblase can be targeted to specific cell types by incorporating chemical labels. The synthetic scramblase can undergo active changes of shape and function, and may be activated by any external or cell internal stimuli or upon binding to the target surface.

The synthetic scramblase can also be used to alter the composition of bacterial cell membranes as well as lipid-based viral envelops, exposing their antigens and making them susceptible to the host immune systems.

When inserted into cancer or intruding cells, the synthetic nanostructures can find applications in cancer treatment and biodefense technologies. Development of synthetic scramblases may also provide a remedy to several medical conditions, for example, Scott syndrome and disorders caused by blood coagulation deficiencies. The present experimental demonstration of lipid scrambling in human cells demonstrates the use of the artificial nucleic acid scramblase in medical applications. In an embodiment, the DNA scramblase is assembled from only eight commercially available nucleic acid strands, thus it can readily be produced in large quantities at low cost. The design is easy to adapt making the targeting of specific cell types straightforward in the future. For applications in personalized medicine, the ease of adaptability and scalability are the two major benefits of the present approach.

The synthetic scramblases also provide a radically new approach to disrupting a cell's homeostasis, a rapid homogenization of the plasma membrane composition, a well-known trigger of programmed cell death or apoptosis.

On demand, target cell-specific lipid scrambling can also aid patients suffering from impaired lipid scrambling or be used to trigger apoptosis of intruder cells, including cells carrying cancer specific plasma membrane antigens. Furthermore, the mechanism of the present synthetic scramblases is independent of any cell-specific apoptosis pathways, making it applicable to a broad range of cell types. Control over lipid homeostasis by synthetic DNA and other nanostructures opens up a yet to be explored direction for designing personalized drugs and therapeutics for a variety of health conditions. Ultimately, the ability to outperform naturally evolved proteins allowed for a glimpse at the tremendous opportunities still to be explored in nucleic acid based nanotechnology.

Rapid scrambling of lipid bilayer membrane compositions by the compositions of the present invention was demonstrated in both simulation and experiment. Experimentally, lipid scrambling induced by a DNA nanostructure was demonstrated in both lipid vesicles (in vitro system) and in human cells. In the case of human cells, experiments have shown the lethal effect of DNA nanostructure insertion originating from lipid scrambling. A system for targeting specific cell types, activation and de-activation of the DNA scramblases and for scrambling lipids of specific types are therefore possible.

The following examples show synthetic DNA nanostructures able to reproduce the biological function of a scramblase protein by inducing mixing of lipids that reside on opposite leaflets of a biological membrane in vitro and in human cells. These synthetic scramblases mix lipids much more rapidly, outperforming both biological and reported artificial scramblases by at least three orders of magnitude (34, 35). Equipped with an activation mechanism and ability to target plasma membranes of specific cell types, the scramblase can be made suitable for biomedical applications with the scrambling activity being controlled by the geometry of the toroidal lipid pore.

EXAMPLES

Example 1. Synthetic Scramblase Built from DNA Nanostructure

Mimicking enzyme function and increasing performance of naturally evolved proteins is one of the most challenging and intriguing aims of nanoscience. The present example employs DNA nanotechnology to design a synthetic enzyme that substantially outperforms its biological archetypes. Consisting of only eight strands, this DNA nanostructure spontaneously inserts into biological membranes by forming a toroidal pore that connects the membrane's inner and outer leaflets. The membrane insertion catalyzes spontaneous transport of lipid molecules between the bilayer leaflets, rapidly equilibrating the lipid composition. Through a combination of microscopic simulations and fluorescent microscopy, the lipid transport rate catalyzed by the DNA nanostructure was determined to exceed $10^7$ molecules per second, which is three orders of magnitude higher than the rate of lipid transport catalyzed by naturally occurring biological enzymes. The results further show that the DNA-based enzyme can control the composition of human cell membranes, which opens new avenues for applications of membrane-interacting DNA systems in medicine.

Experiments with pore-forming peptides determined lipid flip-flop rates between 1 and potentially $10^3$ lipids per second per peptide (64, 65). Recent in vitro experiments on TMEM16 scramblases, opsin, and rhodopsin have assessed lipid flip-flop rates of $>10^4$ s$^{-1}$ per scramblase protein under optimal conditions (25, 26, 28). However, these measured rates were limited by the dithionite-mediated NBD reduction. Recent atomistic simulations of the G protein-coupled receptor opsin determined a characteristic time scale of ~33 µs per lipid translocation event (66). This corresponds to a possible maximum scrambling rate of $3 \times 10^4$ s$^{-1}$ in the case where dithionite is not the rate limiting factor. In contrast, the present experiments found the simulated lipid transfer rate induced by the DNA nanostructure to be in the range of $1.9-2.6 \times 10^7$ s$^{-1}$, up to three orders of magnitude faster than reported for natural scramblases. To achieve flip-flop rates equivalent to natural scramblases the free energy barrier for lipid translocation needs to be lowered from >20 kcal mol$^{-1}$ (uncatalyzed lipid transfer) to ~7 kcal mol$^{-1}$ (67). One reason for the remarkable scrambling rates of the DNA scramblase is the reduction of the free energy barrier to approximately 1 $k_BT$ ($\approx$0.6 kcal mol$^{-1}$ at room temperature), one order of magnitude lower than accomplished by natural scramblases. Furthermore, the DNA-induced toroidal lipid pore is stable for much longer than transient water passages that were previously suggested to mediate spontaneous lipid flipping and flopping (29-42).

The experimentally determined average scrambling rate of ~$1.62 \times 10^7$ s$^{-1}$ matches the simulation results very well, however, these rates can have multiple contributions. While several structures could insert and scramble lipids at the same time, they might only transiently insert and therefore not actively contribute for extended periods. Calculations estimating the mean lifetime T for a freely diffusing phospholipid to encounter a single, immobile flippase have previously been employed to gauge characteristic flipping times assuming every encountered lipid is flipped, and inter-leaflet translocation is not rate limiting (68). Applied to the DNA scramblase embedded in a POPC vesicle with the average diameter of the vesicles used to determine scrambling rates (see FIG. 26), the calculated mean lifetime is 3.6 min, which is only slightly lower than the averaged experimental value of 4.8 min. Furthermore, the scrambling rate defined as the total number of lipids in a vesicle divided by T is calculated as $1.60 \times 10^7$ s$^{-1}$ assuming only a single DNA nanostructure is active, which agrees very well with the simulated and experimentally observed rates (Table 5). These results together with the calculated low energy barrier for lipid translocation suggest, that lipid diffusion in the GUVs is not rate limiting even if only one DNA scramblase is active. If multiple structures scramble lipids simultaneously, a faster fluorescence reduction would be expected but the slow kinetics of the dithionite reduction are ultimately rate limiting.

In summary, the results show that the synthetic DNA nanostructure can reproduce the biological function of a scramblase protein by inducing mixing of lipids that reside on opposite leaflets of a biological membrane in vitro and in human cells. The synthetic DNA scramblase also mixes lipids much more rapidly, outperforming biological scramblases by up to three and reported artificial scramblases by up to six orders of magnitude (67,34,35). These exceptional rates are promoted by a stable DNA-induced toroidal lipid pore directly interconnecting the membrane leaflets without any substrate specificity or covalent bond formation.

Figure 4:
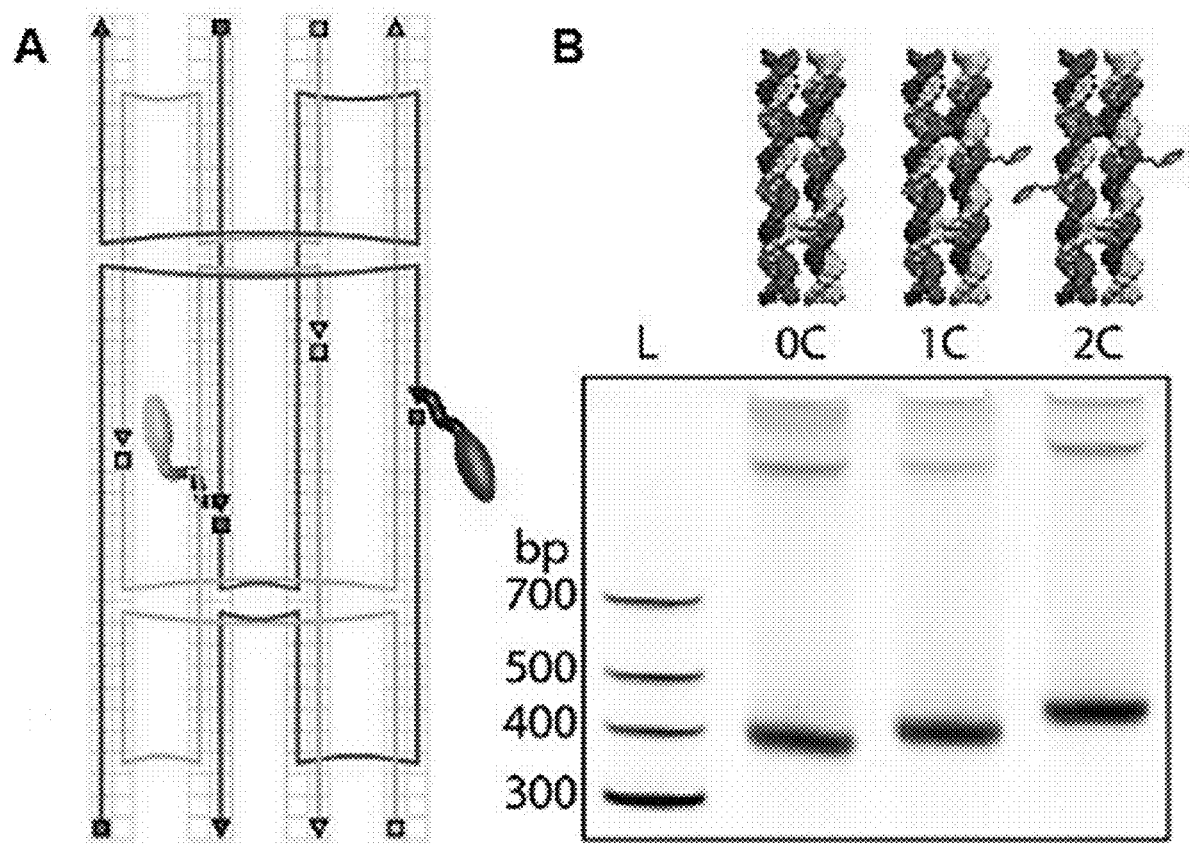
FIG. 4. (Panel A) 2D schematic illustrating the pathway of the DNA single strands as well as crossover and modification positions. Triangles and squares denote the 3' and 5' ends of the strands, and the background grid specifies locations of individual nucleotides. (Panel B) Non-denaturing 10% PAGE of DNA nanostructures annealed without (0C), with one (1C) or with two (2C) cholesterol modifications next to a DNA molecular weight ladder (L). The highest intensity band corresponds to a major population of monomeric structures. The low intensity bands suggest the presence of small amounts of dimers and multimers.

Example 2. Folding and Incorporation of the Hydrophobic Tags into the Nanostructure To verify the folding and incorporation of these hydrophobic tags into the nanostructure, non-denaturing polyacrylamide gel electrophoresis (PAGE) was performed on constructs folded from either eight unmodified DNA strands, or with one or two cholesterol-modified oligonucleotides (FIG. 4, panel B). The gel shows intensity bands that, at the same experimental conditions, shift towards shorter run lengths with every additional cholesterol moiety. The observed shifts are consistent with the increased molecular weight and cross-sections of the modified DNA nanostructures, which confirms their successful assembly and incorporation of the cholesterol tags. PAGE was performed without surfactants, demonstrating that no detergents are necessary to form the monomeric, functional constructs.

Example 3. Determining if Nanostructures could Induce Lipid Scrambling

Figure 5:
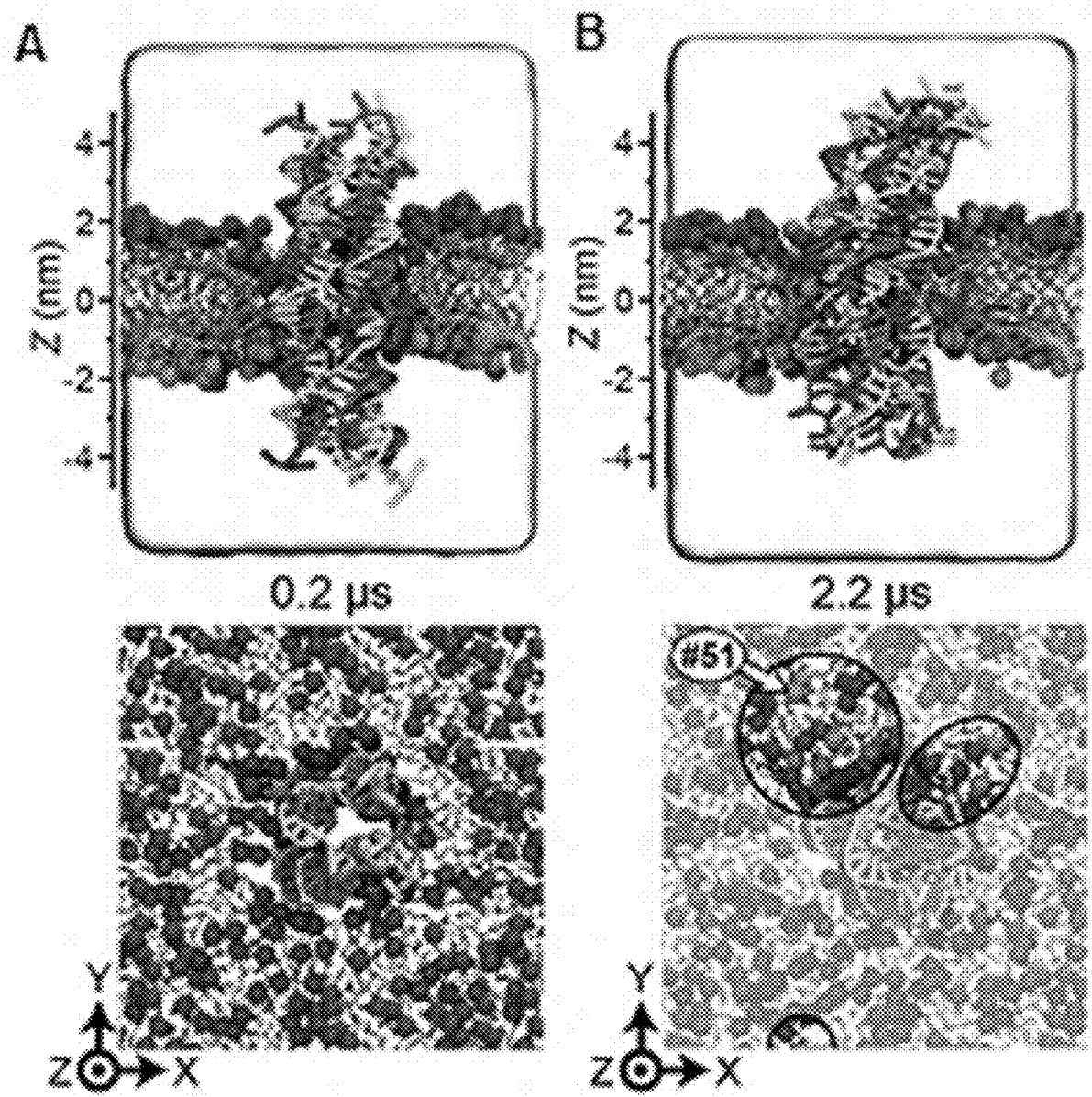
FIG. 5. All-atom MD simulation of lipid scrambling induced by a DNA nanostructure. Microscopic configuration of the simulated system at the beginning (panel A) and the end (panel B) of the free equilibration simulation. Top.

Having experimentally validated the feasibility of folding the cholesterol-modified DNA nanostructures, used the all-atom molecular dynamics (MD) method was used to determine if the structures could induce lipid scrambling when inserted into a lipid bilayer. Following a previously described protocol (18), an all-atom model of the DNA nanostructure embedded in a diphytanoyl phosphatidylethanolamine (DPhPE) lipid bilayer membrane was built and solvated in 1 M KCl. The entire system was first equilibrated for ~230 ns having the DNA nanostructure constrained to its initial idealized conformation, allowing for lipids and water to adopt an equilibrium configuration where the lipid head groups form a toroidal pore around the nanostructure (FIG. 5, panel A; see below detailed description of the simulation protocols). The system was then simulated without any constraints for ~2 μs (FIG. 5, panel B). Comparison of the initial and the final configurations reveals that several lipids have completely transferred from one leaflet to the other through the toroidal pore (FIG. 5, panels A and B; FIG. 6). FIG. 7, panel A, provides examples of inter-leaflet transfer events.

Visual inspection of the MD trajectory revealed diffusion of lipids along the walls of the toroidal pore. The lipids forming the inner surface provide a continuous passage from one leaflet of the membrane to the other. The diffusive motion of individual lipid molecules was not correlated, occurred in both transport directions, and produced zero net transport of lipids from one leaflet to the other, as expected (FIG. 7, panel C).

To quantitatively characterize the inter-leaflet transport of lipids, the Z coordinate of each lipid's phosphorus atoms and its radial distance from the center of the DNA nanostructure, R, were computed as a function of the simulation time (FIG. 8). FIG. 7, panel B, shows an example of a typical translocation, where a lipid molecule is seen to move from the bottom leaflet (Z<−1.75 nm) to the top one (Z>1.75 nm), approaching the DNA nanostructure (R<3 nm) during the transfer process. As the lipid molecule approaches the DNA nanostructure, it reorients itself to expose its polar head group to the DNA nanostructure. Counting an inter-leaflet transfer event each time the Z coordinate of a lipid phosphorus atom moves changes from being less than <−1.75 nm to being more than >1.75 nm or vice versa. FIG. 7, panel C, plots the cumulative number of transfer events versus the simulation time. A linear fit to the cumulative number of transfer events plot yields the average transfer rate of 16.7±0.54 lipids per μs.

A slower yet significant spontaneous transfer of lipids was observed in an additional 2 μs simulation of the same DNA nanostructure embedded in a diphytanoyl phosphatidylcholine (DPhPC) lipid bilayer membrane (FIGS. 9 and 10), suggesting that the rate of lipid transport facilitated by the same nanostructure can be lipid-type dependent. Quantitative analysis of lipid density within the toroidal pore reveals a rather modest, of the order of 1 kBT, free energy barrier to inter-leaflet transport (FIG. 11), which is in accord with the earlier conclusion that transport of lipids occurred via diffusive motion. Given the general character of such transport, any lipid-spanning DNA nanostructures could be expected to exhibit lipid scrambling activity as long as they promote formation of a toroidal pore. Indeed, analysis of previous MD simulations of single duplex and funnel-like DNA pores revealed an average inter-leaflet transport of 4 and 200 lipids per microsecond, respectively (18, 19). In contrast, no lipid scrambling was observed for a DNA nanostructure that had a modified DNA backbone and did not allow the toroidal pore to form (13, 60).

To accurately determine the rate of lipid scrambling and its dependence on the pore-to-lipid ratio, a coarse-grained Brownian dynamics (BD) representation of the toroidal pore surrounding a DNA nanostructure was constructed. In the BD model, the head groups of the lipids are represented by point particles (beads) whereas the presence of all other components of the system, including the DNA nanostructure, the lipid tail, and the electrolyte solution, are modeled implicitly. The bead-bead interaction is described by a short-range repulsive potential (FIG. 12); the diffusivity of each bead depends on its radial distance from the center of the nanostructure (FIG. 13); a 3D potential confines the motion of the beads to the volume accessible to the lipid head groups in all-atom simulations (FIG. 14). FIGS. 15-16 provide detailed description of the simulation methods and its validation against the results of all-atom simulations FIG. 17 illustrates the distribution of the lipid head groups at the beginning and after 48 μs of a BD simulation. A significant proportion of the beads migrated from one leaflet to the other, through the toroidal pore.

FIG. 18 shows the Z coordinate of two representative beads in BD simulations of the system containing a lipid patch L=24 nm on side. Using the same definition of an inter-leaflet transfer event as in the analysis of the all-atom MD simulations, one can identify five transfer events in FIG. 18, panel A. Defining the time interval between two consecutive transfer events as T and taking all lipid head groups into account, a normalized probability of observing a transfer event was obtained (FIG. 18, panel B). The result can be fitted by an exponential distribution $e^{(-t/\tau)}/\tau_o$, yielding the average transfer rate, $1/\tau_o$, of $23\pm1$ $\mu s^{-1}$.

To determine the rate of lipid scrambling k from BD simulations, the number of lipids that have never ventured to the other leaflet as a function of simulation time was counted and fit the resulting dependent by a single exponential function $e^{-kt}$ (FIG. 18, panel C). As expected, the scrambling rate k depends on the system size: faster scrambling is observed for smaller lipid-patch systems in the presence of the same DNA nanostructure.

In an experiment, a low fraction of fluorescently labeled lipids is used as tracers to assess lipid scrambling as described below. In simulations such selective labeling is mimicked by randomly choosing 1% of all lipid heads (1 and 6 beads for L=12 and 24 nm system, respectively) to represent the modified lipids. The number of labeled lipids remaining in their original membrane leaflet decreased in discrete steps (dashed lines in FIG. 18, panel C), however, when averaged over all possible realizations, the decay curve yielded the same average scrambling rate as when all lipid trajectories were used for the analysis.

Example 4. Dependence of the Lipid Transfer and Scrambling Rates on Pore Density To elucidate the dependence of the lipid transfer and scrambling rates on the pore density, the BD simulation were repeated for lipid patches of various dimensions (L=12, 16, 20, 24 and 36 nm, Table 2) containing the same toroidal pore. The lipid transfer rate, FIG. 18, panel D, does not exhibit a strong dependence on the lipid patch size, which was characterized using the pore-to-lipid ratio r computed using the average number of lipids in one of the leaflets of the membrane. The scrambling rate decreases with r (FIG. 18, panel D). The following simple mathematical expression $k=r/<\tau_o>$, where $1/<\tau_o>$ is the system-size averaged transfer rate, reproduces the simulated scrambling rate. Thus, for the range of systems studied using the BD approach, lipid diffusion toward the toroidal pore does not limit the rate of lipid scrambling.

Example 5. Scrambling Activity

Following the computational characterization, scrambling activity was experimentally measured using a dithionite reduction assay (24-26) adapted to giant unilamellar vesicles (GUVs) that were made via electroformation from 2-Oleoyl-1-palmitoyl-sn-glycero-3-phosphocholine (POPC). Trace amounts of phosphatidylcholine were labeled with a nitrobenzoxadiazole (NBD) fluorophore (FIG. 19). Upon addition of sodium dithionite ($Na_2S_2O_4$), the membrane-impermeable anion dithionite ($[S_2O_4]^{2-}$) reduces the NBD fluorophores irreversibly. If no lipid scrambling occurs, only NBD in the outer leaflet of the vesicle membrane is bleached, effectively reducing the fluorescence intensity to 50%. If the DNA nanostructure is present and inserted, lipids can migrate from the inner leaflet to the outer where they would be quenched by dithionite resulting in the reduction of the fluorescence below 50% over time.

POPC lipids are ideally suited for dithionite reduction assays as they show negligible rates of spontaneous flip-flop in reconstituted vesicles (half times >1000 h) and their fatty acid tails are the most abundant in naturally occurring lipid mixtures, classifying them particularly representative for biological membranes (62). Furthermore, POPC lipids minimize the differences in lipid tail chemistry between the vesicle-forming lipids and the NBD-labeled PC tracer lipids making the tracer lipids a more accurate representation of the bulk mixture. The advantage of using GUVs is that they can be observed via fluorescence microscopy, which allows lipid scrambling to be directly verified at the single vesicle level. At the same time, the correlation of scrambling was able to be confirmed with the design and attachment of the DNA nanostructures.

In a microscope chamber, the vesicles were incubated in the presence of 100 nM of folded 2C DNA nanostructures at a physiological pH of 7.4 and left to settle down due to a density gradient between intravesicular sucrose and extra-vesicular glucose. The design of the DNA nanostructures was identical to the simulated model apart from added Cy3-labels that enabled fluorescence visualization (FIG. 19 and FIG. 30). After incubation, vesicles were imaged using confocal fluorescence microscopy. A fluorescent ring was observed in both the NBD and the DNA channel (FIG. 19, panel B, top). Their co-localization (see merged image in FIG. 19, panel B) demonstrates successful attachment of DNA nanostructures to the lipid vesicles (16, 18, 19).

After focusing on one field of view and establishing the initial intensity of NBD and DNA signals separately, dithionite solution was added (4.5 mM final concentration) while recording both channels over time. Care was taken not to move vesicles during the dithionite addition, and the buffer conditions were optimized to avoid significant osmotic pressure (FIG. 20 and Table 3). FIG. 19, panel B shows fluorescent images of one vesicle incubated with 2C nanostructures taken before and approximately 35 minutes after dithionite addition. The NBD signal has completely vanished suggesting that the DNA nanostructures successfully induced lipid scrambling so that inner-leaflet NBD-lipids could migrate to the outer layer where they were reduced by dithionite extinguishing any NBD fluorescence. As the DNA signal was unaffected by dithionite and the nanostructures still remained attached, the fluorescence intensity in the DNA channel could be used to localize the vesicle membrane despite the complete loss in fluorescence in the NBD channel. This enabled the acquisition of intensity traces of different vesicles over time, all showing an exponential decrease in fluorescence to almost zero (FIG. 21, panel A, top graph). About half an hour after dithionite addition all larger vesicles (d>6 μm) displayed a reduction in fluorescence of over 87% with an average residual fluorescence of only ~5±4% (n=7, FIG. 21, panel B, top graph). Thus, the designed DNA nanostructures can induce lipid scrambling in biological membranes. Smaller vesicles (d<6 μm) also showed a significant intensity reduction (FIG. 22, panel A). Over all experiments, more than 85% of vesicles incubated with the 2C nanostructures showed an intensity reduction indicative of lipid scrambling.

As a straightforward control experiment, the same DNA nanostructure was employed containing only a single cholesterol tag (1C, FIG. 19, panel A, bottom). This control construct would still attach to the lipid vesicles, but membrane insertion and lipid scrambling are excluded with no other difference in experimental conditions. Similar to the 2C design, incubation of vesicles in the presence of 1C nanostructures resulted in a fluorescent ring in the DNA channel before and after dithionite addition (FIG. 19, panel B, bottom) indicating membrane attachment. However, the NBD fluorescence intensity after 35 min remained at about 50% indicating the absence of scrambling activity. Example fluorescence intensity traces (FIG. 21, panel A, bottom graph) show the expected exponential decrease plateauing at 48±1% (n=7, FIG. 21, panel B, bottom graph, and FIG. 22, panel B). Thus, only the outer-layer lipids have been bleached by dithionite as the 1C DNA nanostructures could not insert into the membrane and induce lipid scrambling. Another independent set of experiments for the dithionite reduction assay confirmed the difference in the scrambling activity of the 1C and 2C designs (FIG. 23).

As DNA is negatively charged, permeation of anions through DNA-induced lipid pores is expected to be much slower than cation permeation due to electrostatic repulsion. Simulations of a larger, membrane-inserted DNA nanostructure showed significantly decreased Cl– ion over K+ ion permeation (60). In accordance with these results, the performed all-atom simulations on the DNA scramblase design similarly reveal a 93% reduction of Cl– ion permeation compared to that of K+ ions. In the dithionite reduction assay, the NBD-reducing dithionite anion $[S_2O_4]^{2-}$ is larger than Cl– ions and, most importantly, it is twice negatively charged. Therefore, the negative charge of the DNA nanostructure, in combination with an overall low ionic strength of the buffer solution used in the experiments, is expected to present a barrier to dithionite permeation through the toroidal pore.

To demonstrate the low permeation rate of dithionite through the DNA-induced toroidal pore, a series of control experiments were performed. According to a previously described protocol (63), a fluorescent probe was synthesized from NBD and a 24-unit polyethylene glycol (NBD-PEG; FIG. 24, panel A), and encapsulated in POPC vesicles. Dried NBD-SE and PEG24 were each diluted in 1:1 chloroform:methanol to final concentrations of 10 mg ml-1 (≈25 mM) and 137 mg ml-1 (≈128.3 mM), respectively. For the reaction, 100 µl NBD-SE and 20 µl PEG24 were mixed with 380 µl 1:1 chloroform:methanol and incubated for one hour at room temperature under constant movement. The solution was then blow-dried with nitrogen, desiccated for 10 minutes under vacuum and subsequently dissolved in 500 µl of 20 HEPES (pH 7.4) for a final concentration of ≈5 mM NBD-PEG.

POPC vesicles were prepared as otherwise described herein except that the dried lipids were hydrated in sucrose buffer containing 70 µM NBD-PEG. Vesicles were diluted in glucose buffer as used for dithionite reduction assays but supplemented with 70 µM NBD-PEG and incubated for two hours with 2C DNA nanostructures. Insets confocal microscopy images showing the fluorescence intensity directly after NBD fluorophores inside a vesicle were photobleached (0 minutes) and 50 minutes later (scale bars represent 5 µm) (FIG. 24, panel B). The graph displays the recovery of the fluorescence intensity inside the vesicle over time after photobleaching normalized to the intensity outside the vesicle at 0 minutes. Red line represents a linear fit. Its slope of 14% per hour indicates a slight rate of NBD-PEG permeation back into the vesicle. Analogous experiments performed with 2-(N-(7-nitrobenz-2-oxa-1,3-diazol-4-yl) amino)-2-deoxyglucose (2-NDB-glucose; Invitrogen) yielded a full recovery of the fluorescence intensity inside the vesicle at time scales ≈10 minutes demonstrating comparatively rapid membrane permeation The covalent attachment of the PEG chain was expected to increase the hydrodynamic radius of the NBD dye, preventing its direct permeation through the membrane and through DNA-induced toroidal pores. After incubation of these vesicles with the 2C DNA scramblases, NBD dyes inside the vesicles were photobleached. Measurements of the fluorescence recovery showed that, at the time scale relevant for the dithionite reduction assay, the synthesized NBD-PEG molecules are essentially membrane-impermeable (FIG. 24, panel B). The same batch of vesicles was then incubated with DNA scramblases, again with NBD-PEG molecules present inside and outside the vesicles.

A dithionite reduction assay was carried out following the same protocol as in the lipid scrambling assays but with a final concentration of 70 µM NBD-PEG also present outside the vesicles. DNA nanostructures were continuously imaged every 10 s whereas NBD-PEG was imaged intermittently every 200 s (=every 20th frame). FIG. 25, panel A illustrates how addition of dithionite would only reduce the fluorescence of NBD-PEG outside vesicles if 2C DNA nanostructures do not facilitate permeation of dithionite into the vesicles. FIG. 25, panel B shows confocal fluorescence microscopy images of GUVs incubated with the Cy3-labeled 2C DNA scramblase design (red) and with NBD-PEG (green) in solution at equal concentrations inside and outside the vesicles. The same vesicle is shown before and 17 minutes after dithionite addition. The third column displays a merged image of the red and green channels. Scale bars are 5 µm and the same for all images.

FIG. 25, panel C shows vesicles at other locations within the chamber used in the assay described in B but imaged at time points between 37 and 48 minutes after dithionite addition. Monitoring NBD-PEG fluorescence showed that the fluorescence outside the vesicles was rapidly decreased whereas the fluorescence inside the vesicles remained almost constant over the 45-minute time scale of the measurement (FIG. 25, panels B-D). These experiments show that dithionite permeation through the DNA-induced pores is too slow to explain the rapid decrease in fluorescence observed in the 2C DNA scram blase experiments.

The above experimental results establish that the DNA nanostructure acts as a lipid scramblase in biological membranes at physiological pH values in vitro and that an alternative design, not capable of membrane insertion, does not produce lipid scrambling. Traces for both 1C and 2C structures shown in FIG. 21, panel A, are well described by a single exponential decay (FIG. 26, panels A and B), which is in agreement with a previous characterization of fully activated biological scramblases that found the dithionite reduction of the NBD dye to be the rate limiting factor in the case of rapid scrambling (26). Approximating the number of lipids per vesicle, the overall scrambling rates per vesicle were calculated to be between ~3 to 18 lipids per µs (FIG. 26, panel D) and the overall scrambling rates per vesicle were calculated to be ~0.7-3.7×10$^7$ s$^{-1}$, which is in good agreement with the simulated scrambling rates of individual DNA scramblases. Furthermore, as the dithionite solution was added very carefully to not move the vesicles, the observed rates also include the effects of dithionite diffusion toward the vesicles.

The highest reported lipid scrambling rate in human cells was $7.8 \times 10^{-2}$ s$^{-1}$ measured in platelets (27). Previous in vitro experiments on TMEM16 scramblases (26), opsin (25), and rhodopsin (28) determined the scrambling rates at $10^4$ s$^{-1}$ under optimal conditions. In contrast, the simulated lipid transfer rate produced by the DNA nanostructure was in the range of $1.9$-$2.6 \times 10^7$ s$^{-1}$, three orders of magnitude faster than measured for natural scramblases. Experimentally, these determined rates similarly surpass the reported overall flipping rates by approx. three orders of magnitude. The reason is that the 2C DNA nanostructure opens up a larger diameter toroidal lipid pore, which is also more stable than transient water passages that were previously suggested to mediate spontaneous lipid flip-flops (29-32).

Example 6. Testing in Human Cells

In order to show the potential for in vivo applications, the DNA scramblase was tested in human cells. Breast cancer cells (MDA-MB-231) were incubated for one hour with the DNA scramblases and subsequently stained the cells with FITC-labeled Annexin V which has a high binding affinity for PS lipids. As the employed cells naturally possess a low level of PS in the outer membrane leaflet (33), Annexin V binding to untreated cells should be low. Successful scrambling by the 2C DNA nanostructures would be indicated by an elevated level of surface-exposed PS resulting in increased binding of FITC-Annexin V (FIG. 27). Confocal microscopy images presented in FIG. 28 show that the DNA nanostructures not only attached to the cells but also increased Annexin V binding in their vicinity. A negative control of incubating the cells with the DNA folding buffer confirmed the overall low binding of Annexin V in the absence of scrambling activity whereas a positive control using the apoptosis-inducing microbial alkaloid staurosporine showed similar maximum intensity of Annexin V binding as in the case of functional DNA nanostructure (FIG. 29). These results demonstrate that the DNA scramblase is able to induce lipid scrambling in human cells.

Example 7. Materials and Methods

All Atom MD Simulations of Lipid Scrambling

The caDNAno design of the DNA nanostructure (FIG. 30, panel A) was converted to an idealized all-atom representation and embedded into a lipid bilayer membrane using a previously described method (51). The resulting model was merged with a rectangular volume of electrolyte solution, minimized and equilibrated in the constant number of particles, temperature and pressure ensemble. The simulations employed CHARMM36 parameter set and were carried out using both NAMD and Anton. Below provides a detailed account of the simulation procedures BD Simulations of Lipid Scrambling The BD simulations were performed using the in-house GPU-accelerated program Atomic Resolution Brownian Dynamics (39). In the BD simulation, lipid head groups were modeled as point particles that interacted with each other via a repulsive potential. All other components of the systems, including the DNA nanostructure, the lipid tails and the electrolyte solution, were modeled implicitly. Position-dependent potential was used to confine motion of the lipid head groups to the volume they occupied in the all-atom simulations; the all-atom MD trajectories were also used to determine position-dependent diffusivity of the head groups.

DNA Nanostructure Assembly

All reagents were acquired from Sigma-Aldrich if not stated otherwise. DNA nanostructures were designed using caDNAno (40) and sequences optimized to minimize undesired hybridization sites. All DNA oligonucleotides were acquired from Integrated DNA Technologies (IDT). Unmodified DNA strands (purified by standard desalting) and 3'-Cy3-modified strands (HPLC-purified) were ordered pre-diluted to 100 µM in IDTE buffer (10 mM Tris, pH 8.0, 0.1 mM EDTA) and stored at −20° C. Cholesterol-tagged DNA strands were modified at the 3'-end via a 15 atom triethylene glycol spacer, purchased HPLC-purified, diluted to 100 µM in Milli-Q water (Merck Millipore) upon arrival and stored at 4° C. DNA nanostructures were assembled analogously as described to a previously described protocol (16). Briefly, an equimolar mixture of eight DNA strands was prepared at 1 µM final concentration per oligonucleotide in TE20 buffer (10 mM Tris, 1 mM EDTA, 20 mM MgCl$_2$, pH 8.0). If desired, cholesterol- or Cy3-modified strands were introduced by omitting the equivalent unmodified oligonucleotide and adding the modified one into the assembly mix instead. For cholesterol-modified DNA strands, stock solutions were heated to 55° C. for 10 min prior to addition to the assembly mix. Folding of DNA nanostructures was performed by heating the oligonucleotide mixture to 85° C. to ensure complete strand separation, and subsequent cooling to 25° C. via an 18 hour temperature gradient using a ProFlex™ PCR thermal cycler (Thermo Fisher Scientific). Folded structures were stored at 4° C. protected from light.

Polyacrylamide Gel Electrophoresis (PAGE) of DNA Nanostructures

The gel was cast at a concentration of 10% polyacrylamide supplemented with 0.5× Tris-borate-EDTA (TBE) and 11 mM MgCl$_2$. Per 15 ml gel mixture, 150 µl of 10% ammonium persulfate solution and 10 µl N,N,N',N'-Tetramethylethylenediamine were added to initiate polymerization. 2 µl of DNA nanostructures at 1 µM were mixed with 0.4 µl custom-made 6× loading dye (6×: 15% Ficoll 400, 0.9% Orange G diluted in TE20 buffer) and 2 µl of the mixture were loaded into the well. The gel was run in a Mini-PROTEAN Tetra Cell (Bio-Rad) for 90 min at 100 V in 0.5×TBE supplemented with 11 mM MgCl$_2$ and afterwards stained using GelRed (Biotium) and the bands visualized via UV-transillumination. The gray scale of the acquired image was inverted and subsequently the background subtracted using the rolling ball method (radius=300 pixel) in Fiji Preparation of Lipid Vesicles:

Giant unilamellar vesicles (GUVs) were prepared by electroformation using a Nanion Vesicle Prep Pro setup. 1-palmitoyl-2-oleoyl-sn-glycero-3-phosphocholine lipid (POPC; Sigma-Aldrich) and 1-palmitoyl-2-{6-[(7-nitro-2-1, 3-benzoxadiazol-4-yl) amino] hexanoyl}-sn-glycero-3-phosphocholine (NBD-PC; Avanti Polar Lipids) were dissolved in chloroform and mixed in a w/w ratio of 200:1 (POPC:NBD-PC). 100 µl of the lipid mixture at 5 mg/ml was spin-coated on the conducting surface of an Indium Tin Oxide (ITO)-coated glass slide (Nanion/VisionTek). Chloroform was evaporated for 1 hour in a desiccator following which 600 µl of sucrose buffer (100 mM sucrose, 20 mM HEPES at pH 7.4) was deposited within the O-ring chamber which was subsequently sealed with another ITO-coated slide (conducting surface facing the other). The electroformation chamber was then connected to the Nanion Vesicle Prep Pro and the electroformation protocol proceeded in 3 steps: (i) The A/C voltage increased linearly from 0 to 3.2 V peak to peak (p-p) at 10 Hz over 1 hour, (ii) the voltage stayed at 3.2 V p-p and 10 Hz for 50 min, (iii) the frequency decreased linearly to 4 Hz over 10 min and was maintained for another 20 min. Electroformation was carried out at 37° C. and vesicles were stored at 4° C. protected from light. Vesicles were not used longer than 36 hours after formation.

Dithionite Quenching Assay

Assembled DNA nanostructures (1 µM) with either one or two cholesterol modifications were mixed with 0.5% poly(ethylene glycol) octyl ether (OPOE), pre-diluted in TE20, in a 7:1 ratio and incubated for 2 min at room temperature. The mixture was then diluted in glucose buffer (100 mM glucose, 4 mM $MgCl_2$, 20 mM HEPES titrated to pH 7.4 with KOH) and added to 20 µl GUV solution at a final concentration of 100 nM DNA nanostructures. Samples were then incubated for 90 to 120 min on a 1% BSA-coated glass coverslip within an incubation chamber (Grace Bio-Labs) at room temperature allowing the vesicles to settle to the bottom due to the density gradient between the intravesicular sucrose and extravesicular glucose as well as the cholesterol-modified DNA nanostructures to anchor into the lipid membrane. Dithionite was dissolved in 1 M Tris at pH 10 at a concentration of 1 M and then pre-diluted in 50 mM glucose, 4 mM $MgCl_2$, and 20 mM HEPES pH 7.4 to a concentration of 15 mM dithionite freshly before each experiment. To initiate NBD dye quenching, 30 µl of diluted dithionite solution were carefully added to the incubated vesicles to a final concentration of 4.5 mM dithionite at approximately one minute after starting the recording. Chambers were covered throughout with a glass slide to prevent evaporation except when the dithionite quenching solution was added. At all times in the protocol at least 4 mM $MgCl_2$ were present to keep the DNA nanostructures stable over time (see Table 3 for detailed buffer conditions).

Image Acquisition and Analysis

Images were acquired on an Olympus FluoView filter based FV1200E-IX83 laser scanning microscope using a 60× oil immersion objective (UPLSAPO6OXO/1.35). NBD excitation was performed using a 25 mW 473 nm laser diode at 1% laser power and emission was collected between 490 and 525 nm. Cy3 was excited with a 1.5 mW 543 nm HeNe laser at 5% laser power and emitted light collected between 560 and 660 nm. For statistical analysis a z-stack (slice thickness 300 nm) was recorded of the field of view before and 35 min after dithionite addition with separate excitation of the 473 and 543 nm laser lines at a sampling speed of 2.0 µs/pixel. For single vesicle quenching traces, vesicles of similar size were kept in focus and images were recorded every 10 s in between the z-stacks while exciting with both lasers simultaneously. Images were analyzed using Fiji. Vesicles were identified and located from the fluorescence signal collected from Cy3-labeled DNA nanostructures by applying a ring-shaped selection area over the fluorescent ring at a height close to the equatorial plane. NBD fluorescence intensity for each vesicle was then determined by measuring the mean grey value of the equivalent area in the respective images of the NBD emission channel. Values were background-subtracted by measuring and averaging over three areas without vesicles. Intensities per vesicle were normalized to the average intensity of the first five data points of each trace.

Annexin V Staining Experiments on Human Cells

Cell preparation: MDA-MB-231 cells were acquired from the Cancer Research UK Cambridge Institute Biorepository where the cells were authenticated by multiplex PCR and short tandem repeat (STR) profiling including detection of mouse cell contamination. Cells were maintained in Dulbecco's Modified Eagle's Medium (DMEM; Sigma-Aldrich) supplemented with 10% (v/v) heat-inactivated fetal calf serum (FCS; Thermo Scientific) at 37° C. and 5% $CO_2$. A concentration of 30,000 MDA-MB-231 cells/250 µL medium was seeded on a cover glass placed in a well of a 48-well plate (day 0) and grown for two nights under the same conditions as stated above. Afterwards, cells were washed once with phosphate buffer saline (PBS) and then covered again in fresh medium.

Incubation with DNA Nanostructures:

DNA nanostructures with two cholesterol and two Cy3 tags were assembled as described above but in PBS at pH 7.4 supplemented with 8 mM $MgCl_2$ instead of TE20 buffer. 120 µl of assembled structures were added to cells (prepared as described above) in the well plate (final structure concentration 324 nM) and incubated for one hour at 37° C. and 5% $CO_2$. For the negative control performed in parallel, only the employed DNA folding buffer without DNA nanostructures was added. Subsequently, cells were washed with 500 µl of 1× Annexin V binding buffer (Abcam) and then incubated with 500 µl of 1×FITC-labeled Annexin V (Abcam) in binding buffer for 5 min (in accordance according to with the provided protocol provided by the manufacturer). After staining, cells were washed with 500 µl binding buffer once again and then fixed in 250 µl of 4% formaldehyde in binding buffer for 15 minutes on ice, followed by three washing steps with 250 µl binding buffer before being stored in the fridge overnight. On day four the cover glasses were transferred onto microscope slides by mounting them with Mowiol (Calbiochem Cat. No. 475904) following a previously described protocol 49. For this, 6 g of glycerol, 2.4 g of Mowiol powder (Calbiochem) and 6 ml of distilled water were added to 12 ml of 0.2 M Tris buffer (pH 8.0) and stirred for four hours. The solution was then left to rest for an additional two hours. Subsequently, the mixture was incubated for 10 min in a 50° C. water bath and finally centrifuged for 15 min at 5000×g. After removing the supernatant, the solution was stored at −20° C. before usage.

Image Acquisition and Analysis:

Images were acquired on the same confocal microscope as described for the dithionite quenching assay except that a 20× air objective was used (UPLSAPO20X/0.75). Filter set and laser power for Cy3-labeled DNA nanostructures were kept the same and parameters used for the NBD dye were applied for imaging FITC-labeled Annexin V as well. Detector voltages for both channels were kept fixed and were the same for all experiments. Z-stacks (slice thickness 500 nm) of cells were acquired with separate excitation of the 473 nm and 543 nm laser lines (sampling speed 2.0 µs/pixel). The bright field images were obtained by acquisition of the transmitted light of the 543 nm laser. Analysis was performed using Fiji.

TABLE 1

Nucleotide sequence of DNA strands forming the DNA nanostructure.

| Name | Length | Sequence | |
|------|--------|----------|---|
| sc1 | 47 | CCTTTCCACGAACACAGGGTTGTCC GATCCTATATTACGACTCCTTT | SEQ ID NO: 1 |
| sc2 | 34 | TTTGGGAAGGGGTTCGCAAGTCGCA CCCTAAACG | SEQ ID NO: 2 |
| sc3 | 36 | TCTTATCCTGCATCGAAAGCTCAAT CATGCATCTTT | SEQ ID NO: 3 |

TABLE 1 -continued

Nucleotide sequence of DNA strands forming the DNA nanostructure.

| Name | Length | Sequence | |
|---|---|---|---|
| sc4 | 23 | TTTATGTTGAAGGCTCAGGATGC | SEQ ID NO: 4 |
| st1 | 36 | TTTATCGGACATTCAACATGGAGTCGTGGTGCGACT | SEQ ID NO: 5 |
| st2 | 34 | TGCGAACAGGATAAGACGTTTAGAATATAGGTTT | SEQ ID NO: 6 |
| st3 | 47 | TTTTTCGATGCCCCTTCCCGATGCATGAAGGGCATCCTGAGCCACCC | SEQ ID NO: 7 |
| st4 | 23 | TGTGTTCGTGGAATTGAGCTTTT | SEQ ID NO: 8 |
| sc2C | 35 | TTTGGGAAGGGGTTCGCAAGTCGCACCCTAAACGA-CholTEG | SEQ ID NO: 9 |
| sc4C | 24 | TTTATGTTGAAGGCTCAGGATGCA-CholTEG | SEQ ID NO: 10 |
| st2F | 34 | TGCGAACAGGATAAGACGTTTAGAATATAGGTTT-Cy3 | SEQ ID NO: 11 |
| st4F | 23 | TGTGTTCGTGGAATTGAGCTTTT-Cy3 | SEQ ID NO: 12 |

For 1C DNA nanostructures the sc4 strand was replaced with sc4C in the assembly mix, for 2C additionally sc2 was replaced with sc2C

Example 8. Additional Methods

All Atom MD Simulations of Lipid Scrambling

The caDNAno design of the DNA nanostructure (FIG. 30, panel A) was converted to an idealized all-atom representation using a previously described method (42). To describe the cholesterol groups covalently attached to DNA, chemical models of the attachments, including all atoms of the linkers, were created; force field parameters were obtained using the CHARMM General Force Field (CGenFF) webserver (43). Following the design of the DNA nanostructure, cholesterol groups were added to termini of select DNA strands; the cholesterol groups were initially placed extended in opposite directions away from the DNA nanostructure.

Before inserting into a lipid membrane, the all-atom model of the DNA nanostructure was simulated for 1 ns in vacuum using the ENRG MD method (44), which allowed the structure to globally relax its conformation. The DPhPC and DPhPE lipid membranes were prepared by replicating a small patch of a pre-equilibrated lipid bilayer. After merging the DNA nanostructure with the lipid membranes, lipid molecules located either within 3 Å of the nanostructure or inside the nanostructure were removed. For the DPhPC membrane system, $Mg^{2+}$-hexahydrates (45) were randomly placed near the channels in the amount required to exactly compensate its electrical charge; the DPhPE membrane system contained no magnesium ions. Following that, water and 1 M KCl were added to both DPhPC and DPhPE systems using the Solvate and Autoionize plugins of VMD.

Upon assembly, the systems were minimized using the conjugate gradient method for 1200 steps to remove steric clashes. During the minimization process, all non-hydrogen atoms of the DNA nanostructure were harmonically restrained (with the spring constant $k_{spring}$=1 kcal/(mol $Å^2$)) to their initial coordinates. After minimization, the systems were equilibrated in the constant number of atoms, pressure (P=1 atms) and temperature (T=295 K) ensemble. The pressure and temperature were maintained using the Nose-Hoover Langevin piston (46, 47) and Langevin thermostat (48), respectively. The ratio of each system's dimensions was kept constant within the plane of the membrane (x-y plane); the system's dimension normal to the membrane (Z axis) was not constrained. Initially, the systems were equilibrated for 205 ns having all non-hydrogen atoms of the DNA nanostructure harmonically restrained ($k_{spring}$=1 kcal/(mol $Å^2$)) to their initial coordinates, which allowed the lipid and water to adopt equilibrium configurations. Following that, the spring constants of the restraints were decreased to 0.5 and then to 0.1 kcal/(mol $Å^2$); the systems were equilibrated at each spring constant value for 4.8 ns. Next, spatial restraints were replaced by a network of harmonic restraints that maintained distances between atomic pairs at their initial values; such elastic restraints excluded hydrogen atoms, phosphate groups, atoms in the same nucleotide and pairs separated by more than 8 Å. The systems were simulated under such elastic restraints for 14.4 ns; the spring constants of the restraints were decreased from 0.5 to 0.1 and then to 0.01 kcal/(mol $Å^2$) in 4.8 ns steps.

All equilibration simulations were performed using the program NAMD2 (37), periodic boundary conditions, the CHARMM36 parameter set for water, ions and nucleic acids (36), CHARMM parameters for the lipid bilayer, custom parameterization of ion-DNA, ion-ion and DNA-lipid interactions (45, 49). All equilibration simulations employed a 2-2-6 fs multiple time-stepping, SETTLE algorithm to keep water molecules rigid (50), RATTLE algorithm to keep all other covalent bonds involving hydrogen atoms rigid (51), a 8-10-12 Å cutoff for van der Waals and short-range electrostatic forces. Long-range electrostatic interactions were computed using the particle mesh Ewald (PME) method (52) over a 1.2 Å resolution grid (53). The system's coordinates were recorded every 2.4 μs.

Production simulations of the DPhPE system were performed on the Anton 2 supercomputer (38) using simulation parameters equivalent to those described above for NAMD, except that temperature and pressure were maintained using the Nose-Hoover thermostat (54, 55) and the Martyna-Tobias-Klein barostat (46). The system's coordinates were recorded every 240 μs. Production simulations of the DPhPC system were performed on Blue Waters petascale system (UIUC) using NAMD2 (37).

BD Simulations of Lipid Scrambling

All BD simulations were performed using an in-house GPU-accelerated software package Atomic Resolution Brownian Dynamics (ARBD) (39). The head groups of lipid molecules were represented by beads that interacted with one another via a short-range repulsive potential (FIG. 12); a cutoff of 10 Å was used to evaluate all bead-bead interactions. All other components of the system were taken into account implicitly. A 3D grid-based potential confined diffusion of the lipid head groups to the volume explored in the corresponding all-atom MD simulations. The diffusive motion of the beads was defined by a local diffusivity map that also derived from the all-atom simulations.

At each time step of a BD simulation, the force on each bead was determined from the system configuration; the bead's coordinates were updated according to the following expression:

$$r_i(t+\delta t) = r_i(t) + \frac{D(r_i)\delta t}{k_B T} F_i + \nabla D(r_i)\delta t + \sqrt{2D(r_i)\delta t}\, w$$

where r(t) denotes the position at time t, D(r) is the position-dependent diffusivity, F is the deterministic force, δt is the timestep, $k_B$T is the thermal energy, w is a 3D vector with elements selected randomly from a standard normal distribution, and the subscript i indicates terms corresponding to ith bead. The deterministic force F had two components: one describing repulsive interaction from all other beads within the cutoff radius (FIG. 12), and the other derived from a grid-based potential describing confinement of the toroidal pore (FIG. 14).

In all BD simulations of the toroidal pore system, the simulation time step was 200 fs; the beads' coordinates were recorded every 2.4 ns. Position-dependent diffusivity D(r) was assumed to depend only on the distance from the central axis of the pore. The specific functional form, FIG. 13, panel B, was derived from the analysis of the all-atom MD simulations of the toroid pore, FIG. 13, panel A, and from the simulations of the planar lipid membranes, FIG. 16, panel A. In the BD simulations of a planar lipid membrane, FIG. 16, panel B, the timestep was 2 fs; beads coordinates were recorded every 2.4 µs.

Generation of the 3D Grid-Based Potential.

The 3D grid-based potential was generated using the gridData module of Python. The following procedures describe generation of the 3D potential for the L=12 nm system. All other systems were generated following the same steps but for different numerical values of L.

Step 1:

To generated a grid-based potential in the 12 nm×12 nm×10 nm volume, a potential grid was first generated for a slightly larger volume: (12+2×padding)×(12+2×padding)×(10+2×padding) $nm^3$, where padding of 1 nm was used as a buffer zone to avoid numerical errors at the boundaries of the grid. The volume was then discretized with a resolution of 0.1 nm to span Cartesian coordinates from the following range: −7 nm≤X<7 nm, −7 nm≤Y<7 nm and −6 nm≤Z<6 nm, using the gridData module. Each grid point was assigned a value of the potential energy according to its coordinate. In order to mimic the bilayer membrane, grid points were assigned satisfying the following condition: −2.2 nm<Z<−1.8 nm or 1.8 nm<Z<2.2 nm, a value of 100 kcal/mol and zero to all other grid points (FIG. 14, panel A).

Step 2:

The inner surface of a toroidal pore was generated using the following catenoid function: R−c×cos h(Z/c), where R=$(X^2+Y^2)^{0.5}$ and constant c=2. All grid points satisfying the following conditions: 2.25 nm<R−c×cos h(Z/c)<2.75 nm and −1.8 nm<Z<1.8 nm, were set to 100 kcal/mol, producing a potential grid shown in (FIG. 14, panel B).

Step 3:

All grid points satisfying R−c×cos h(Z/c)<2.25 nm were set to 0, producing a toroidal pore (FIG. 14, panel C).

Step 4:

To enlarge the volume accessible to head group beads, the grid potential was convoluted with a spherical function of 0.9 nm radius using the scipy.signal.fftconvolve function of Python; the resulting potential grid is shown in FIG. 14, panel D.

Step 5:

To reverse the potential energy difference, all grid points that had values larger than 1 kcal/mol were set to 0 and all grid points that had values less than 1 kcal/mol were set 100 kcal/mol. Following that, the grid was convoluted with the following Gaussian window: $\exp(-0.5*(\mu/\sigma)^2)$, where µ=1.1 nm and σ=0.2 nm, to smooth the boundary between the regions of low and high energy (FIG. 14, panel E).

Step 6:

To remove the numerical errors produced by the convolution procedures, the grid was trimmed to target dimensions by removing the padding which was added initially. The final potential grid is shown in (FIG. 14, panel F).

Initialization of the BD Simulation.

For the planar lipid system (illustrated in FIG. 16, panel B), the initial coordinates of each beads were taken from the all-atom DPhPC system (FIG. 16, panel A). For the toroidal pore systems, the lipid patch size and the initial coordinates of the beads in the L=12 nm system were taken from the all-atom system (FIG. 2). Other systems (L=16, 20, 24 and 36 nm) were made by increasing the lipid patch size and the number of the beads, see Table 2.

TABLE 2

Systemsused for BD simulations of lipid scrambling

| L (nm) | Area ($nm^2$) per pore | Pore-to-lipid ratio, r |
|---|---|---|
| 12 | 144 | 0.0030 |
| 16 | 256 | 0.0017 |
| 20 | 400 | 0.0011 |
| 24 | 576 | 0.0008 |
| 36 | 1296 | 0.0003 |

The initial X and Y coordinates of each bead in the BD systems were randomly generated from a homogeneous distribution within the entire range of the system dimension L. The initial Z coordinates were set to be either 2 nm or −2 nm with equal probability. Although the initial number of beads in each leaflet could differ slightly between the leaflets, the beads attained equilibrium partitioning within the first several nanoseconds of the BD simulation.

Validation of the BD Approach.

The BD model of the toroidal pore was validated by comparing the equilibrium local concentration of the BD beads to the concentration of the phosphorus atoms of the lipid head groups observed in the all-atom MD simulation. FIG. 15, panel A, shows the local concentration of the phosphorus atoms observed in the ~2 µs unconstrained equilibration of the DPhPE system sampled one frame per 2.4 ns. FIG. 15, panel B, shows the local concentration of the BD beads within the last 48 µs of the BD simulation of the L=12 nm system (FIG. 5, panel B) sampled one frame per 2.4 ns. F The timescale of the BD simulation was validated by comparing the 2D diffusivity of lipids in a planar lipid bilayer system to the result of the all-atom MD simulation. For the all-atom MD simulation, the DPhPC lipid bilayer membrane was solvated in 50 mM $MgCl_2$ and 1 M KCl solution. The final system measured 10 nm×10 nm×10 nm and contained ~100,000 atoms (FIG. 16). Under periodic boundary condition, the lipid membrane was periodic in X and Y directions. Upon assembly, the system was minimized using the conjugate gradient method for 2400 steps to remove steric clashes. Then, the system was simulated in the NPT ensemble without any constraint for 137 ns. The trajectory of the last 100 ns was used to calculate the mean squared displacement (MSD) and the diffusivity (FIG. 16, panels C and D). The BD system was built by taking the coordinates of the phosphorus atoms from the all-atom simulation, FIG. 16, panel B, as described previously. The position-dependent potential was also made by the procedure described before, skipping the steps required for generation of the toroidal pore (Steps 2 and 3). The BD system was simulated for 190 ns with a 2 fs timestep; the coordinates of the beads were recorded every 2.4 µs. Similar to the analysis of the all-atom MD trajectory, the last 100 ns of the BD trajectory were used to calculated the mean squared displacement (MSD) and the diffusivity, FIG. 16, panels C and D. The resulting lipid diffusivities obtained from the BD and all-atom MD simulations are in good quantitative agreement with one another.

Analysis of Simulation Trajectories

Calculations of lipid diffusivity. The local diffusivity of lipids was calculated following a previously described protocol (56, 57). In the case of unrestrained Brownian motion, the diffusivity can be calculated from the Einstein relation:

$$2d_f D = \lim_{t \to \infty} \frac{1}{t} \langle (r(t) - r(0))^2 \rangle$$

where $d_f$ is the number of translational degrees of freedom and $r(t)$ is the position of the molecule at time t. In simulations, however, the phosphorus atoms of the lipid are not free to move in all three dimensions as their motion is confined to the surface of the lipid bilayer. Nevertheless, the above expression can be used to obtain an approximate dependence of the lipid diffusion constant on the radial distance from the center of the nanopore and to compare lipid diffusion in the all-atom and BD systems.

To determine position-dependent diffusivity from an all-atom MD trajectory, all frames of the trajectory were first aligned so that the center of the DNA nanostructure (or of the lipid membrane in the systems that did not contain the nanostructure) was located at the origin. The BD trajectories did not require alignment. Then, trajectories of individual phosphorus atoms of the lipid molecule or BD beads were extracted; the trajectories were then divided into 20 ns segments. Each segment was categorized to belong to one of the radial bins based on the average radial distance of the atom or the bead; 1 nm bin spacing was used. Position-dependent characterization was not carried out in the case of the planar lipid membranes (FIG. 16). Following that, the mean square displacements MSD was calculated for each segment and averaged over all the N molecules in each bin as (58)

$$MSD(t) = \frac{1}{N} \frac{\Delta t}{T-t} \sum_{i=1}^{N} \sum_{t_0=0}^{T-t-1} |r(t_0) - r(t_0 + t)|^2$$

The first sum runs over the N molecules and the second sum runs over all time frames smaller than T−t, where T is the sampling time (20 ns), $t_0$ is the time of the first frame in the trajectory segment and $\Delta t$ is the time interval between the consecutive frames of a simulation trajectory. The slope of a linear least-squares fit to the MSD dependence on time was used as a measure of the effective diffusion coefficient for each radial bin: the 3D diffusivity was ⅙ of the slope. For the planar lipid membrane systems (FIG. 16) only X and Y coordinates were taken into account during the analysis, corresponding to diffusion in two dimensions. In that case, the diffusivity was ¼ of the slope.

Calculation of Local Concentration.

The local concentration was computed as described previously (59). The simulation system was divided into a collection of 5 Å×5 Å×5 Å volumes and calculated the average concentration of the particles in each volume using all available frames of the simulation trajectory. The 3D concentration in the cylindrical coordinate system was averaged over the azimuthal angle to obtain the mean concentration within the R-Z plane, as described previously (60). Finally, the contouf function from the python matplotlib package was used to generate the local concentration plots, which were then used to display the data.

Alternative Dithionite Reduction Protocol.

In the alternative experimental protocol, the final concentration of dithionite was the same, 5 mM, however, the actual amount of dithionite solution added was greater (see Table 4).

TABLE 3

Buffer solutions used in dithionite reduction assays.

| Buffer # | Name | Buffer conditions |
| --- | --- | --- |
| 1 | HEPES buffer | 20 mM HEPES pH 7.4 |
| 2 | TE20 | 20 mM $MgCl_2$ |
|   |   | 10 mM Tris pH 8.0 |
|   |   | 1 mM EDTA |
| 3 | Dithionite dilution solution | 50 mM glucose |
|   |   | 20 mM HEPES pH 7.4 |
|   |   | 4 mM $MgCl_2$ |
| 4 | Dithionite solution | 50 mM glucose |
|   |   | 20 mM HEPES pH 7.4 |
|   |   | 4 mM $MgCl_2$ |
|   |   | 15 mM dithionite |
|   |   | 15 mM Tris pH 10.0 |
| 5 | Glucose solution | 100 mM glucose |
|   |   | 20 mM HEPES pH 7.4 |
|   |   | 4 mM $MgCl_2$ |
| 6 | Sucrose solution | 100 mM sucrose |
|   |   | 20 mM HEPES pH 7.4 |
| 7 | Incubation solution | 7 µl TE20 (#2) |
|   |   | 1 µl 0.5% OPOE in TE20 |
|   |   | 42 µl glucose solution (#5) |
| 8 | Measurement solution | 20 µl sucrose solution (#6) |
|   |   | 50 µl incubation solution (#7) |
|   |   | 30 µl dithionite solution (#4) |

TABLE 4

Alternative protocol of dithionite reduction assay (results shown in FIG. 16)

| Amount | Buffer conditions |
| --- | --- |
| 20 µl | GUV solution in 100 mM sucrose, 20 mM HEPES pH 7.4 |
| 24.5 µl | 100 mM Glucose, 20 mM HEPES pH 7.4 |
| 0.5 µl | 0.5% OPOE in TE20 |
| 5 µl | DNA nanostructures at 1 µM in TE20 buffer Incubation for approx. 150 min at room temperature Record z-stacks of multiple areas containing vesicles |
| 50 µl | 10 mM dithionite in 80 mM glucose, 20 mM HEPES pH 7.4 Record z-stacks of multiple areas containing vesicles after one hour |

The greater amount of added solution caused the vesicles to move upon dithionite addition in most cases. Therefore, it was rarely possible to compare the intensity before and after addition for one and the same vesicle. Alternatively, z-stacks of several areas containing vesicles were acquired before and one hour after dithionite addition. NBD fluorescence intensities before and after dithionite addition were determined similarly as described above. Intensity values were only background subtracted but not normalized (FIG. 23, panel A). The fairly large spread in the intensity distribution can be explained by the use of a 20× air objective (UPLSAPO20X, NA=0.75) in these experiments which resulted in a larger focal volume in z-direction. This caused the fluorescence intensity to depend on the size meaning that larger vesicles had a higher fluorescence intensity than smaller ones (data not shown). However, the data still showed that for vesicles incubated with 2C nanostructures the highest peak is associated with a complete NBD reduction which is in contrast to 1C nanostructure experiments where the highest peak is located at a much higher remaining fluorescence intensity. A small fraction of vesicles in the case of 1C nanostructures is bleached completely which could be caused by dithionite leakage into the vesicles while they were moved upon dithionite addition. Fluorescence intensity traces show an exponential decay to almost 0 or to ~0.5 for vesicles incubated with 2C or 1C nanostructures, respectively (FIG. 23, panel B). Spikes in intensity are caused by vesicles temporarily being out of focus. The results are comparable to the assay performed above. However, the slight improvements in the protocol effectively prevented vesicles from moving while still not exposing them to an osmotic shock which made results more consistent.

Scrambling Rate Calculations Regarding Lipid Diffusion

The mean time ⟨τ⟩ for a particle that diffuses on a sphere until it encounters and gets irreversibly captured by a single, immobile trapping region can be approximated by the equation:

$$\langle \tau \rangle \approx \frac{b^2}{2D}\left[\ln\frac{b}{s} - \frac{1}{2}\right]$$

where s is the radius of the trapping region, b the diameter of the sphere and D the diffusion coefficient of the particle diffusing along the spherical surface (adapted from equation (6.2) from using b=2R and d≈s for the limit of a point-like diffusing particle and direct absorption upon encounter). This can be applied to estimating the mean time it takes for a phospholipid, that diffuses within the membrane of a vesicle with the diameter b, to be flipped (=captured) by our DNA-induced toroidal pore of radius s. The equation holds if 1>>s/b which is true for the size of the DNA nanostructure embedded in a giant unilamellar vesicle. With this equation, ⟨τ⟩ was calculated for the average diameter of the vesicles used for the determination of scrambling rates (see FIG. 26, Panel B) and compared to the experimentally determined values (see Table 5).

TABLE 5

Calculated and experimentally determined rates. $N_{total}$ refers to the total number of lipids in a vesicle of diameter b. k is the lipid scrambling rate per scramblase.

| s (nm) | $D^{26}$ (μm² s⁻¹) | b (μm) | $N_{total}$ (10⁹) | $\langle\tau\rangle_{calc}$ (min) | $\langle\tau\rangle_{exp}$ (min) | $k_{calc}$ (10⁷ s⁻¹) | $k_{exp}$ (10⁷ s⁻¹) |
|---|---|---|---|---|---|---|---|
| 2.3 | 7 | 19.4 | 3.47 | 3.61 | 4.76 | 1.60 | 1.62 |

Using ⟨τ⟩, the scrambling rate k for a single DNA nanostructure can be estimated analogously as performed for experimental rates (see FIG. 26) following:

$$k = \frac{N_{total}}{\langle\tau\rangle}.$$

With this equation, scrambling rates k were calculated and compared to the experimental values in Table 5.

Example 9. Light and Chemically Activated Scrambling

FIGS. 31 and 32 provide an overview of how the invention can be used. The artificial scramblase is composed of a nanostructure made from DNA, RNA, any other nucleic acid derivative, any hydrophilic region-containing compound, or any combination thereof that can be attached with hydrophobic moieties. The nanostructure may also contain one or multiple modifications that bind specifically to the surface of target prokaryotes or eukaryotes as well and an activation mechanism that regulates placement of the hydrophobic attachments with respect to the nanostructure (FIG. 31), or controls the hydrophobicity of the DNA nanostructure surface (FIG. 32). The activation mechanism may involve any external stimuli or internal cellular changes including but not limited to chemical, thermal, mechanical, electric potential, or electromagnetic triggering of structural changes within the nanostructure.

The majority of biological nanopores become active only in the presence of specific environmental stimuli. As demonstrated recently by the Howorka lab [17], the architecture of DNA nanopores is conducive to ligand-gating. However, insertion of DNA nanopores into lipid membrane is either irreversible or highly stochastic [15,16].

With the present invention, using an activator, such as UV light, other forms of electromagnetic radiation, or a chemical agent, can cause a conformal change in the structure of the synthetic scramblase or can otherwise can affect the availability of the hydrophobic molecule that anchors the scramblase in the lipid membrane. Thus, the synthetic scramblase function is able to be activated or deactivated by exposing cells in contact with the scramblase to electromagnetic radiation or a chemical agent. This allows to the scrambling function to be activated or deactivated with regard to time, but can also control the areas where the scrambling function occurs. For example, the synthetic scram blase can be selectively administered to a desired region, tissue type, or groups of cells within a patient and then activated at the desired time. Alternatively, the synthetic scramblase can be administered over a wide region or area, and only the specific desired region, tissue type, or groups of cells are exposed to the activator.

Optical control over the insertion process is achievable using established photo-switchable molecules-azobenzene-whose isomeric state determines whether the two DNA strands can hybridize into a double-stranded duplex [69,70]. For example, one embodiment modifies the existing design of DNA nanopores to preferentially locate cholesterol anchors inside the DNA bundle (see FIG. 33), which should render the DNA nanopore inactive. The complimentary DNA strand will be conjugated with several azobenzene moieties. In the trans configuration, the presence of azobenzene allows the stable formation of the duplex [70]. However, transition to a cis-geometry, triggered by ultraviolet (<340 nm) light, will cause the duplex adjacent to the anchor to melt and allow the cholesterol to interact with and eventually insert into the bilayer, activating the nanopore. Such activation can be reversed by stimulating a cis-to-trans transition of azobenzene by visible blue (>400 nm) light.

By equipping a synthetic scramblase with an activation mechanism and the ability to target plasma membranes of specific cell types, the synthetic scramblase can be made suitable for biomedical applications with the scrambling activity being controlled by the geometry of the toroidal lipid pore. On demand, target cell-specific lipid scrambling can aid patients suffering from impaired lipid scrambling or be used to trigger phagocytic uptake of PS-exposing intruder cells by macrophages, including cells carrying cancer specific plasma membrane antigens. Furthermore, the mechanism of the present synthetic scramblase is independent of any cell-specific apoptosis pathways, making it applicable to a broad range of cell types. Control over lipid homeostasis by synthetic nanostructures opens up a yet to be explored direction for designing personalized drugs and therapeutics for a variety of health conditions. Ultimately, the ability to outperform naturally evolved proteins allowed for a glimpse at the tremendous opportunities still to be explored in nucleic acid-based nanotechnology.

Example 10. Drug Delivery into Cells

FIG. 34 illustrates an example of how the present invention can be used to deliver a drug, chemical agent, or lipid vesicle into the interior of a cell. A lipid vesicle containing a selected drug is administered to contact one or more desired cells. The membrane of the lipid vesicle contains an inactivated form of a synthetic scramblase, and the inner leaflet of the vesicle lipid membrane comprises an activating lipid which induces endocytosis.

Once activated, the scramblase forms a toroidal pore which allows the activating lipid to be transported to the outer surface of the vesicle where it can bind to a receptor on the surface of the cell. Once bound, the activating lipid causes the cell to absorb the vesicle which subsequently releases the drug into the cell. The activation of the scramblase can be caused by the binding of the vesicle to the cell, or by other means such as those described in Example 9. Accordingly, the administration of the drug into the desired cells is able to controlled through the activation of the scramblase.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

REFERENCES

1. M. S. Bretscher, Asymmetrical Lipid Bilayer Structure for Biological Membranes. Nat. New Biol. 236, 11-12 (1972).
2. A. Castegna, C. M. Lauderback, H. Mohmmad-Abdul, D. A. Butterfield, Modulation of phospholipid asymmetry in synaptosomal membranes by the lipid peroxidation products, 4-hydroxynonenal and acrolein: implications for Alzheimer's disease. Brain Res. 1004, 193-197 (2004).
3. H. Mohmmad Abdul, D. A. Butterfield, Protection against amyloid beta-peptide (1-42)-induced loss of phospholipid asymmetry in synaptosomal membranes by tricyclodecan-9-xanthogenate (D609) and ferulic acid ethyl ester: Implications for Alzheimer's disease. Biochimica et Biophysica Acta (BBA)—Molecular Basis of Disease. 1741, 140-148 (2005).
4. S. K. Sahu, S. N. Gummadi, N. Manoj, G. K. Aradhyam, Phospholipid scramblases: An overview. Arch. Biochem. Biophys. 462, 103-114 (2007).
5. P. F. Devaux, A. Herrmann, N. Ohlwein, M. M. Kozlov, How lipid flippases can modulate membrane structure. Biochimica et Biophysica Acta (BBA)—Biomembranes. 1778, 1591-1600 (2008).
6. A. Zachowski, Phospholipids in animal eukaryotic membranes: transverse asymmetry and movement. Biochem. J. 294, 1-14 (1993).
7. E. M. Bevers, P. Comfurius, D. Dekkers, M. Harmsma, R. Zwaal, Transmembrane Phospholipid Distribution in Blood Cells: Control Mechanisms and Pathophysiological Significance. Biol. Chem. 379, 973-986 (1998).

8. T. Pomorski, J. C. M. Holthuis, A. Herrmann, G. van Meer, Tracking down lipid flippases and their biological functions. J. Cell Sci. 117, 805-813 (2004).
9. K. Yu et al., Identification of a lipid scrambling domain in ANO6/TMEM16F. Elife. 4, e06901 (2015).
10. R. F. A. Zwaal, P. Comfurius, E. M. Bevers, Scott syndrome, a bleeding disorder caused by defective scrambling of membrane phospholipids. Biochimica et Biophysica Acta (BBA)—Molecular and Cell Biology of Lipids. 1636, 119-128 (2004).
11. K. S. Ravichandran, U. Lorenz, Engulfment of apoptotic cells: signals for a good meal. Nat. Rev. Immunol. 7, 964-974 (2007).
12. M. Langecker et al., Synthetic Lipid Membrane Channels Formed by Designed DNA Nanostructures. Science. 338, 932-936 (2012).
13. J. R. Burns, E. Stulz, S. Howorka, Self-assembled DNA nanopores that span lipid bilayers. Nano Lett. 13, 2351-2356 (2013).
14. J. R. Burns et al., Lipid-Bilayer-Spanning DNA Nanopores with a Bifunctional Porphyrin Anchor. Angew. Chem. Int. Ed. 52, 12069-12072 (2013).
15. A. Seifert et al., Bilayer-Spanning DNA Nanopores with Voltage-Switching between Open and Closed State. ACS Nano. 9, 1117-1126 (2015).
16. K. GOpfrich et al., DNA-tile structures induce ionic currents through lipid membranes. Nano Lett. 15, 3134-3138 (2015).
17. J. R. Burns, A. Seifert, N. Fertig, S. Howorka, A biomimetic DNA-based channel for the ligand-controlled transport of charged molecular cargo across a biological membrane. Nat. Nanotechnol. 11, 152-156 (2016).
18. K. GOpfrich et al., Ion Channels Made from a Single Membrane-Spanning DNA Duplex. Nano Lett. 16, 4665-4669 (2016).
19. K. GOpfrich et al., Large-Conductance Transmembrane Porin Made from DNA Origami. ACS Nano. 10, 8207-8214 (2016).
20. S. Krishnan et al., Molecular transport through large-diameter DNA nanopores. Nat. Commun. 7, 12787 (2016).
21. S. Khalid, P. J. Bond, J. Holyoake, R. W. Hawtin, M. S. P. Sansom, DNA and lipid bilayers: self-assembly and insertion. J. R. Soc. Interface. 5, S241-50 (2008).
22. K. Schlosser, Y. Li, Biologically inspired synthetic enzymes made from DNA. Chem. Biol. 16, 311-322 (2009).
23. S. K. Silverman, Catalytic DNA: Scope, Applications, and Biochemistry of Deoxyribozymes. Trends Biochem. Sci. 41, 595-609 (2016).
24. J. C. McIntyre, R. G. Sleight, Fluorescence assay for phospholipid membrane asymmetry. Biochemistry. 30, 11819-11827 (1991).
25. I. Menon et al., Opsin is a phospholipid flippase. Curr. Biol. 21, 149-153 (2011).
26. M. Malvezzi et al., Ca2+-dependent phospholipid scrambling by a reconstituted TMEM16 ion channel. Nat. Commun. 4, 2367 (2013).
27. P. Williamson et al., Continuous Analysis of the Mechanism of Activated Transbilayer Lipid Movement in Platelets. Biochemistry. 34, 10448-10455 (1995).
28. M. A. Goren et al., Constitutive phospholipid scramblase activity of a G protein-coupled receptor. Nat. Commun. 5, 5115 (2014).
29. A. H. de Vries, A. E. Mark, S. J. Marrink, Molecular Dynamics Simulation of the Spontaneous Formation of a Small DPPC Vesicle in Water in Atomistic Detail. J. Am. Chem. Soc. 126, 4488-4489 (2004).
30. H. Leontiadou, A. E. Mark, S. J. Marrink, Antimicrobial Peptides in Action. J. Am. Chem. Soc. 128, 12156-12161 (2006).
31. A. A. Gurtovenko, I. Vattulainen, Molecular Mechanism for Lipid Flip-Flops. J. Phys. Chem. B. 111, 13554-13559 (2007).
32. A. A. Gurtovenko, O. I. Onike, J. Anwar, Chemically induced phospholipid translocation across biological membranes. Langmuir. 24, 9656-9660 (2008).
33. S. D. Vallabhapurapu et al., Variation in human cancer cell external phosphatidylserine is regulated by flippase activity and intracellular calcium. Oncotarget. 6, 34375-34388 (2015).
34. J. M. Boon, T. N. Lambert, A. L. Sisson, A. P. Davis, B. D. Smith, Facilitated phosphatidylserine (PS) flip-flop and thrombin activation using a synthetic PS scramblase. J. Am. Chem. Soc. 125, 8195-8201 (2003).
35. H. Nakao, K. Ikeda, Y. Ishihama, M. Nakano, Membrane-Spanning Sequences in Endoplasmic Reticulum Proteins Promote Phospholipid Flip-Flop. Biophys. J. 110, 2689-2697 (2016).
36. A. D. MacKerell et al., All-atom empirical potential for molecular modeling and dynamics studies of proteins. J. Phys. Chem. B. 102, 3586-3616 (1998).
37. J. C. Phillips et al., Scalable molecular dynamics with NAMD. J. Comput. Chem. 26, 1781-1802 (2005).
38. D. E. Shaw et al., in SC14: International Conference for High Performance Computing, Networking, Storage and Analysis (IEEE Press, 2014), pp. 41-53.
39. J. Comer, A. Aksimentiev, Predicting the DNA sequence dependence of nanopore ion current using atomic-resolution Brownian dynamics. J. Phys. Chem. C. 116, 3376-3393 (2012).
40. S. M. Douglas et al., Rapid prototyping of 3D DNA-origami shapes with caDNAno. Nucleic Acids Res. 37, 5001-5006 (2009).
41. W. Fouquet, Quick Guide to STED Sample Preparation. Confocal Application Letter. Resolution., 49, 1-12 (2014).
42. J. Yoo, A. Aksimentiev, In situ structure and dynamics of DNA origami determined through molecular dynamics simulations. Proc. Natl. Acad. Sci. USA. 110, 20099-20104 (2013).
43. K. Vanommeslaeghe, A. D. MacKerell Jr, Automation of the CHARMM General Force Field (CGenFF) I: bond perception and atom typing. J. Chem. Inf. Model. 52, 3144-3154 (2012).
44. C. Maffeo, J. Yoo, A. Aksimentiev, De novo reconstruction of DNA origami structures through atomistic molecular dynamics simulation. Nucleic Acids Res. 44, 3013-3019 (2016).
45. J. Yoo, A. Aksimentiev, Improved Parametrization of Li+, Na+, K+, and Mg2+ Ions for All-Atom Molecular Dynamics Simulations of Nucleic Acid Systems. J. Phys. Chem. Lett. 3, 45-50 (2012).
46. G. J. Martyna, D. J. Tobias, M. L. Klein, Constant pressure molecular dynamics algorithms. J. Chem. Phys. 101, 4177-4189 (1994).
47. S. E. Feller, Y. Zhang, R. W. Pastor, B. R. Brooks, Constant pressure molecular dynamics simulation: The Langevin piston method. J. Chem. Phys. 103, 4613-4621 (1995).
48. A. T. BrUnger, X-PLOR, Version 3.1, A System for X-ray Crystallography and NMR (Yale University Press, New Haven, 1992).

49. J. Yoo, A. Aksimentiev, Improved Parameterization of Amine-Carboxylate and Amine-Phosphate Interactions for Molecular Dynamics Simulations Using the CHARMM and AMBER Force Fields. J. Chem. Theory Comput. 12, 430-443 (2016).
50. S. Miyamoto, P. A. Kollman, Settle: An analytical version of the SHAKE and RATTLE algorithm for rigid water models. J. Comput. Chem. 13, 952-962 (1992).
51. H. C. Andersen, Rattle: A "velocity" version of the shake algorithm for molecular dynamics calculations. J. Comput. Phys. 52, 24-34 (1983).
52. P. F. Batcho, D. A. Case, T. Schlick, Optimized particle-mesh Ewald/multiple-time step integration for molecular dynamics simulations. J. Chem. Phys. 115, 4003-4018 (2001).
53. R. D. Skeel, D. J. Hardy, J. C. Phillips, Correcting mesh-based force calculations to conserve both energy and momentum in molecular dynamics simulations. J. Comput. Phys. 225, 1-5 (2007).
54. S. Nose, A unified formulation of the constant temperature molecular dynamics methods. J. Chem. Phys. 81, 511-519 (1984).
55. W. G. Hoover, Canonical dynamics: Equilibrium phase-space distributions. Phys. Rev. A. 31, 1695-1697 (1985).
56. S. W. I. Siu, R. Vácha, P. Jungwirth, R. A. Böckmann, Biomolecular simulations of membranes: Physical properties from different force fields. J. Chem. Phys. 128, 125103 (2008).
57. B. M. Venkatesan et al., Lipid bilayer coated Al2O3 nanopore sensors:
    towards a hybrid biological solid-state nanopore. Biomed. Microdevices. 13, 671-682 (2011).
58. R. A. Böckmann, A. Hac, T. Heimburg, H. Grubmüller, Effect of Sodium Chloride on a Lipid Bilayer. Biophys. J. 85, 1647-1655 (2003).
59. C.-Y. Li et al., Ionic conductivity, structural deformation, and programmable anisotropy of DNA origami in electric field. ACS Nano. 9, 1420-1433 (2015).
60. J. Yoo, A. Aksimentiev, Molecular Dynamics of Membrane-Spanning DNA Channels: Conductance Mechanism, Electro-Osmotic Transport, and Mechanical Gating. J. Phys. Chem. Lett. 6, 4680-4687 (2015).
61. N. Kucerka, S. Tristram-Nagle, J. F. Nagle, Structure of fully hydrated fluid phase lipid bilayers with monounsaturated chains. J. Membr. Biol. 208, 193-202 (2005).
62. Nakano, M. et al. Flip-flop of phospholipids in vesicles: kinetic analysis with time-resolved small-angle neutron scattering. J. Phys. Chem. B 113, 6745-6748 (2009).
63. Li, S., Hu, P. & Malmstadt, N. Confocal imaging to quantify passive transport across biomimetic lipid membranes. Anal. Chem. 82, 7766-7771 (2010).
64. Fattal, E., Nir, S., Parente, R. A. & Szoka, F. C., Jr. Pore-forming peptides induce rapid phospholipid flip-flop in membranes. Biochemistry 33, 6721-6731 (1994).
65. Matsuzaki, K., Murase, O., Fujii, N. & Miyajima, K. An antimicrobial peptide, magainin 2, induced rapid flip-flop of phospholipids coupled with pore formation and peptide translocation. Biochemistry 35, 11361-11368 (1996).
66. Morra, G. et al. Mechanisms of Lipid Scrambling by the G Protein-Coupled Receptor Opsin. Structure 26, 356-367.e3 (2018).
67. Pomorski, T. G. & Menon, A. K. Lipid somersaults: Uncovering the mechanisms of protein-mediated lipid flipping. Prog. Lipid Res. 64, 69-84 (2016).
68. Gummadi, S. N. & Menon, A. K. Transbilayer movement of dipalmitoylphosphatidylcholine in proteoliposomes reconstituted from detergent extracts of endoplasmic reticulum. J. Biol. Chem. 277, 25337-25343 (2002).
69. Y. Yang, M. Endo, K. Hidaka, and H. Sugiyama. Photo-controllable DNA origami nanostructures assembling into predesigned multiorientational patterns. J. Am. Chem. Soc., 134:20645-20653 (2012).
70. H. Nishioka, X. Liang, T. Kato, and H. Asanuma. A photon-fueled DNA nanodevice that contains two different photoswitches. Angewandte Chemie International Edition, 124:1191-1194, (2012).
71. European Patent Application 2 695 949, Martin Langecker, (2014).

The invention claimed is:

1. A method of altering a biological state of a cell having a lipid membrane with a first leaflet and a second leaflet, the method comprising:
   (a) contacting the lipid membrane of the cell with a composition comprising one or more hydrophilic regions forming a nanostructure and one or more hydrophobic or amphiphilic molecules attached to the one or more hydrophilic regions, wherein the composition comprises one or more nucleic acids which form the nanostructure comprising at least one interconnected nucleic acid duplex, and wherein said one or more hydrophobic or amphiphilic molecules are able to insert the nanostructure into the lipid membrane; and
   (b) inserting the nanostructure into the lipid membrane and forming a toroidal pore in the lipid membrane surrounding the nanostructure, where the hydrophilic surfaces of the first and second leaflets are fused together to form a continuous structure,
      wherein selected lipids, other molecules, or both, in the first leaflet are transported to the second leaflet at a rate greater than a transport rate of a control lipid membrane which was not contacted with the composition, and
      wherein the increased rate of transportation alters the amount of the selected lipids, other molecules, or both, in the first and second leaflets, thereby altering the biological state of the cell.

2. The method of claim 1, wherein the increased rate of transportation of the selected lipids homogenizes the lipid composition between the first and second leaflet.

3. The method of claim 2, wherein the homogenization of the lipid composition induces or marks cells for apoptosis.

4. The method of claim 1, wherein the increased rate of transportation increases the amount of antigens, receptors, or signaling peptides in the outer leaflet of the membrane, thereby increasing a cellular activity.

5. The method of claim 1, wherein the increased rate of transportation decreases the amount of antigens, receptors, or signaling peptides in the outer leaflet of the membrane, thereby decreasing a cellular activity.

6. The method of claim 1, wherein the composition further comprises an activation mechanism able to cause a conformal change in the composition structure when exposed to stimuli, wherein said conformal change activates the nanostructure to be inserted into the lipid membrane and to form the toroidal pore.

7. The method of claim 6 further comprising administering the composition to a plurality of cells in a subject and exposing a selected portion of the plurality of cells to the stimuli thereby activating nanostructures within the selected portion of the plurality of cells.

8. The method of claim 6 wherein the activating mechanism comprises an azobenzene molecule attached to the composition and the stimuli comprises ultraviolet light.

9. The method of claim 6 wherein the activating mechanism comprises one or more molecules attached to the composition, wherein the one or more molecules are able to undergo conformational changes in response to a change in pH, and the stimuli comprises a local decrease in pH.

10. The method of claim 1, wherein the selected lipids or other molecules comprise a therapeutic drug or chemical agent.

11. A method of scrambling lipids or other molecules in a first and second leaflet of a biological membrane, the method comprising:
 (a) contacting the biological membrane with a composition comprising one or more hydrophilic regions forming a nanostructure and one or more hydrophobic or amphiphilic molecules attached to the one or more hydrophilic regions, wherein the composition comprises one or more nucleic acids which form the nanostructure comprising at least one interconnected nucleic acid duplex, and wherein said one or more hydrophobic or amphiphilic molecules are able to insert the nanostructure into the biological membrane; and
 (b) inserting the nanostructure into the biological membrane and forming a toroidal pore in the biological membrane surrounding the nanostructure, where the hydrophilic surfaces of the first and second leaflets are fused together to form a continuous structure,
 wherein lipids, other molecules, or both, in the first leaflet are transported to the second leaflet at a rate greater than a transport rate of a control biological membrane which was not contacted with the composition.

12. The method of claim 11, wherein lipids, other molecules, or both, in the second leaflet are transported to the first leaflet at a rate greater than a transport rate of a control biological membrane which was not contacted with the composition.

13. The method of claim 11, wherein the composition is modified to selectively transport specific lipids or other molecules from one of the leaflets to the other.

14. A method of altering a biological state of a cell having a lipid membrane with a first leaflet and a second leaflet, the method comprising:
 (a) contacting the lipid membrane of the cell with a composition comprising one or more hydrophilic regions forming a nanostructure and one or more hydrophobic or amphiphilic molecules attached to the one or more hydrophilic regions, wherein said one or more hydrophobic or amphiphilic molecules are able to insert the nanostructure into the lipid membrane; and
 (b) inserting the nanostructure into the lipid membrane and forming a toroidal pore in the lipid membrane surrounding the nanostructure, where the hydrophilic surfaces of the first and second leaflets are fused together to form a continuous structure,
 wherein the composition further comprises an activation mechanism able to cause a conformal change in the composition structure when exposed to stimuli, wherein said conformal change activates the nanostructure to be inserted into the lipid membrane and to form the toroidal pore, and the activating mechanism comprises an azobenzene molecule attached to the composition and the stimuli comprises ultraviolet light,
 wherein selected lipids, other molecules, or both, in the first leaflet are transported to the second leaflet at a rate greater than a transport rate of a control lipid membrane which was not contacted with the composition, and
 wherein the increased rate of transportation alters the amount of the selected lipids, other molecules, or both, in the first and second leaflets, thereby altering the biological state of the cell.

15. The method of claim 14, wherein the increased rate of transportation of the selected lipids homogenizes the lipid composition between the first and second leaflet.

16. The method of claim 15, wherein the homogenization of the lipid composition induces or marks cells for apoptosis.

17. The method of claim 14, wherein the increased rate of transportation increases the amount of antigens, receptors, or signaling peptides in the outer leaflet of the membrane, thereby increasing a cellular activity.

18. The method of claim 14, wherein the increased rate of transportation decreases the amount of antigens, receptors, or signaling peptides in the outer leaflet of the membrane, thereby decreasing a cellular activity.

* * * * *

SEQUENCE LISTING

<160> NUMBER OF SEQ ID NOS: 12

<210> SEQ ID NO 1
<211> LENGTH: 47
<212> TYPE: DNA
<213> ORGANISM: Artificial Sequence
<220> FEATURE:
<223> OTHER INFORMATION: Synthetic construct

<400> SEQUENCE: 1
cctttccacg aacacagggt tgtccgatcc tatattacga ctcctttt        47

<210> SEQ ID NO 2
<211> LENGTH: 34
<212> TYPE: DNA
<213> ORGANISM: Artificial Sequence
<220> FEATURE:
<223> OTHER INFORMATION: Synthetic construct

<400> SEQUENCE: 2
tttgggaagg ggttcgcaag tcgcaccta aacg        34

<210> SEQ ID NO 3
<211> LENGTH: 36

```
<212> TYPE: DNA
<213> ORGANISM: Artificial Sequence
<220> FEATURE:
<223> OTHER INFORMATION: Synthetic construct

<400> SEQUENCE: 3
tcttatcctg catcgaaagc tcaatcatgc atcttt                              36

<210> SEQ ID NO 4
<211> LENGTH: 23
<212> TYPE: DNA
<213> ORGANISM: Artificial Sequence
<220> FEATURE:
<223> OTHER INFORMATION: Synthetic construct

<400> SEQUENCE: 4
tttatgttga aggctcagga tgc                                            23

<210> SEQ ID NO 5
<211> LENGTH: 36
<212> TYPE: DNA
<213> ORGANISM: Artificial Sequence
<220> FEATURE:
<223> OTHER INFORMATION: Synthetic construct

<400> SEQUENCE: 5
tttatcggac attcaacatg gagtcgtggt gcgact                              36

<210> SEQ ID NO 6
<211> LENGTH: 34
<212> TYPE: DNA
<213> ORGANISM: Artificial Sequence
<220> FEATURE:
<223> OTHER INFORMATION: Synthetic construct

<400> SEQUENCE: 6
tgcgaacagg ataagacgtt tagaatatag gttt                                34

<210> SEQ ID NO 7
<211> LENGTH: 47
<212> TYPE: DNA
<213> ORGANISM: Artificial Sequence
<220> FEATURE:
<223> OTHER INFORMATION: Synthetic construct

<400> SEQUENCE: 7
tttttcgatg cccctteccg atgcatgaag gcatcctga gccaccc                   47

<210> SEQ ID NO 8
<211> LENGTH: 23
<212> TYPE: DNA
<213> ORGANISM: Artificial Sequence
<220> FEATURE:
<223> OTHER INFORMATION: Synthetic construct

<400> SEQUENCE: 8
tgtgttcgtg gaattgagct ttt                                            23

<210> SEQ ID NO 9
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(35)
```

```
<223> OTHER INFORMATION: attached to cholesterol TEG moiety

<400> SEQUENCE: 9
tttgggaagg ggttcgcaag tcgcacccta aacga                               35

<210> SEQ ID NO 10
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (24)..(24)
<223> OTHER INFORMATION: attached to cholesterol TEG moiety

<400> SEQUENCE: 10
tttatgttga aggctcagga tgca                                           24

<210> SEQ ID NO 11
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (34)..(34)
<223> OTHER INFORMATION: attached to Cy3 tag

<400> SEQUENCE: 11
tgcgaacagg ataagacgtt tagaatatag gttt                                34

<210> SEQ ID NO 12
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (23)..(23)
<223> OTHER INFORMATION: attached to Cy3 tag

<400> SEQUENCE: 12
tgtgttcgtg gaattgagct ttt                                            23
```